United States Patent
Maurer et al.

(10) Patent No.: US 12,060,421 B2
(45) Date of Patent: Aug. 13, 2024

(54) ANTIBODIES TO TIGIT

(71) Applicant: BRISTOL-MYERS SQUIBB COMPANY, Princeton, NJ (US)

(72) Inventors: Mark F. Maurer, Seattle, WA (US); Tseng-hui Timothy Chen, Burlingame, CA (US); Brigitte Devaux, Palo Alto, CA (US); Mohan Srinivasan, Cupertino, CA (US); Susan H. Julien, Seattle, WA (US); Paul O. Sheppard, Granite Falls, WA (US); Daniel F. Ardourel, Woodinville, WA (US); Indrani Chakraborty, Fremont, CA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 371 days.

(21) Appl. No.: 17/227,642

(22) Filed: Apr. 12, 2021

(65) Prior Publication Data

US 2021/0324072 A1  Oct. 21, 2021

Related U.S. Application Data

(60) Continuation of application No. 16/228,095, filed on Dec. 20, 2018, now Pat. No. 11,008,390, which is a division of application No. 14/977,789, filed on Dec. 22, 2015, now Pat. No. 10,189,902.

(60) Provisional application No. 62/096,267, filed on Dec. 23, 2014.

(51) Int. Cl.
  *C07K 16/28*  (2006.01)
  *A61K 39/00*  (2006.01)
  *A61P 35/00*  (2006.01)

(52) U.S. Cl.
  CPC .......... *C07K 16/2803* (2013.01); *A61P 35/00* (2018.01); *A61K 2039/505* (2013.01); *C07K 2317/21* (2013.01); *C07K 2317/31* (2013.01); *C07K 2317/34* (2013.01); *C07K 2317/76* (2013.01); *C07K 2317/92* (2013.01); *Y02A 50/30* (2018.01)

(58) Field of Classification Search
  None
  See application file for complete search history.

(56) References Cited

U.S. PATENT DOCUMENTS 8,822,642 B2  9/2014  Levin et al.
2007/0054360 A1  3/2007  Gao et al.

FOREIGN PATENT DOCUMENTS

| | | |
|---|---|---|
| WO | WO 2004/024068 A2 | 3/2004 |
| WO | WO 2009/126688 A2 | 10/2009 |
| WO | WO2013/144567 A1 | 10/2013 |
| WO | WO 2014 089169 A2 | 6/2014 |
| WO | WO 2015/009856 A2 | 1/2015 |
| WO | WO 2015/143343 A2 | 9/2015 |
| WO | WO2016/011264 A1 | 1/2016 |
| WO | WO2016/028656 A1 | 2/2016 |
| WO | WO2016/191643 A1 | 12/2016 |
| WO | WO2017-53748 A1 | 3/2017 |

OTHER PUBLICATIONS

Hall, 1992, J. Immunol. vol. 149: 1605-1612 Holt, 2003, Trends biotech. vol. 21: 484-490.*
Rabia et al. 2018, Biochem. Eng. J. vol. 137: 365-374 Pauken, Dec. 8, 2014, Cancer Cell, vol. 26: 785-787.*
Scott et al., 2012, vol. 12. Nature Reviews, pp. 278-287 Chen, 2018, Front. Immunol., vol. 9, pp. 1-7.*
Rouet, 2015, J. Biol. Chem. vol. 290: 11905-11917.*
Gunter Bernhardt, *Eur. Journal of Immunology*, "TIGIT Versus CD226", vol. 44, pp. 307-308 2014.
Chauvin et al., *Journal of Clinical Invest*, "TIGIT and PD-1 Impair Tumor Antigen-Specific CD8 T Cells In Melanoma Patients", vol. 125: 5, pp. 2046-2058, May 2015.
Grogan et al., *Journal Immunology*, "TIGIT Inhibits CD8+ T Cell Effector Function During Chronic Viral Infection and Cancer", vol. 192(1): Suppl. 203.15: TUM7P.933. May 1, 2014.
Gur et al., *Immunity*, "Binding of the FAP2 Protein of Fusobacterium Nucleatum to Human Inhibitory Receptor TIGIT Protects Tumors From Immune Cell Attack", vol. 42, pp. 344-355 , Feb. 17, 2015.
Tracy Hampton, *J.Am. Med. Assn.*, "Lab Reports; Bacteria Protect Colorectal Cancer Cells From Immune Destruction", vol. 313: No. 13, p. 1305, Apr. 7, 2015.
T. Inozume et al., *J. Invest. Dermatol.*, "CD155/TIGIT Interaction is an Immune Checkpoint Regulating Antimelanoma Immune Responses", Abstracts for Pigmentation and Melanoma, vol. 134(Suppl. 1), p. S121, Abstr. 693, 2014.
T. Inozume et al., *J. Invest. Dermatol.*, "Blockade For CD155-TIGIT Interaction is an Effective Therapy for Melanoma", vol. 135(Suppl. 1), p. S1, May 2015.

(Continued)

*Primary Examiner* — Amy E Juedes
(74) *Attorney, Agent, or Firm* — Gregory R. Bellomy

(57) ABSTRACT

The present invention provides antibodies, or antigen binding fragments thereof, that bind to human TIGIT (T cell immunoreceptor with Ig and ITIM domains), as well as uses of these antibodies or fragments in therapeutic applications, such as in the treatment of cancer or chronic viral infection. Such method of treatment include combination therapy with inhibitors of other immunomodulatory receptor interactions, such as the PD-1/PD-L1 interaction. The invention further provides polynucleotides encoding the heavy and/or light chain variable region of the antibodies, expression vectors comprising the polynucleotides encoding the heavy and/or light chain variable region of the antibodies, cells comprising the vectors, and methods of making the antibodies or fragments by expressing them from the cells.

6 Claims, 10 Drawing Sheets
Specification includes a Sequence Listing.

(56) References Cited

OTHER PUBLICATIONS

Johnston et al, *Cancer Cell*, "The Immunoreceptor TIGIT Regulates Antitumor and Antiviral CD8+ T Cell Effector Function", vol. 26, pp. 923-937, Dec. 8, 2014.
Robert J. Johnston, *Keystone Symposia: Immune Evolution and Cancer*, Mar. 9-14, 2014 Whistler, BC, Canada, "TIGIT Inhibits CD8+ T Cell Effector Function During Chronic Viral Infection and Cancer", Poster X2 2003, Mar. 11, 2014.
Joller et al, *Journal Immunology*, "Cutting Edge: TIGIT Has T Cell-Intrinsic Inhibitory Functions", vol. 186, pp. 1338-1342, 2011.
Joller et al, Immunity, "Treg Cells Expressing the Coinhibitory Molecule TIGIT Selectively Inhibit Proinflammatory Th1 and Th17 Cell Responses", vol. 40, pp. 569-581, Apr. 17, 2014.
Laetitia Comps-Agrar et al., *Journal Immunology*, "TIGIT Mediated T Cell Exhaustion in Cancer is Dependent on TIGIT/CD226 Interaction", vol. 192(1) Suppl. 71.31: TUM2P.907 May 1, 2014.
Lozano et al, *Journal Immunology*, "The TIGIT/CD226 Axis regulates Human T Cell Function", vol. 188, pp. 3869-3875, Mar. 16, 2012.
Stanietsky et al, *PNAS*, "The Interaction of TIGIT with PVR and PVRL2 Inhibits Human NK Cell Cytotoxicity", vol. 106, pp. 17858-17863, Oct. 20, 2009.
Stengel et al, *PNAS*, "Structure of TIGIT Immunoreceptor Bound to Poliovirus Receptor Reveals a Cell-Cell Adhesion and Signaling Mechanism That Requires Cis-Trans Receptor clustering", vol. 109, pp. 5399-5404, Apr. 3, 2012.
Yu et al, *Nature Immunology*, "The Surface Protein TIGIT Suppresses T Cell Activation by Promoting the Generation of Mature Immunoregulatory Dendritic Cells", vol. 10:, No. 1, pp. 48-57, Jan. 2009.
GenBank Accession No. Z82148.1; pp. 1-2; 1997.
Shriner et al.; Vaccine; vol. 24; pp. 7197-7203; 2006.
Klein et al.; Blood; vol. 89; pp. 1288-1298; 1997.
GenBank Accession No. DQ535178.1; pp. 1-2; 2006.
Chan et al., Receptors that Interact with Nectin and Nectin-like Proteins in the Immunosurveillance and Immunotherapy of Cancer, ScienceDirect, 2012, 246-251, 24, Elsevier.
European Patent Office, Extended European Search Report, Oct. 25, 2023, 12 Pages.
Kurtulus et al., Mechanisms of TIGIT-driven Immune Suppression in Cancer, Journal of ImmunoTherapy of Cancer, 2014, 1 page, 2(Suppl 3):O13.

\* cited by examiner colon epithelium colon adenocarcinoma

ANTIBODIES TO TIGIT

CROSS-REFERENCE TO RELATED APPLICATIONS

This application claims the benefit under 35 U.S.C. § 119(e) of U.S. Provisional Application No. 62/096,267, filed Dec. 23, 2014, the disclosure of which is incorporated herein by reference.

SEQUENCE LISTING

Incorporated herein by reference in its entirety is a Sequence Listing named "SEQT_12437USNP.txt," comprising SEQ ID NO:1 through SEQ ID NO:53, which include nucleic acid and/or amino acid sequences disclosed herein. The Sequence Listing has been submitted herewith in ASCII text format via EFS-Web, and thus constitutes both the paper and computer readable form thereof. The Sequence Listing was first created using PatentIn 3.5 on Dec. 15, 2015, and is approximately 46 KB in size.

BACKGROUND OF THE INVENTION

TIGIT (T cell immunoreceptor with Ig and ITIM domains) is a co-inhibitory receptor protein also known as WUCAM, Vstm3 or Vsig9. TIGIT was discovered in genomic searches for proteins specifically expressed on T cells, and has an immunoglobulin variable domain, a transmembrane domain, and an immunoreceptor tyrosine-based inhibitory motif (ITIM), and contains signature sequence elements of the PVR protein family. It is known to interact with poliovirus receptor (PVR; CD155) and with nectin2 (CD112). See e.g. Stengel et al. (2012) *Proc. Nat'l Acad. Sci.* (USA) 19:5399; WO 2006/124667; WO 2009/126688. Although PVR may interact with the co-activating receptor DNAM-1 (CD226) to enhance tumor killing, the high affinity TIGIT/PVR interaction would inhibit such killing, and may act to prevent killing of normal (self) cells that also express PVR. Stanietsky et al. (2009) *Proc. Nat'l Acad. Sci.* (USA) 106:17858. The dominance of this inhibitory interaction may be important in suppression of anti-self immune reactions, but in the tumor context it suppresses tumor eradication. Id.

TIGIT suppresses T cell activation by promoting the generation of mature immunoregulatory dendritic cells. Yu et al. (2009) *Nat. Immunol.* 10:48. TIGIT and other such co-inhibitory molecules (e.g. CTLA-4, PD-1, Lag3 and BTLA) may play a role in evasion of immunosurveillance by tumor cells. Experiments have shown that PVR/CD155 is over-expressed on melanoma cells (Inozume et al. (2014) *J. Invest. Dermatol.* 134:S121—Abstract 693) and various other tumors. It is possible that the TIGIT/PVR interaction can shield such tumor cells from immune-mediated eradication by inhibiting anti-tumor responses of T and NK cells. Stanietsky et al. (2009) *Proc. Nat'l Acad. Sci.* (USA) 106: 17858 and Lozano et al. (2012) *J. Immunol.* 188:3869. Other experiments have identified a TIGIT$^+$ subset of regulatory T cells (T$_{regs}$) that selectively suppress Th1 and Th17 responses (Joller et al. (2014) *Immunity* 40:569), suggesting an alternative mechanism by which an anti-TIGIT antibody may enhance anti-tumor immune response.

TIGIT may act to "turn off" the immune response similarly to other co-inhibitory receptors such as CTLA-4, PD-1 and BTLA. Id. Antibodies targeting CTLA-4 (ipilimumab) and PD-1 (nivolumab, pembrolizumab) have been approved for the treatment of human cancers, validating this therapeutic approach. Antibodies that bind to human TIGIT might also find use in treatment of cancers. See e.g. WO 2006/124667. In mouse models, antibody blockade of both PD-L1 and TIGIT leads to a synergistic enhancement of CD8$^+$ T cell mediated tumor rejection. Grogan et al. (2014) *J. Immunol.* 192(1) Suppl. 203.15; Johnston et al. (2014) *Cancer Cell* 26:1-15. Similar results have been obtained in animal models of melanoma. Inozume et al. (2014) *J. Invest. Dermatol.* 134:S121—Abstract 693. Some experiments suggest that TIGIT blockade is effective to enhance anti-tumor CD8$^+$ T cell response only in the presence of the co-activating receptor DNAM-1/CD226, which competes with TIGIT for binding to PVR/CD155. Johnston et al. (2014) *Cancer Cell* 26:1-15.

Recent experiments have demonstrated that intratumoral bacteria expressing Fap2 protein may inhibit NK cell mediated tumor killing by binding to TIGIT (Gur et al. (2015) *Immunity* 42:344), suggesting that eliminating such bacteria, blocking the interaction of TIGIT with Fap2, or blocking the activity of TIGIT generally, may be useful in treatment of cancer, e.g. colorectal cancer. Hampton (2015) *JAMA* 313: 1305.

The need exists for improved methods of treating cancer and chronic viral infections and medicaments, such as therapeutic monoclonal antibodies, for use in the methods. Medicines for use in such improved methods of treatment may comprise antibodies or antibody fragments that specifically bind to TIGIT and reverse or partially reverse the TIGIT-mediated suppression of anti-tumor or anti-viral immune responses.

SUMMARY OF THE INVENTION

The present invention provides improved medicines and methods of treatment for cancer and chronic viral infection comprising antibodies, or antigen-binding fragments thereof, that bind to huTIGIT. Provided herein are isolated antibodies, such as monoclonal antibodies, in particular human monoclonal antibodies, that specifically bind huTIGIT and have desirable functional properties, such as high affinity specific binding to huTIGIT, binding to monkey TIGIT (e.g., cynomolgus TIGIT), the ability to block binding of TIGIT to PVR and/or Nectin-2, the ability to block the interaction of TIGIT with DNAM, or any combination of these properties.

The present invention further provides improved methods of treating cancer and therapeutic antibodies for use in the methods, including cancers in which TIGIT-mediated signaling suppresses anti-tumor immune response, tumors in which TIGIT interaction with the co-activating receptor DNAM-1/CD226 suppresses anti-tumor immune response, tumors in which TIGIT-expressing regulatory T cells suppress anti-tumor immune response, or tumors in which TIGIT otherwise inhibits anti-tumor immune response. The invention also provides methods and therapeutic antibodies for use in treating chronic viral infections in which TIGIT suppresses anti-viral immune response.

In another aspect, the present invention relates to antibodies that compete with the antibodies having heavy and light chain variable domain sequences disclosed herein for binding to huTIGIT, and/or that cross-block the antibodies having heavy and light chain variable domain sequences disclosed herein from binding to huTIGIT.

In certain embodiments, the anti-TIGIT antibodies of the present invention, or antigen binding fragments thereof, enhance an anti-tumor immune response, e.g. an antigen-specific T cell response. In other embodiments, the anti- TIGIT antibodies of the present invention, or antigen binding fragments thereof, block TIGIT mediated inhibitory signaling allowing PVR/DNAM co-stimulation of NK cells to increase NK-mediated anti-tumor response killing. In yet another embodiment the anti-TIGIT antibodies of the present invention, or antigen binding fragments thereof, deplete a population of regulatory T cells within a tumor that would otherwise suppress anti-tumor immune response. In yet another embodiment, anti-TIGIT antibodies of the present invention formatted as IgG1s deplete CD8$^+$ exhausted T cells and T$_{regs}$, allowing for the influx of fresh, non-exhausted CD8$^+$ T cells. In other embodiments the anti-TIGIT antibodies of the present invention, or antigen binding fragments thereof, act by one of more of the above-referenced mechanisms since the mechanisms are not necessarily mutually exclusive.

In certain embodiments, the anti-TIGIT antibodies of the present invention, or antigen binding fragments thereof, do not bind to activating Fcγ receptors (FcγRs), e.g. in embodiments relying on enhancing the anti-tumor activity of TIGIT-expressing cells. In alternative embodiments, the anti-TIGIT antibodies of the present invention, or antigen binding fragments thereof, bind to one or more activating FcγRs, e.g. in embodiments relying on killing of TIGIT-expressing cells, such as exhausted CD8$^+$ T cells or T$_{regs}$.

The present invention also provides isolated monoclonal antibodies (15A6), or antigen binding fragments thereof, that specifically bind to huTIGIT and comprise heavy chain CDRH1, CDRH2, and CDRH3 sequences comprising SEQ ID NOs: 14, 15 and 16, respectively, and/or light chain CDRL1, CDRL2, and CDRL3 sequences comprising SEQ ID NOs: 17, 18, and 19, respectively.

The present invention also provides isolated monoclonal antibodies (22G2), or antigen binding fragments thereof, that specifically bind to huTIGIT and comprise heavy chain CDRH1, CDRH2, and CDRH3 sequences comprising SEQ ID NOs: 20, 21 and 22, respectively, and/or light chain CDRL1, CDRL2, and CDRL3 sequences comprising SEQ ID NOs: 23, 24, and 25, respectively.

The present invention further provides isolated monoclonal antibodies (11G11), or antigen binding fragments thereof, that specifically bind to huTIGIT and comprise heavy chain CDRH1, CDRH2, and CDRH3 sequences comprising SEQ ID NOs: 26, 27 and 28, respectively, and/or light chain CDRL1, CDRL2, and CDRL3 sequences comprising SEQ ID NOs: 29, 30, and 31, respectively.

The present invention yet further provides isolated monoclonal antibodies (10D7), or antigen binding fragments thereof, that specifically bind to huTIGIT and comprise heavy chain CDRH1, CDRH2, and CDRH3 sequences comprising SEQ ID NOs: 32, 33 and 34, respectively, and/or light chain CDRL1, CDRL2, and CDRL3 sequences comprising SEQ ID NOs: 35, 36, and 37, respectively.

The present invention also provides isolated monoclonal antibodies, or antigen binding fragments thereof, that specifically bind to huTIGIT and comprise the variable heavy chain and variable light chain sequence disclosed at SEQ ID NOs: 2 (or 3, 4, 5) and 6; SEQ ID NOs: 7 (or 8) and 9; SEQ ID NOs: 10 and 11; and SEQ ID NOs: 12 and 13.

The present invention provides isolated monoclonal antibodies, or antigen binding fragments thereof, that bind to huTIGIT and comprise heavy and light chain variable regions, wherein the heavy chain variable region comprises an amino acid sequence that is at least 90%, 95% or 99% identical to the amino acid sequence selected from the group consisting of SEQ ID NOs: 2, 3, 4, 5, 7, 8, 10 and 12.

The present invention also provides isolated monoclonal antibodies, or antigen binding fragments thereof, that bind to huTIGIT and comprise heavy and light chain variable regions, wherein the light chain variable region comprises an amino acid sequence that is at least 90%, 95% or 99% identical to the amino acid sequence selected from the group consisting of SEQ ID NOs: 6, 9, 11, and 13.

In certain embodiments, the isolated monoclonal antibodies of the present invention, or antigen binding fragments thereof, (a) bind to the same epitope on huTIGIT as 15A6, 22G2, 11G11, and/or 10D7, and/or (b) inhibit binding of 15A6, 22G2, 11G11, and/or 10D7 to huTIGIT as measured, e.g., by FACS or ELISA.

In certain embodiments, the anti-huTIGIT antibodies of the present invention, or antigen binding fragments thereof, bind to an epitope comprising or consisting of one or more of residues E60, I109, L65, N70, F107, T117, I68, H76 and N58 (antibody 22G2) of huTIGIT (SEQ ID NO: 1), at an epitope comprising or consisting of one or more of residues G74, N70, H76, L65, L73, Q56, I68, H111 and P114 (antibody 11G11), or at an epitope comprising or consisting of one or more of residues H76, G74, L65, N58, I68, Q139, G135, L73, F107, N70, E60, H134, A132 and I109 (antibody 15A6).

Alternatively, the anti-huTIGIT antibodies of the present invention, or antigen binding fragments thereof, bind at an epitope comprising or consisting of one or more sequences selected from the group consisting of NWEQQDQLLA-ICNADLGWH (SEQ ID NO: 38) and FCIYHTYPDGT (SEQ ID NO: 39) (antibody 22G2), or from the group consisting of QVNWEQQDQLLAICNADLGWH (SEQ ID NO: 40) and HTYP (SEQ ID NO: 41) (antibody 11G11), or from the group consisting of NWEQQDQLLA-ICNADLGWH (SEQ ID NO: 38), FCI, and AEHGARFQ (SEQ ID NO: 43) (antibody 15A6).

In still further embodiments, the anti-TIGIT antibody of the present invention, or antigen binding fragment thereof, binds to a core epitope on huTIGIT (SEQ ID NO: 1) comprising or consisting of one or more of residues L65, I68, N70 and H76, and/or at an epitope comprising or consisting of LLAICNADLGWH (SEQ ID NO: 44).

In some embodiments, the anti-huTIGIT antibodies of the present invention, or antigen binding fragments thereof, also bind to cynomolgus TIGIT.

In various embodiments, the anti-TIGIT antibodies, or antigen-binding fragments thereof, of the present invention are human IgG1, IgG2, IgG3, or IgG4 antibodies, or variants thereof. In certain embodiments, including but not limited to methods of blocking TIGIT signaling in "exhausted" tumor-specific T cells or blocking inhibitory signals on NK cells allowing DNAM-1/PVR-mediated co-stimulation or methods of blocking TIGIT interaction with DNAM-1/CD226 to impair DNAM-1 homodimerization, the anti-TIGIT antibodies, or antigen-binding fragments thereof, comprise an effectorless or mostly effectorless Fc. Such Fc regions include, e.g., human IgG2 or IgG4, or an effectorless variant of human IgG1 with one or more of the following mutations: L234A, L235E, G237A, A330S and P331S (EU numbering), including IgG1.1f (SEQ ID NO: 48) comprising all five of the listed mutations.

In alternative embodiments, including but not limited to methods of depleting TIGIT$^+$ regulatory T cells, the anti-TIGIT antibodies, or antigen-binding fragments thereof, comprise an Fc that preferentially binds to an activating FcγR (FcγRI, FcγRIIa or FcγRIIIa), such as a human IgG1, or a sequence variant having enhanced binding to an activating FcγR relative to a wild-type IgG1 Fc. In embodiments involving use of IgG1 forms of the anti-TIGIT antibodies of the present invention to drive depletion of $T_{regs}$, intratumoral injection may be optionally used to localize effects to the tumor microenvironment, minimizing potential side effects caused by activity in peripheral tissues.

In certain embodiments, methionine residues in the CDR regions of the anti-TIGIT antibodies of the present invention (e.g. M115 in CDRH3 of 10D7, SEQ ID NO: 34), or antigen-binding fragments thereof, are replaced with amino acid residues that do not undergo oxidation.

In certain embodiments, the anti-huTIGIT antibodies that compete for binding, cross-block, or bind to the same epitope as 15A6, 22G2, 11G11 or 10D7, or antigen-binding fragments thereof, are human or humanized antibodies.

In some embodiments, the anti-huTIGIT antibodies of the present invention are not, or do not bind to the same epitope as, antibodies described at U.S. Pat. App. Pub. No. 2009/0258013, e.g. they do not bind to the same epitope as anti-huTIGIT mAb 10A7 or 1F4. See also Johnston et al. (2014) *Cancer Cell* 26:1; Yu et al. (2009) *Nat. Immunol.* 10:48.

In other embodiments, the anti-huTIGIT antibodies comprise variable domains derived from the same human V domain germline sequences as the antibodies disclosed herein, including heavy chain V domains V4-39, V4-61, or V1-69. In more specific embodiments, the anti-huTIGIT antibodies comprise heavy and light chain variable domains derived from the same human heavy and light chain V domain germline sequences as the antibodies disclosed herein, such as V4-39/VA27 (15A6), V4-61/VL6 (22G2), V4-39/VL6 (11G11), and V1-69NL15 (10D7).

In various embodiments anti-huTIGIT antibodies of the present invention bind to huTIGIT with a $K_D$ of less than 10 nM, 5 nM, 2 nM, 1 nM, 300 pM or 100 pM. In other embodiments, the anti-huTIGIT antibodies of the present invention bind to huTIGIT with a $K_D$ between 2 nM and 100 pM.

In other embodiments, the anti-huTIGIT antibodies of the present invention consist essentially of, or comprise, some combination of the CDRs of antibodies 15A6, 22G2, 11G11 and 10D7, such as CDRH1 (SEQ ID NOs: 14, 20, 26 and 32); CDRH2 (SEQ ID NOs: 15, 21, 27 and 33); CDRH3 (SEQ ID NOs: 16, 22, 28 and 34); CDRL1 (SEQ ID NOs: 17, 23, 29 and 35); CDRL2 (SEQ ID NOs: 18, 24, 30 and 36); and CDRL3 (SEQ ID NOs: 19, 25, 31 and 37). In other embodiments the antibodies consist essentially of, or comprise, the separate specific combinations of the CDR sequences of antibodies 15A6, 22G2, 11G11 and 10D7.

In further embodiments the anti-huTIGIT antibodies of the present invention consist essentially of, or comprise, the heavy and/or light chain variable domains of antibodies 15A6 (SEQ ID NOs: 2-5 and 6), 22G2 (SEQ ID NOs: 7-8 and 9), 11G11 (SEQ ID NOs: 10 and 11) and 10D7 (SEQ ID NOs: 12 and 13), or sequences sharing at least 80%, 85%, 90% and 95% sequence identity with these disclosed sequences.

In yet further embodiments the anti-huTIGIT antibodies of the present invention consist essentially of, or comprise, heavy and/or light chains comprising the variable domain sequences of antibodies 15A6 (SEQ ID NOs: 2-5 and 6), 22G2 (SEQ ID NOs: 7-8 and 9), 11G11 (SEQ ID NOs: 10 and 11) and 10D7 (SEQ ID NOs: 12 and 13), or sequences sharing at least 80%, 85%, 90% and 95% sequence identity with these disclosed sequences.

In other embodiments the antigen binding domains of the antibodies of the present invention are present in bispecific molecules further comprising an antigen binding domain that binds specifically to a different immunomodulatory receptor, including but not limited to PD-1, CTLA-4 or LAG3.

The present invention further provides nucleic acids encoding the heavy and/or light chain variable regions, of the anti-huTIGIT antibodies of the present invention, or antigen binding fragments thereof, expression vectors comprising the nucleic acid molecules, cells transformed with the expression vectors, and methods of producing the antibodies by expressing the cells transformed with the expression vectors and recovering the antibody.

The present invention also provides immunoconjugates comprising the anti-huTIGIT antibodies described herein, linked to an agent, such as a detectable label or cytotoxic agent.

The present invention also provides pharmaceutical compositions comprising anti-huTIGIT antibodies of the present invention, or antigen binding fragments thereof, and a carrier. Also provided herein are kits comprising the anti-TIGIT antibodies, or antigen binding fragments thereof, and instructions for use.

In another aspect, the present invention provides a method of enhancing an antigen-specific T cell response comprising contacting the T cell with an anti-huTIGIT antibody of the present invention, or antigen binding fragment thereof, such that an antigen-specific T cell response is enhanced, e.g. by reduction of an inhibitory signal that would otherwise dampen anti-tumor response. In some embodiments, the antigen-specific T cell is a tumor-antigen specific effector T cell, such as a $CD8^+$ T cells, and the enhancement, e.g. through blocking of a TIGIT-mediated inhibitory effect, results in increased anti-tumor activity. Anti-huTIGIT antibodies of the present invention, or antigen-binding fragments thereof, may also reduce inhibitory signals in NK cells and thus increase their anti-tumor activity. Without intending to be limited by theory, anti-huTIGIT antibodies of the present invention increase effector T cell or NK cell function by blocking binding of TIGIT to PVR, thus reducing or eliminating an inhibitory signal that would otherwise be delivered to the cell. Alternatively, or in addition, anti-TIGIT antibodies of the present invention, or antigen binding fragments thereof, may inhibit interaction between TIGIT and DNAM-1/CD226 that would otherwise reduce DNAM-1-mediated immune activation.

The present invention further provides a method of increasing IL-2 and/or IFN-γ production in, and/or proliferation of, a T cell comprising contacting the T cell with an effective amount of an anti-TIGIT antibody, or antigen binding fragment thereof.

In another aspect, the present invention provides a method of reducing or depleting $T_{regs}$ in a tumor in a subject in need thereof comprising administering an effective amount of an anti-huTIGIT antibody of the present invention, wherein the antibody has effector function or enhanced effector function, to reduce the number of $T_{regs}$ in the tumor.

The present invention provides a method of enhancing an immune response in a subject comprising administering an effective amount of an anti-huTIGIT antibody of the present invention, or antigen binding fragment thereof, to the subject such that an immune response in the subject is enhanced. In certain embodiments, the subject has a tumor and an immune response against the tumor is enhanced. In another embodiment, the subject has a viral infection and an antiviral immune response is enhanced.

The present invention also provides a method of inhibiting the growth of tumors in a subject comprising administering to the subject an anti-huTIGIT antibody of the present invention, or antigen binding fragment thereof, such that growth of the tumor is inhibited.

The present invention further provides a method of treating cancer, e.g., by immunotherapy, comprising administering to a subject in need thereof a therapeutically effective amount an anti-huTIGIT antibody of the present invention, or antigen binding fragment thereof, e.g. as a pharmaceutical composition, thereby treating the cancer. In certain embodiments, the cancer is bladder cancer, breast cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, and virus-related cancer. In certain embodiments, the cancer is a metastatic cancer, refractory cancer, or recurrent cancer.

In certain embodiments, the methods of modulating immune function and methods of treatment described herein comprise administering an anti-huTIGIT antibody of the present invention in combination with, or as a bispecific reagent with, one or more additional therapeutics, for example, an anti-PD-1 antibody, an anti-PD-L1 antibody, an anti-LAG3 antibody, an anti-GITR antibody, an anti-OX40 antibody, an anti-CD73 antibody, an anti-CD40 antibody, an anti-CD137 mAb, an anti-CD27 mAb, an anti-CSF-1R antibody, and/or an anti-CTLA-4 antibody, a TLR agonist, or a small molecule antagonist of IDO or TGFβ. In specific embodiments, anti-huTIGIT therapy is combined with anti-PD-1 and/or anti-PD-L1 therapy, e.g. treatment with an antibody or antigen binding fragment thereof that binds to human PD-1 or an antibody or antigen binding fragment thereof that binds to human PD-L1.

In some embodiments, samples from patients, e.g. biopsies, are screened for expression of DNAM-1 on T cells or NK cells to select patients most likely to respond to anti-TIGIT therapy, wherein the presence of DNAM-1 on T cells suggests a the patient will have a beneficial anti-tumor response upon anti-TIGIT therapy, e.g. treatment with the anti-huTIGIT antibody or fragment of the present invention, and the absence of DNAM-1 identifies patients that are less likely to benefit from anti-TIGIT therapy. In other embodiments, samples from patients are screened for expression of PVR and/or Nectin-2 on tumor cells or tumor infiltrating myeloid cells to select patients most likely to respond to anti-TIGIT therapy, wherein the presence of PVR and/or Nectin-2 suggests a the patient will have a beneficial anti-tumor response upon anti-TIGIT therapy, e.g. treatment with the anti-huTIGIT antibody or fragment of the present invention, and the absence of PVR and/or Nectin-2/CD112 identifies patients that are less likely to benefit from anti-TIGIT therapy. In various embodiments, cell-surface expression of TIGIT, DNAM, PVR and/or Nectin-2 is by FACS, IHC or LC-MS. In another aspect, the present invention provides methods of treatment of subjects in need thereof involving determination of the cell-surface expression of TIGIT, DNAM, PVR and/or Nectin-2 as described herein and administration of anti-TIGIT antibodies of the present invention preferentially, or exclusively, to those for whom is it most likely to provide therapeutic benefit.

In one embodiment, the level of soluble PVR and/or soluble Nectin-2 (sPVR, sNectin-2) is measured in subjects being considered for treatment with anti-TIGIT antibodies of the present invention, and only subjects exhibiting elevated soluble PVR and/or Nectin-2 are treated with the antibodies. In some embodiments, sPVR and/or sNectin-2 is detected in serum by ELISA or LC-MS.

The present invention also provides methods of detecting the presence of TIGIT in a sample, on a cell within a sample (e.g. FACS), or in specific locations in a cell or tissue (e.g. IHC), or of sorting cells based on the presence or absence of TIGIT on their surface (e.g. FACS), comprising contacting the sample with an anti-huTIGIT antibody of the present invention, or an antigen binding fragment thereof, under conditions that allow for formation of a complex between the antibody, or antigen binding fragment thereof, and TIGIT, and detecting the formation of the complex. In some embodiments the anti-TIGIT antibody used for detection is conjugated with a detectable label.

Other features and advantages of the instant disclosure will be apparent from the following detailed description and examples, which should not be construed as limiting.

BRIEF DESCRIPTION OF THE DRAWINGS

FIG. 5A shows tumor volume (cubic millimeters), calculated by multiplying the square of the width of the tumor by half the length, in a CT26 mouse colon cancer model for mice treated with an anti-mouse TIGIT antibody having an effector function enabled murine IgG2a Fc domain ("TIGIT G2a"), an anti-mouse TIGIT antibody having an effector function deficient IgG1 D265A Fc domain ("TIGIT G1 D265A"), an anti-mouse PD-1 antibody having an effector function deficient IgG1 D265A Fc domain ("PD-1 G1 D265A"), combinations thereof, or a control IgG1 antibody. FIG. 5B shows the effects of anti-TIGIT monotherapy, as well as combination therapy with anti-PD-1 and anti-CTLA-4 antibodies. Tumor volumes are provided along with the number of tumor-free (TF) mice in each group of ten mice at the end of the experiment. Each line represents one mouse. mIgG1 isotype control gave no tumor free mice, as did anti-TIGIT as monotherapy. Anti-PD-1 gave one tumor-free mouse as monotherapy, and five when combined with anti-TIGIT. Anti-CTLA-4 gave three tumor-free mice as monotherapy, and six when combined with anti-TIGIT. See Example 7.

FIG. 6A shows PVR mRNA expression in various tumor types as detected in The Cancer Genome Atlas (TCGA) datasets. Data are provided for adrenocortical carcinoma (ACC), chromophobe renal cell carcinoma (KICH), liver hepatocellular carcinoma (LIHC), colon and rectal adenocarcinoma (COAD, READ), pancreatic ductal adenocarcinoma (PAAD), pheochromocytoma & paraganglioma (PCPG), papillary kidney carcinoma (KIRP), lung adenocarcinoma (LUAD), head and neck squamous cell carcinoma (HNSC), prostate adenocarcinoma (PRAD), uterine corpus endometrial carcinoma (UCEC), cervical cancer (CESC), cutaneous melanoma (SKCM), mesothelioma (MESO), urothelial bladder cancer (BLCA), clear cell kidney carcinoma (KIRC), lung squamous cell carcinoma (LUSC), uterine carcinosarcoma (UCS), sarcoma (SARC), ovarian serous cystadenocarcinoma (OV), papillary thyroid carcinoma (THCA), glioblastoma multiforme (GBM), breast cancer (BRCA), lower grade glioma (LGG), and diffuse large B-cell lymphoma (DLBC). The results disclosed here are in whole or part based upon data generated by the TCGA Research Network. FIG. 6B shows human PVR in colon adenocarcinoma tissue as compared to normal colon epithelium, with darker regions in the adenocarcinoma sample indicating elevated PVR expression. See Example 9.

DETAILED DESCRIPTION

Figure 1:
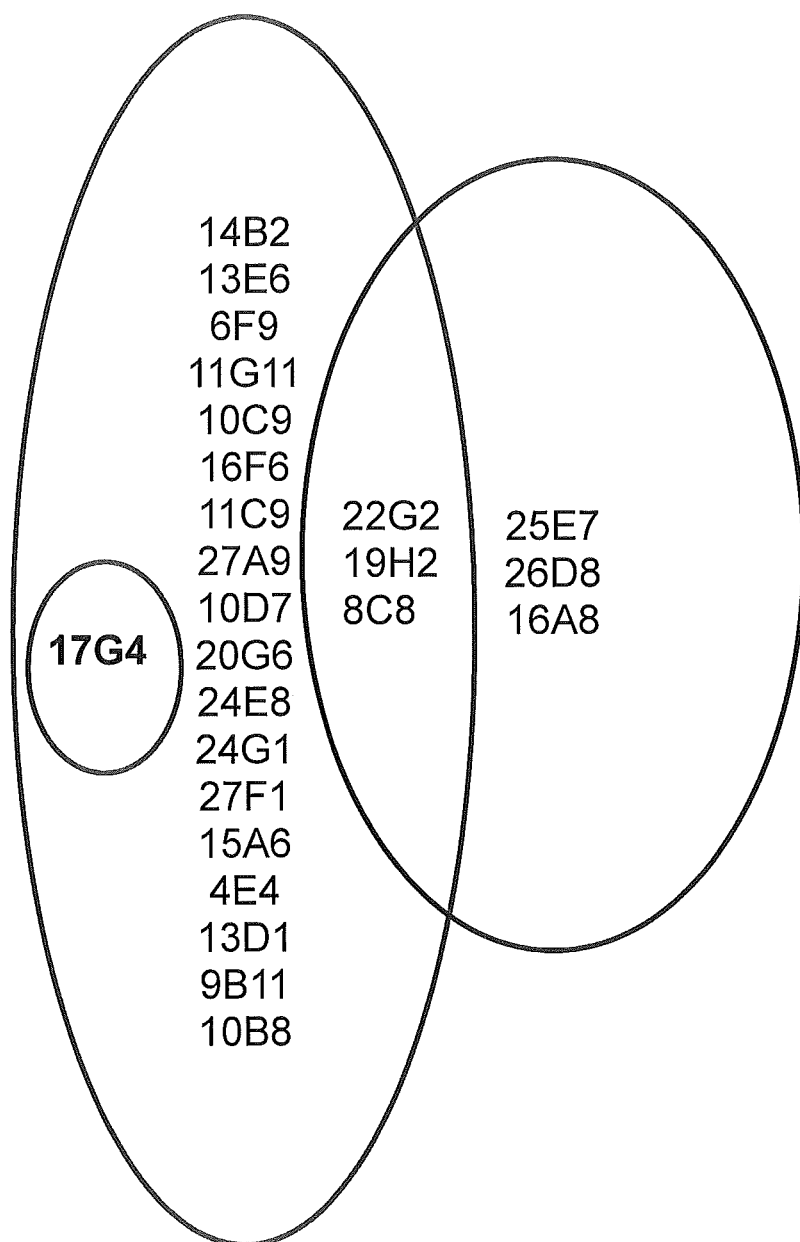
FIG. 1 shows a schematic diagram of "binning" experiments in which various anti-huTIGIT antibodies of the present invention are tested, pairwise, for the ability to block the binding of other antibodies to huTIGIT. Results show that antibodies fall into a limited number of categories, or "bins." See Example 3.

The present invention discloses isolated antibodies, particularly monoclonal antibodies, e.g., human monoclonal antibodies, that specifically bind to human TIGIT ("huTIGIT") and block binding to PVR/CD155, thereby reducing or eliminating the immunosuppressive signal that would otherwise occur in the TIGIT-expressing cells. The present invention also provides isolated antibodies, particularly monoclonal antibodies, e.g., human or humanized monoclonal antibodies, that specifically bind to human TIGIT and block the interaction of human TIGIT to DNAM-1/CD226 that would otherwise prevent the DNAM-1 homodimerization and thus DNAM-1-mediated co-stimulation. Sequences are provided for various human anti-huTIGIT monoclonal antibodies. In certain embodiments, the antibodies described herein are derived from particular heavy and light chain germline sequences and/or comprise particular structural features such as CDR regions comprising particular amino acid sequences.

Further provided herein are methods of making such antibodies, immunoconjugates and bispecific molecules comprising such antibodies or antigen-binding fragments thereof, and pharmaceutical compositions formulated to contain the antibodies or fragments. Also provided herein are methods of using the antibodies for immune response enhancement, alone or in combination with other immunostimulatory agents (e.g., antibodies) and/or cancer or anti-infective therapies. Accordingly, the anti-huTIGIT antibodies described herein may be used in a treatment in a wide variety of therapeutic applications, including, for example, inhibiting tumor growth and treating chronic viral infections.

Definitions

In order that the present description may be more readily understood, certain terms are first defined. Additional definitions are set forth throughout the detailed description.

TIGIT refers to "T cell immunoreceptor with Ig and ITIM domains," a member of the PVR (poliovirus receptor) family of immunoglobin proteins, which binds to PVR/CD155 and Nectin-2/CD112. TIGIT is also referred to as TIGIT, WUCAM, Vstm3 and Vsig9. Unless otherwise indicated, or clear from the context, references to TIGIT herein refer to human TIGIT ("huTIGIT"), and anti-TIGIT antibodies refer to anti-human TIGIT antibodies. Human TIGIT is further described at GENE ID NO: 201633 and MIM (Mendelian Inheritance in Man): 612859. The sequence of human TIGIT (NP_776160.2), including 21 amino acid signal sequence, is provided at SEQ ID NO: 1. Unless otherwise indicated, or clear from the context, "inhibition" of TIGIT refers to blocking of PVR binding and signaling. Anti-TIGIT antibodies of the present invention may act by inhibition of TIGIT signaling, blockade of TIGIT/DNAM-1 interaction and/or other mechanisms, such as directing the depletion of regulatory T cells.

PVR (poliovirus receptor) interacts with TIGIT to induce an immunosuppressive signal. PVR is also referred to as PVS; HVED; CD155; NECL5; TAGE4; Ned-5. Unless otherwise indicated, or clear from the context, references to PVR/CD155 herein refer to human PVR ("huPVR"). Human PVR is further described at GENE ID NO: 5817 and MIM: 173850. There are four known human PVR transcript variants: alpha (NP_006496.4), beta (NP_001129240.1), gamma (NP_001129241.1) and delta (NP_001129242.2), the sequences of which are provided at SEQ ID NOs: 50-53. Unless otherwise indicated, reference to PVR or human PVR relates to the alpha transcript polypeptide.

Unless otherwise indicated or clear from the context, the term "antibody" as used to herein may include whole antibodies and any antigen binding fragments (i.e., "antigen-binding portions") or single chains thereof. An "antibody"

refers, in one embodiment, to a glycoprotein comprising at least two heavy (H) chains and two light (L) chains interconnected by disulfide bonds, or an antigen binding fragment thereof. Each heavy chain is comprised of a heavy chain variable region (abbreviated herein as $V_H$) and a heavy chain constant region. In certain naturally occurring IgG, IgD and IgA antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four framework regions (FRs), arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Antibodies typically bind specifically to their cognate antigen with high affinity, reflected by a dissociation constant ($K_D$) of $10^{-7}$ to $10^{-11}$M or less. Any $K_D$ greater than about $10^{-6}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $5\times10^{-9}$M or less, and most preferably between $10^{-8}$ M and $10^{10}$ M or less, but does not bind with high affinity to unrelated antigens. An antigen is "substantially identical" to a given antigen if it exhibits a high degree of sequence identity to the given antigen, for example, if it exhibits at least 80%, at least 90%, preferably at least 95%, more preferably at least 97%, or even more preferably at least 99% sequence identity to the sequence of the given antigen. By way of example, an antibody that binds specifically to human TIGIT might also cross-react with TIGIT from certain non-human primate species (e.g., cynomolgus monkey), but might not cross-react with TIGIT from other species, or with an antigen other than TIGIT.

Antibodies may exhibit modifications at the N- and/or C-terminal amino acid residues. For example, antibodies of the present invention may be produced from a construct encoding a C-terminal lysine residue, for example on the heavy chain, but such C-terminal lysine may be partially or totally absent in the therapeutic antibody that is sold or administered. Alternatively, an antibody may be produced from constructs that specifically do not encode a C-terminal lysine residue even though such lysine was present in the parental antibody from which the therapeutic antibody was derived. In another example, an N-terminal glutamine or glutamic acid residue in an antibody of the present invention may be partially or fully converted to pyro-glutamic acid in the therapeutic antibody that is sold or administered. Any form of glutamine or glutamic acid present at the N-terminus of an antibody chain, including pyro-glutamic acid, is encompassed within the term "glutamine" as used herein. Accordingly, antibody chain sequences provided herein having N-terminal glutamine or glutamic acid residue encompass antibody chains regardless of the level of pyro-glutamic acid formation.

Unless otherwise indicated, an immunoglobulin may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. Immunoglobulins, e.g., human IgG1, exist in several allotypes, which differ from each other in at most a few amino acids. Unless otherwise indicated, "antibody" may include, by way of example, monoclonal and polyclonal antibodies; chimeric and humanized antibodies; human and non-human antibodies; wholly synthetic antibodies; and single chain antibodies.

The term "antigen-binding portion" or "antigen binding fragment" of an antibody, as used herein, refers to one or more fragments of an antibody that retain the ability to specifically bind to an antigen (e.g., human TIGIT). Examples of binding fragments encompassed within the term "antigen-binding portion/fragment" of an antibody include (i) a Fab fragment—a monovalent fragment consisting of the $V_L$, $V_H$, CL and CH1 domains; (ii) a F(ab')$_2$ fragment—a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, and (v) a dAb fragment (Ward et al., (1989) *Nature* 341:544-546) consisting of a $V_H$ domain. An isolated complementarity determining region (CDR), or a combination of two or more isolated CDRs joined by a synthetic linker, may comprise and antigen binding domain of an antibody if able to bind antigen.

Single chain antibody constructs are also included in the invention. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion/fragment" of an antibody. These and other potential constructs are described at Chan & Carter (2010) *Nat. Rev. Immunol.* 10:301. These antibody fragments are obtained using conventional techniques known to those with skill in the art, and the fragments are screened for utility in the same manner as are intact antibodies. Antigen-binding portions/fragments can be produced by recombinant DNA techniques, or by enzymatic or chemical cleavage of intact immunoglobulins.

Unless otherwise indicated, the word "fragment" when used with reference to an antibody, such as in a claim, refers to an antigen binding fragment of the antibody, such that "antibody or fragment" has the same meaning as "antibody or antigen binding fragment thereof."

A "bispecific" or "bifunctional antibody" is an artificial hybrid antibody having two different heavy/light chain pairs, giving rise to two antigen binding sites with specificity for different antigens. Bispecific antibodies can be produced by a variety of methods including fusion of hybridomas or linking of Fab' fragments. See, e.g., Songsivilai & Lachmann (1990) *Clin. Exp. Immunol.* 79:315; Kostelny et al. (1992) *J. Immunol.* 148:1547.

The term "monoclonal antibody," as used herein, refers to an antibody that displays a single binding specificity and affinity for a particular epitope or a composition of antibodies in which all antibodies display a single binding specificity and affinity for a particular epitope. Typically such monoclonal antibodies will be derived from a single cell or nucleic acid encoding the antibody, and will be propagated without intentionally introducing any sequence alterations. Accordingly, the term "human monoclonal antibody" refers to a monoclonal antibody that has variable and optional constant regions derived from human germline immunoglobulin sequences. In one embodiment, human monoclonal antibodies are produced by a hybridoma, for example, obtained by fusing a B cell obtained from a transgenic or transchromosomal non-human animal (e.g., a transgenic mouse having a genome comprising a human heavy chain transgene and a light chain transgene), to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations that occur, for example, during antibody maturation. As known in the art (see, e.g., Lonberg (2005) *Nature Biotech.* 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid sequences that encode the light chain and heavy chain immunoglobulin polypeptides in response to an antigen may not be identical to the original germline sequences, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. Human antibodies of the present invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies are used synonymously.

A "humanized" antibody refers to an antibody in which some, most or all of the amino acids outside the CDR domains of a non-human antibody, e.g. a mouse antibody, are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody. A "hybrid" antibody refers to an antibody having heavy and light chains of different types, such as a mouse (parental) heavy chain and a humanized light chain, or vice versa.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally occurring variants within a specific isotype group, which variants differ in one or a few amino acids. See, e.g., Jefferis et al. (2009) *mAbs* 1:1.

The phrases "an antibody recognizing an antigen" and "an antibody specific for an antigen" are used interchangeably herein with the term "an antibody that binds specifically to an antigen."

An "isolated antibody," as used herein, refers to an antibody that is substantially free of other antibodies having different antigenic specificities (e.g., an isolated antibody that specifically binds to TIGIT is substantially free of antibodies that specifically bind antigens other than TIGIT). An isolated antibody that specifically binds to an epitope of human TIGIT may, however, have cross-reactivity to other TIGIT proteins from different species.

As used herein, an antibody that "inhibits binding of PVR to TIGIT" refers to an antibody that inhibits the binding of human PVR to human TIGIT with an EC50 of about 1 µg/mL or less, such as about 0.9 µg/mL or less, about 0.85 µg/mL or less, about 0.8 µg/mL or less, about 0.75 µg/mL or less, about 0.7 µg/mL or less, about 0.65 µg/mL or less, about 0.6 µg/mL or less, about 0.55 µg/mL or less, about 0.5 µg/mL or less, about 0.45 µg/mL or less, about 0.4 µg/mL or less, about 0.35 µg/mL or less, about 0.3 µg/mL or less, about 0.25 µg/mL or less, about 0.2 µg/mL or less, about 0.15 µg/mL or less, or about 0.1 µg/mL or less, in art-recognized methods, e.g., in a FACS-based cell-binding assay.

"Effector functions," deriving from the interaction of an antibody Fc region with certain Fc receptors, include but are not necessarily limited to C1q binding, complement dependent cytotoxicity (CDC), Fc receptor binding, FcγR-mediated effector functions such as ADCC and antibody dependent cell-mediated phagocytosis (ADCP), and down regulation of a cell surface receptor (e.g., the B cell receptor; BCR). Such effector functions generally require the Fc region to be combined with an antigen binding domain (e.g., an antibody variable domain).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIb, or equivalently FcγRIIB) receptor. Various properties of human FcγRs are summarized in Table 1. The majority of innate effector cell types co-express one or more activating FcγR and the inhibitory FcγRIIb, whereas natural killer (NK) cells selectively express one activating Fc receptor (FcγRIII in mice and FcγRIIIA in humans) but not the inhibitory FcγRIIb in mice and humans. Human IgG1 binds to most human Fc receptors and is considered equivalent to murine IgG2a with respect to the types of activating Fc receptors that it binds to.

TABLE 1

Properties of Human FcγRs

| Fcγ | Allelic variants | Affinity for human IgG | Isotype preference | Cellular distribution |
|---|---|---|---|---|
| FcγRI | None described | High ($K_D$ ~10 nM) | IgG1 = 3 > 4 >> 2 | Monocytes, macrophages, activated neutrophils, dendritic cells? |
| FcγRIIA | H131 | Low to medium | IgG1 > 3 > 2 > 4 | Neutrophils, monocytes, |
|  | R131 | Low | IgG1 > 3 > 4 > 2 | macrophages, eosinophils, dendritic cells, platelets |
| FcγRIIIA | V158 | Medium | IgG1 = 3 >> 4 > 2 | NK cells, monocytes, |
|  | F158 | Low | IgG1 = 3 >> 4 > 2 | macrophages, mast cells, eosinophils, dendritic cells? |
| FcγRIIb | I232 | Low | IgG1 = 3 = 4 > 2 | B cells, monocytes, |
|  | T232 | Low | IgG1 = 3 = 4 > 2 | macrophages, dendritic cells, mast cells |

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (Clq) of the classical complement system. Thus, an Fc region comprises the constant region of an antibody excluding the first constant region immunoglobulin domain (e.g., CH1 or CL). In IgG, IgA and IgD antibody isotypes, the Fc region comprises CH2 and CH3 constant domains in each of the antibody's two heavy chains; IgM and IgE Fc regions comprise three heavy chain constant domains (CH domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 (or an amino acid between these two amino acids) to the carboxy-terminus of the heavy chain, wherein the numbering is according to the EU index as in Kabat. Kabat et al. (1991) *Sequences of Proteins of Immunological Interest*, National Institutes of Health, Bethesda, MD; see also FIGS. 3c-3f of U.S. Pat. App. Pub. No. 2008/0248028. The $C_{H2}$ domain of a human IgG Fc region extends from about amino acid 231 to about amino acid 340, whereas the $C_{H3}$ domain is positioned on C-terminal side of a $C_{H2}$ domain in an Fc region, i.e., it extends from about amino acid 341 to about amino acid 447 of an IgG (including a C-terminal lysine). As used herein, the Fc region may be a native sequence Fc, including any allotypic variant, or a variant Fc (e.g., a non-naturally occurring Fc). Fc may also refer to this region in isolation or in the context of an Fc-comprising protein polypeptide such as a "binding protein comprising an Fc region," also referred to as an "Fc fusion protein" (e.g., an antibody or immunoadhesin).

Unless otherwise indicated, or clear from the context, amino acid residue numbering in the Fc region of an antibody is according to the EU numbering convention, except when specifically referring to residues in a sequence in the Sequence Listing, in which case numbering is necessarily consecutive. For example, literature references regarding the effects of amino acid substitutions in the Fc region will typically use EU numbering, which allows for reference to any given residue in the Fc region of an antibody by the same number regardless of the length of the variable domain to which is it attached. In rare cases it may be necessary to refer to the document being referenced to confirm the precise Fc residue being referred to.

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof. Native sequence Fc include the various allotypes of Fcs. See, e.g., Jefferis et al. (2009) *mAbs* 1:1.

The term "epitope" or "antigenic determinant" refers to a site on an antigen (e.g., TIGIT) to which an immunoglobulin or antibody specifically binds. Epitopes within protein antigens can be formed both from contiguous amino acids (usually a linear epitope) or noncontiguous amino acids juxtaposed by tertiary folding of the protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation.

The term "epitope mapping" refers to the process of identification of the molecular determinants on the antigen involved in antibody-antigen recognition. Methods for determining what epitopes are bound by a given antibody are well known in the art and include, for example, immunoblotting and immunoprecipitation assays, wherein overlapping or contiguous peptides from (e.g., from TIGIT) are tested for reactivity with a given antibody (e.g., anti-TIGIT antibody); x-ray crystallography; 2-dimensional nuclear magnetic resonance; yeast display (see Example 4 herein); and HDX-MS (see, e.g., *Epitope Mapping Protocols in Methods in Molecular Biology*, Vol. 66, G. E. Morris, Ed. (1996)).

The term "binds to the same epitope" with reference to two or more antibodies means that the antibodies bind to the same segment of amino acid residues, as determined by a given method. Techniques for determining whether antibodies bind to the "same epitope on TIGIT" with the antibodies described herein include, for example, epitope mapping methods, such as, x-ray analyses of crystals of antigen:antibody complexes, which provides atomic resolution of the epitope, and hydrogen/deuterium exchange mass spectrometry (HDX-MS). Other methods monitor the binding of the antibody to antigen fragments (e.g. proteolytic fragments) or to mutated variations of the antigen where loss of binding due to a modification of an amino acid residue within the antigen sequence is often considered an indication of an epitope component, such as alanine scanning mutagenesis (Cunningham & Wells (1985) *Science* 244:1081) or yeast display of mutant target sequence variants (see Example 4 herein). In addition, computational combinatorial methods for epitope mapping can also be used. These methods rely on the ability of the antibody of interest to affinity isolate specific short peptides from combinatorial phage display peptide libraries. Antibodies having the same or closely related VH and VL or the same CDR sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competition assays can be conducted as described, for example, in Ed Harlow and David Lane, Cold Spring Harb. Protoc.; 2006; doi:10.1101/pdb.prot4277 or in Chapter 11 of "Using Antibodies" by Ed Harlow and David Lane, Cold Spring Harbor Laboratory Press, Cold Spring Harbor, NY, USA 1999. Competing antibodies bind to the same epitope, an overlapping epitope or to adjacent epitopes (e.g., as evidenced by steric hindrance).

Other competitive binding assays include: solid phase direct or indirect radioimmunoassay (RIA), solid phase direct or indirect enzyme immunoassay (EIA), sandwich competition assay (see Stahli et al. (1983) *Methods in Enzymology* 9:242); solid phase direct biotin-avidin EIA (see Kirkland et al. (1986) *J. Immunol.* 137:3614); solid phase direct labeled assay, solid phase direct labeled sandwich assay (see Harlow and Lane (1988), *Antibodies: A Laboratory Manual*, Cold Spring Harbor Press); solid phase direct label RIA using I-125 label (see Morel et al. (1988) *Mol. Immunol.* 25(1):7); solid phase direct biotin-avidin EIA (Cheung et al. (1990) *Virology* 176:546); and direct labeled RIA. (Moldenhauer et al. (1990) *Scand. J. Immunol.* 32:77).

As used herein, the terms "specific binding," "selective binding," "selectively binds," and "specifically binds," refer to antibody binding to an epitope on a predetermined antigen but not to other antigens. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE® 2000 surface plasmon resonance instrument using the predetermined antigen, e.g., recombinant human TIGIT, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Accordingly, an antibody that "specifically binds to human TIGIT" refers to an antibody that binds to soluble or cell bound human TIGIT with a $K_D$ of $10^{-7}$ M or less, such as approximately less than $10^{-8}$M, $10^{-9}$ M or $10^{-10}$ M or even lower. An antibody that "cross-reacts with cynomolgus TIGIT" refers to an antibody that binds to cynomolgus TIGIT with a $K_D$ of $10^{-7}$ M or less, such as approximately less than $10^{-8}$M, $10^{-9}$ M or $10^{-10}$ M or even lower.

The term "$k_{assoc}$" or "$k_a$", as used herein, refers to the association rate constant of a particular antibody-antigen interaction, whereas the term "$k_{dis}$" or "$k_d$," as used herein, refers to the dissociation rate constant of a particular antibody-antigen interaction. The term "$K_D$", as used herein, refers to the equilibrium dissociation constant, which is obtained from the ratio of $k_d$ to $k_a$ (i.e., $k_d/k_a$) and is expressed as a molar concentration (M). $K_D$ values for antibodies can be determined using methods well established in the art. Preferred methods for determining the $K_D$ of an antibody include biolayer interferometry (BLI) analysis, preferably using a Fortebio Octet RED device, surface plasmon resonance, preferably using a biosensor system such as a BIACORE® surface plasmon resonance system (see e.g. Example 2), or flow cytometry and Scatchard analysis.

As used herein, the term "high affinity" for an IgG antibody refers to an antibody having a $K_D$ of $10^{-8}$M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$ M or less.

The term "EC50" in the context of an in vitro or in vivo assay using an antibody or antigen binding fragment thereof, refers to the concentration of an antibody or an antigen-binding fragment thereof that induces a response that is 50% of the maximal response, i.e., halfway between the maximal response and the baseline.

The term "binds to immobilized TIGIT" refers to the ability of an antibody described herein to bind to TIGIT, for example, expressed on the surface of a cell or attached to a solid support.

The term "cross-reacts," as used herein, refers to the ability of an antibody described herein to bind to TIGIT from a different species. For example, an antibody described herein that binds human TIGIT may also bind TIGIT from another species (e.g., cynomolgus TIGIT). As used herein, cross-reactivity may be measured by detecting a specific reactivity with purified antigen in binding assays (e.g., SPR, ELISA) or binding to, or otherwise functionally interacting with, cells physiologically expressing TIGIT. Methods for determining cross-reactivity include standard binding assays as described herein, for example, by BIACORE® surface plasmon resonance (SPR) analysis using a BIACORE® 2000 SPR instrument (Biacore AB, Uppsala, Sweden), or flow cytometric techniques.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein may contain a modification such as, but not limited to, glycosylation, phosphorylation or a disulfide bond. A "protein" may comprise one or more polypeptides.

The term "nucleic acid molecule," as used herein, is intended to include DNA molecules and RNA molecules. A nucleic acid molecule may be single-stranded or double-stranded, and may be cDNA.

Also provided are "conservative sequence modifications" to the antibody sequence provided herein, i.e. nucleotide and amino acid sequence modifications that do not abrogate the binding of the antibody encoded by the nucleotide sequence or containing the amino acid sequence, to the antigen. For example, modifications can be introduced by standard techniques known in the art, such as site-directed mutagenesis and PCR-mediated mutagenesis. Conservative sequence modifications include conservative amino acid substitutions, in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-TIGIT antibody is preferably replaced with another amino acid residue from the same side chain family. Methods of identifying nucleotide and amino acid conservative substitutions that do not eliminate antigen binding are well-known in the art. See, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997)).

Alternatively, in another embodiment, mutations can be introduced randomly along all or part of an anti-TIGIT antibody coding sequence, such as by saturation mutagenesis, and the resulting modified anti-TIGIT antibodies can be screened for improved binding activity.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids.

The percent identity between two sequences is a function of the number of identical positions shared by the sequences when the sequences are optimally aligned (i.e., % homology=#of identical positions/total #of positions×100), with optimal alignment determined taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package, using a NWSgapdna. CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the) (BLAST program, score=50, wordlength=3 to obtain amino acid sequences homologous to the protein molecules described herein. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and may be a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

An "immune response" refers to a biological response within a vertebrate against foreign agents, which response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell or a Th cell, such as a $CD8^+$ or $CD4^+$ T cell, or the inhibition or depletion of a $T_{reg}$ cell. "T effector" ("$T_{eff}$") cells refers to T cells (e.g., $CD4^+$ and $CD8^+$ T cells) with cytolytic activities as well as T helper (Th) cells, which secrete cytokines and activate and direct other immune cells, but does not include regulatory T cells ($T_{reg}$ cells).

As used herein, the term "T cell-mediated response" refers to a response mediated by T cells, including effector T cells (e.g., $CD8^+$ cells) and helper T cells (e.g., $CD4^+$ cells). T cell mediated responses include, for example, T cell cytotoxicity and proliferation.

As used herein, the term "cytotoxic T lymphocyte (CTL) response" refers to an immune response induced by cytotoxic T cells. CTL responses are mediated primarily by $CD8^+$ T cells.

An "immunomodulator" or "immunoregulator" refers to an agent, e.g., a component of a signaling pathway, that may be involved in modulating, regulating, or modifying an immune response. "Modulating," "regulating," or "modifying" an immune response refers to any alteration in a cell of the immune system or in the activity of such cell (e.g., an effector T cell). Such modulation includes stimulation or suppression of the immune system, which may be manifested by an increase or decrease in the number of various cell types, an increase or decrease in the activity of these cells, or any other changes that can occur within the immune system. Both inhibitory and stimulatory immunomodulators have been identified, some of which may have enhanced function in a tumor microenvironment. In preferred embodiments, the immunomodulator is located on the surface of a T cell. An "immunomodulatory target" or "immunoregulatory target" is an immunomodulator that is targeted for binding by, and whose activity is altered by the binding of, a substance, agent, moiety, compound or molecule. Immunomodulatory targets include, for example, receptors on the surface of a cell ("immunomodulatory receptors") and receptor ligands ("immunomodulatory ligands").

"Immunotherapy" refers to the treatment of a subject afflicted with, or at risk of contracting or suffering a recurrence of, a disease by a method comprising inducing, enhancing, suppressing or otherwise modifying an immune response.

"Immunostimulating therapy" or "immunostimulatory therapy" refers to a therapy that results in increasing (inducing or enhancing) an immune response in a subject for, e.g., treating cancer.

"Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, "administering" refers to the physical introduction of a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, the terms "inhibits" or "blocks" (e.g., referring to inhibition/blocking of binding of PVR to TIGIT on cells) are used interchangeably and encompass both partial and complete inhibition/blocking by, for example, at least about 50%, 60%, 70%, 80%, 90%, 95%, 99%, or 100%.

As used herein, "cancer" refers a broad group of diseases characterized by the uncontrolled growth of abnormal cells in the body. Unregulated cell division may result in the formation of malignant tumors or cells that invade neighboring tissues and may metastasize to distant parts of the body through the lymphatic system or bloodstream.

A "hematological malignancy" includes a lymphoma, leukemia, myeloma or a lymphoid malignancy, as well as a cancer of the spleen and the lymph nodes. Exemplary lymphomas include both B cell lymphomas and T cell lymphomas. B-cell lymphomas include both Hodgkin's lymphomas and most non-Hodgkin's lymphomas. Non-limiting examples of B cell lymphomas include diffuse large B-cell lymphoma, follicular lymphoma, mucosa-associated lymphatic tissue lymphoma, small cell lymphocytic lymphoma (overlaps with chronic lymphocytic leukemia), mantle cell lymphoma (MCL), Burkitt's lymphoma, mediastinal large B cell lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis. Non-limiting examples of T cell lymphomas include extranodal T cell lymphoma, cutaneous T cell lymphomas, anaplastic large cell lymphoma, and angioimmunoblastic T cell lymphoma. Hematological malignancies also include leukemia, such as, but not limited to, secondary leukemia, chronic lymphocytic leukemia, acute myelogenous leukemia, chronic myelogenous leukemia, and acute lymphoblastic leukemia. Hematological malignancies further include myelomas, such as, but not limited to, multiple myeloma and smoldering multiple myeloma. Other hematological and/or B cell- or T-cell-associated cancers are encompassed by the term hematological malignancy.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Prophylaxis refers to administration to a subject who does not have a disease, to prevent the disease from occurring or minimize its effects if it does.

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A "prophylactically effective amount" or a "prophylactically effective dosage" of a drug is an amount of the drug that, when administered alone or in combination with another therapeutic agent to a subject at risk of developing a disease or of suffering a recurrence of disease, inhibits the development or recurrence of the disease. The ability of a therapeutic or prophylactic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

By way of example, an anti-cancer agent is a drug that slows cancer progression or promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms in the patient. Pharmacological effectiveness refers to the ability of the drug to promote cancer regression in the patient. Physiological safety refers to an acceptably low level of toxicity, or other adverse physiological effects at the cellular, organ and/or organism level (adverse effects) resulting from administration of the drug.

By way of example for the treatment of tumors, a therapeutically effective amount or dosage of the drug preferably inhibits cell growth or tumor growth by at least about 20%, more preferably by at least about 40%, even more preferably by at least about 60%, and still more preferably by at least about 80% relative to untreated subjects. In the most preferred embodiments, a therapeutically effective amount or dosage of the drug completely inhibits cell growth or tumor growth, i.e., preferably inhibits cell growth or tumor growth by 100%. The ability of a compound to inhibit tumor growth can be evaluated using the assays described infra. Inhibition of tumor growth may not be immediate after treatment, and may only occur after a period of time or after repeated administration. Alternatively, this property of a composition can be evaluated by examining the ability of the compound to inhibit cell growth, such inhibition can be measured in vitro by assays known to the skilled practitioner. In other preferred embodiments described herein, tumor regression may be observed and may continue for a period of at least about 20 days, more preferably at least about 40 days, or even more preferably at least about 60 days.

"Combination" therapy, as used herein, unless otherwise clear from the context, is meant to encompass administration of two or more therapeutic agents in a coordinated fashion, and includes, but is not limited to, concurrent dosing. Specifically, combination therapy encompasses both co-administration (e.g. administration of a co-formulation or simultaneous administration of separate therapeutic compositions) and serial or sequential administration, provided that administration of one therapeutic agent is conditioned in some way on administration of another therapeutic agent. For example, one therapeutic agent may be administered only after a different therapeutic agent has been administered and allowed to act for a prescribed period of time. See, e.g., Kohrt et al. (2011) *Blood* 117:2423.

The terms "patient" and "subject" refer to any human or non-human animal that receives either prophylactic or therapeutic treatment. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc.

Various aspects described herein are described in further detail in the following subsections.

I. Anti-TIGIT Antibodies

The present application discloses fully human anti-huTIGIT antibodies having desirable properties for use as therapeutic agents in treating diseases such as cancers. These properties include one or more of the ability to bind to human TIGIT with high affinity, the ability to bind to cynomolgus monkey TIGIT, the ability to block PVR binding (and thus signaling), and the absence of sequence liabilities that might reduce the chemical stability of the antibody.

Figure 2A:
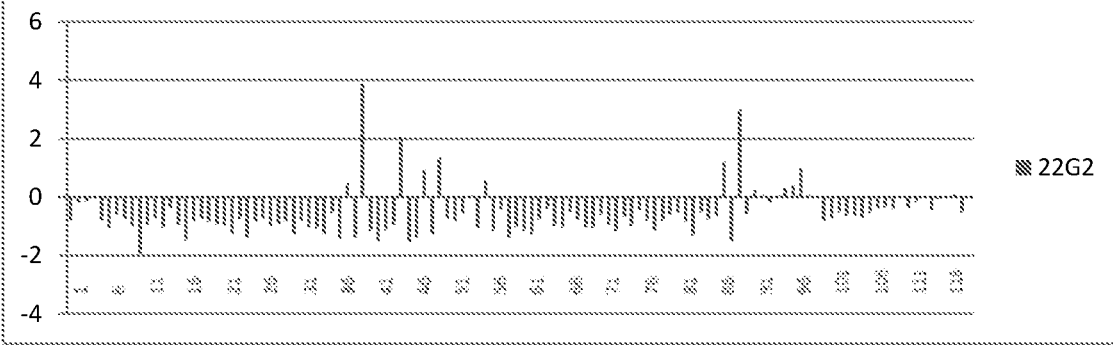
FIGS. 2A, 2B, and 2C show yeast display data for binding of huTIGIT sequence variants to antibodies 22G2, 11G11, and 15A6, respectively. The residue numbers for each amino acid residue in mature huTIGIT are presented along the abscissa. Residue numbers are 21 lower than the numbering for SEQ ID NO: 1 because the sequence listing includes the signal peptide, which is not included in the figures. As detailed in Example 4, yeast displaying sequence variants of huTIGIT were selected based on their inability to bind to the respective antibodies (22G2, 11G11, 15A6). Accordingly, positions along the huTIGIT sequence that are critical to antibody binding appear at high frequency (i.e. as bars/lines rising above the ordinate) due to their over-representation in the pool of non-binding yeast clones. The frequencies at which variant (non-wild type) residues appear at each residue are represented (on a logarithmic scale) on the ordinate, with one bar (line) or each residue. Frequency data are normalized to the frequencies at which variant residues appear at each position in an unselected library, i.e. libraries that had not been subjected to selection based on the inability to bind to the anti-huTIGIT antibodies of the present invention. See Example 4.
Figure 2B:
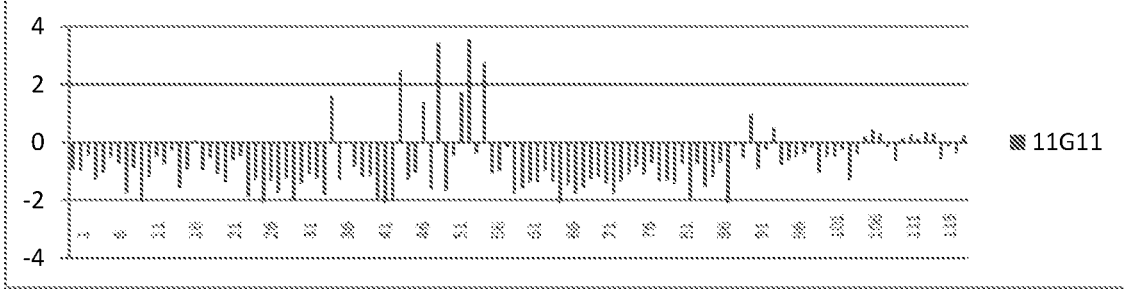
Figure 2C:
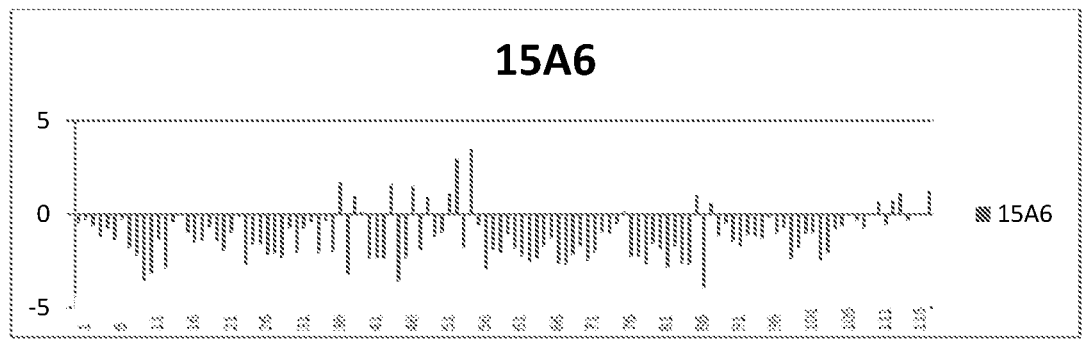
Figure 3:
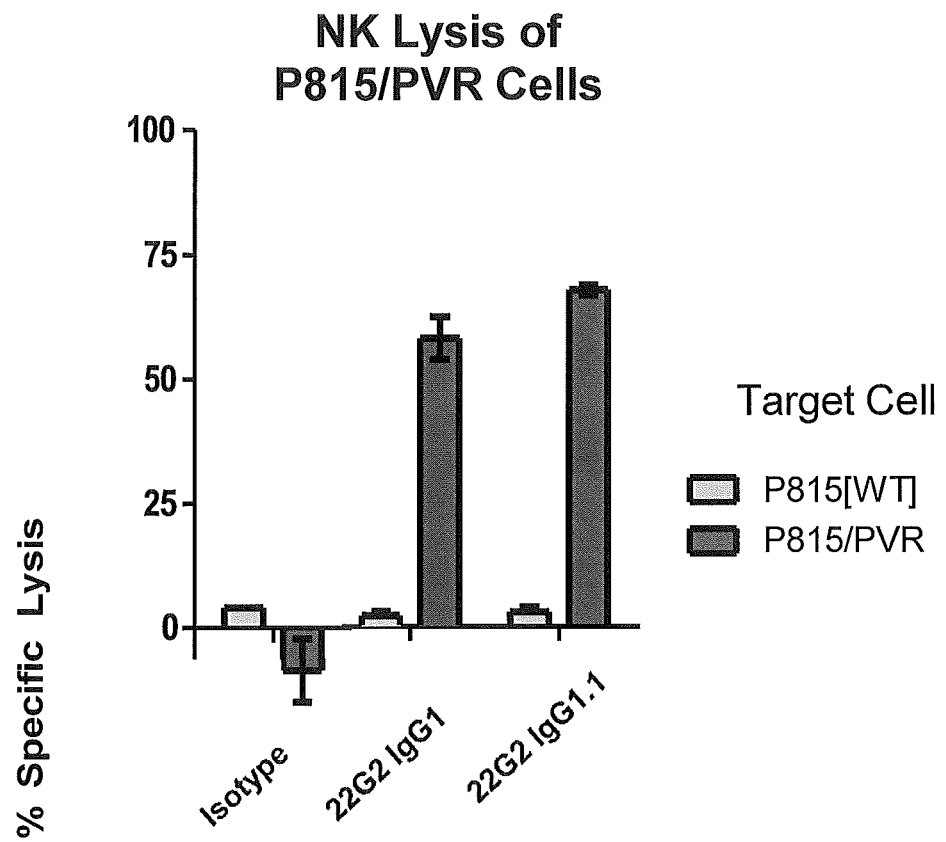
FIG. 3 shows the effect of anti-TIGIT mAb 22G2 on lysis, expressed as percent specific lysis of cells expressing human PVR by human NK cells. See Example 5. For each antibody, the left bar is wildtype P815 cells and the right bar is P815 cells expressing human PVR.
Figure 4A:
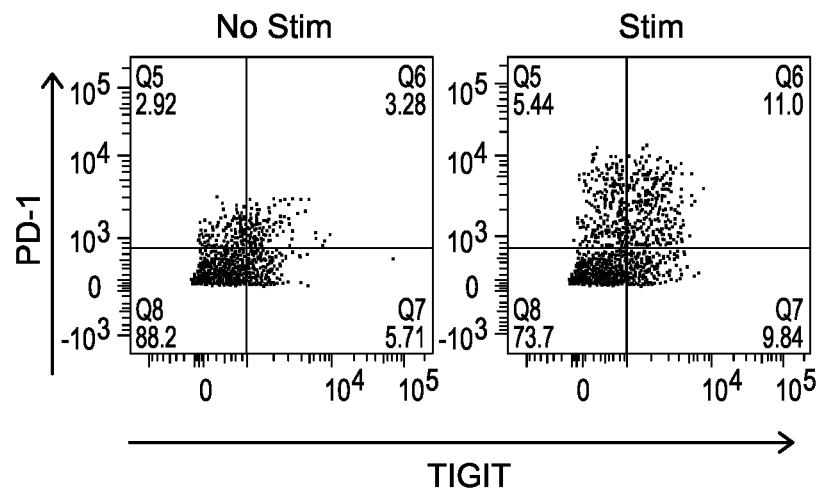
FIG. 4A shows that treatment of healthy human donor blood with a cocktail of antigenic peptides (CETF=peptides from CMV, EBV, influenza and tetanus) induces upregulation of PD-1 and TIGIT on $CD8^+$ T cells. The "No Stim" sample was not treated with CEFT, whereas the "Stim" sample was.
Figure 4B:
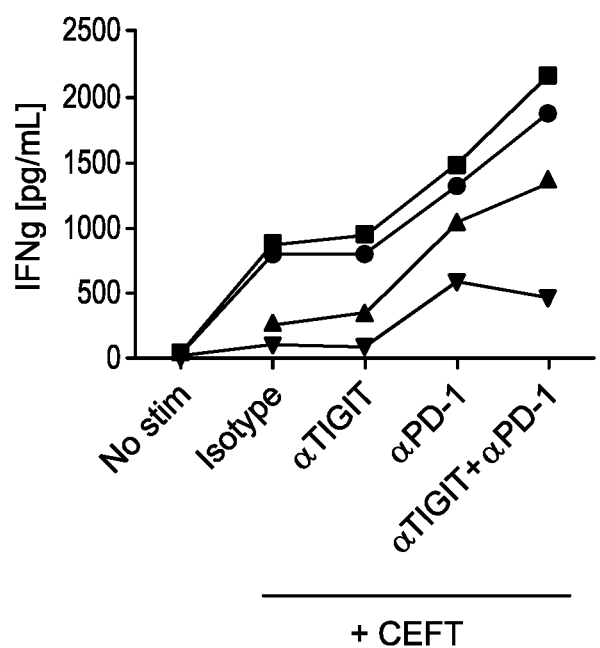
FIG. 4B shows the effect of anti-TIGIT mAb and/or anti-PD-1 mAb on IFNγ expression from four healthy human donor blood samples stimulated with CETF. See Example 6.

The anti-TIGIT antibodies disclosed herein by sequence bind to specific epitopes on human TIGIT determined as described in Example 4 and shown in FIGS. 2A-2C. The three specific antibodies for which epitopes were determined bind at similar regions of human TIGIT but differ in which specific amino acid residues are contacted. The antibodies share the properties of binding to human TIGIT with high affinity and having the ability to block PVR binding. Accordingly, other antibodies that bind to the same or closely related epitopes would likely share these desirable properties, and may be discovered by competition experiments.

In addition, antibody 22G2 binds to cynomolgus monkey TIGIT with substantially the same affinity as it binds to human TIGIT, which is convenient when it is necessary to perform toxicity studies in support of regulatory approval for use of the antibody as a human therapeutic. Other anti-TIGIT antibodies that bind to the same or similar epitopes as 15A6 and 22G2 are likely to share this advantageous property of binding to cyno TIGIT. Antibodies binding to similar epitopes can be discovered by doing competition experiments or by determining their epitopes directly.

Anti-TIGIT Antibodies that Compete with Anti-huTIGIT Antibodies Disclosed Herein Anti-huTIGIT antibodies that compete with the antibodies of the present invention for binding to huTIGIT, such as 15A6 and 22G2, may be raised using immunization protocols similar to those described herein (Example 1). Antibodies that compete for binding with the anti-huTIGIT antibodies described herein may also be generated immunizing mice may with human TIGIT or a construct comprising the extracellular domain thereof (residues 22-141 of SEQ ID NO: 1; NP_776160.2), or by immunizing with a fragment of human TIGIT containing the epitope bound by the anti-huTIGIT antibodies disclosed herein (e.g. 15A6, 22G2 and 11G11). The resulting antibodies can be screened for the ability to block binding of 15A6 or 22G2 to human TIGIT by methods well known in the art, for example blocking binding to fusion protein of the extracellular domain of TIGIT and an immunoglobulin Fc domain in a ELISA, or blocking the ability to bind to cells expressing huTIGIT on their surface, e.g. by FACS. In various embodiments, the test antibody is contacted with the TIGIT-Fc fusion protein (or to cells expressing huTIGIT on their surface) prior to, at the same time as, or after the addition of 15A6 or 22G2. For example, "binning" experiments may be performed (Example 3) to determine whether an antibody falls into the same "bin" as antibodies 15A6 or 22G2, in which experiments antibodies 15A6 or 22G2 are referred to as the "reference" antibodies, and the antibodies to be tested are referred to as the "test" antibodies. Antibodies that reduce binding of 15A6 and/or 22G2 to TIGIT (either as an Fc fusion or on a cell), particularly at roughly stoichiometric concentrations, are likely to bind at the same, overlapping, or adjacent epitopes, and thus may share the desirable functional properties of 15A6 and 22G2.

Competing antibodies can also be identified using other methods known in the art. For example, standard ELISA assays or competitive ELISA assays can be used in which a recombinant human TIGIT protein construct is immobilized on the plate, various concentrations of unlabeled test antibody are added, the plate is washed, labeled reference antibody is added, washed, and the amount of bound label is measured. If the increasing concentration of the unlabeled test antibody inhibits the binding of the labeled reference antibody, the test antibody is said to inhibit the binding of the reference antibody to the target on the plate, or is said to compete with the binding of the reference antibody. Additionally or alternatively, BIACORE® SPR analysis can be used to assess the ability of the antibodies to compete. The ability of a test antibody to inhibit the binding of an anti-huTIGIT antibody described herein to TIGIT demonstrates that the test antibody can compete with the reference antibody for binding to TIGIT.

Accordingly, provided herein are anti-TIGIT antibodies that inhibit the binding of an anti-huTIGIT antibodies described herein to TIGIT on cells, e.g., activated T cells, by at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or by 100% and/or whose binding to TIGIT on cells, e.g., activated T cells, is inhibited by at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or by 100%, e.g., as measured by ELISA or FACS, such as by using the assay described in the following paragraph.

An exemplary competition experiment to determine whether a test antibody blocks the binding of (i.e., "competes with") a reference antibody, may be conducted as follows: activated human T cells are prepared as follows: Peripheral Blood Mononuclear Cells (PBMCs) are isolated from human whole blood using Ficoll gradient and activated with 10 μg/mL phytohaemagglutinin (PHA-L) (USBiol #P3370-30) and 200 IU/mL recombinant IL-2 (Peprotech #200-02) for 3 days. The activated T cells are resuspended in FACS buffer (PBS with 5% Fetal Bovine Serum) and seeded at $10^5$ cells per sample well in a 96 well plate. Unconjugated test antibody is added to the plate at concentrations ranging from 0 to 50 μg/mL (three-fold titration starting from a highest concentration of 50 μg/mL). An unrelated IgG may be used as an isotype control for the test antibody and added at the same concentrations (three-fold titration starting from a highest concentration of 50 μg/mL). A sample pre-incubated with 50 μg/mL unlabeled reference antibody may be included as a positive control for complete blocking (100% inhibition) and a sample without antibody in the primary incubation may be used as a negative control (no competition; 0% inhibition). After 30 minutes of incubation, labeled, e.g., biotinylated, reference antibody is added at a concentration of 2 μg/mL per well without washing. Samples are incubated for another 30 minutes. Unbound antibodies are removed by washing the cells with FACS buffer. Cell-bound labeled reference antibody is detected with an agent that detects the label, e.g., PE conjugated streptavidin (Invitrogen, catalog #521388) for detecting biotin. The samples are acquired on a FACS Calibur Flow Cytometer (BD, San Jose) and analyzed with Flowjo software (Tree Star, Inc, Ashland, OR). The results may be represented as the % inhibition (i.e., subtracting from 100% the amount of label at each concentration divided by the amount of label obtained with no blocking antibody).

Typically, the same experiment is then conducted in the reverse, i.e., the test antibody is the reference antibody and the reference antibody is the test antibody. In certain embodiments, an antibody at least partially (e.g., at least 10%, 20%, 30%, 40%, 50%, 60%, 70%, 80%, or 90%) or completely (100%) blocks the binding of the other antibody to the target, e.g. human TIGIT or fragment thereof, and regardless of whether inhibition occurs when one or the other antibody is the test antibody. A test and a reference antibody "cross-block" binding of each other to the target when the antibodies compete with each other both ways, i.e., in competition experiments in which the test antibody is added first and in competition experiments in which the reference antibody is added first.

Anti-huTIGIT antibodies are considered to compete with the anti-huTIGIT antibodies disclosed herein if they inhibit binding of 15A6 and/or 22G2 to human TIGIT by at least 10%, 20%, 30%, 40%, 50%, 60%, 70%, 80%, 90% or by 100% when present at roughly equal concentrations, for example in competition experiments like those described in Example 3. Unless indicated otherwise, an antibody will be considered to compete with an antibody selected from the group consisting of the anti-huTIGIT antibodies of the present invention if it reduces binding of the selected antibody to human TIGIT by at least 20% when used at a roughly equal molar concentration with the selected antibody, as measured in competition ELISA experiments as outlined in the preceding two paragraphs.

Anti-TIGIT Antibodies that Bind to the Same Epitope

Anti-huTIGIT antibodies that bind to the same or similar epitopes to the antibodies disclosed herein may be raised using immunization protocols similar to those described herein (Example 1). The resulting antibodies can be screened for high affinity binding to human TIGIT (Example 2). Selected antibodies can then be studied in yeast display assay in which sequence variants of huTIGIT are presented on the surface of yeast cells (Example 4) to determine the precise epitope bound by the antibody.

Epitope determinations may be made by any method known in the art. The epitopes disclosed herein were determined by yeast display, as described at Example 4 and presented at FIGS. 2A-2C. In various embodiments, anti-huTIGIT antibodies are considered to bind to the same epitope as an anti-huTIGIT mAb disclosed herein, e.g. 15A6 and/or 22G2, if they make contact with one or more of the same residues within at least one region of huTIGIT contacted by 15A6 or 22G2; if they make contacts with a majority of the residues within at least one region of huTIGIT contacted by 15A6 or 22G2; if they make contacts with a majority of the residues within each region of huTIGIT contacted by 15A6 or 22G2; if they make contact with a majority of contacts along the entire length of huTIGIT contacted by 15A6 or 22G2; if they make contacts within all of the distinct regions of human TIGIT contacted by 15A6 or 22G2; if they make contact with all of the same residues at any one region on human TIGIT contacted by 15A6 or 22G2; or if they make contact with all residues at all regions contacted by contacted by 15A6 or 22G2. Epitope "regions" are clusters of residues along the primary sequence that are contacted by antibodies 15A6 or 22G2, e.g. as provided at SEQ ID NOs: 38-44.

Techniques for determining antibodies that bind to the "same epitope on TIGIT" with the antibodies described herein include x-ray analyses of crystals of antigen:antibody complexes, which provides atomic resolution of the epitope. Other methods monitor the binding of the antibody to antigen fragments or mutated variations of the antigen where loss of binding due to a modification of an amino acid residue within the antigen sequence is considered an indication of an epitope component. Methods may also rely on the ability of an antibody of interest to affinity isolate specific short peptides (either in native three dimensional form or in denatured form) from combinatorial phage display peptide libraries, or from a protease digest of the target protein. The peptides are then regarded as leads for the definition of the epitope corresponding to the antibody used to screen the peptide library. For epitope mapping, computational algorithms have also been developed that have been shown to map conformational discontinuous epitopes.

The epitope or region comprising the epitope can also be identified by screening for binding to a series of overlapping peptides spanning TIGIT. Alternatively, the method of Jespers et al. (1994) *Biotechnology* 12:899 may be used to guide the selection of antibodies having the same epitope and therefore similar properties to the an anti-TIGIT antibodies described herein. Using phage display, first the heavy chain of the anti-TIGIT antibody is paired with a repertoire of (preferably human) light chains to select a TIGIT-binding antibody, and then the new light chain is paired with a repertoire of (preferably human) heavy chains to select a (preferably human) TIGIT-binding antibody having the same epitope or epitope region as an anti-huTIGIT antibody described herein. Alternatively variants of an antibody described herein can be obtained by mutagenesis of cDNA encoding the heavy and light chains of the antibody.

Alanine scanning mutagenesis, as described by Cunningham & Wells (1989) *Science* 244: 1081, or some other form of point mutagenesis of amino acid residues in TIGIT (such as the yeast display method provided at Example 4) may also be used to determine the functional epitope for an anti-TIGIT antibody.

The epitope or epitope region (an "epitope region" is a region comprising the epitope or overlapping with the epitope) bound by a specific antibody may also be determined by assessing binding of the antibody to peptides comprising fragments of TIGIT. A series of overlapping peptides encompassing the sequence of TIGIT (e.g., human TIGIT) may be synthesized and screened for binding, e.g. in a direct ELISA, a competitive ELISA (where the peptide is assessed for its ability to prevent binding of an antibody to TIGIT bound to a well of a microtiter plate), or on a chip. Such peptide screening methods may not be capable of detecting some discontinuous functional epitopes, i.e. functional epitopes that involve amino acid residues that are not contiguous along the primary sequence of the TIGIT polypeptide chain.

An epitope may also be identified by MS-based protein footprinting, such as hydrogen/deuterium exchange mass spectrometry (HDX-MS) and Fast Photochemical Oxidation of Proteins (FPOP). HDX-MS may be conducted, e.g., as further described at Wei et al. (2014) *Drug Discovery Today* 19:95, the methods of which are specifically incorporated by reference herein. FPOP may be conducted as described, e.g., in Hambley & Gross (2005) *J. American Soc. Mass Spectrometry* 16:2057, the methods of which are specifically incorporated by reference herein.

The epitope bound by anti-TIGIT antibodies may also be determined by structural methods, such as X-ray crystal structure determination (e.g., WO2005/044853), molecular modeling and nuclear magnetic resonance (NMR) spectroscopy, including NMR determination of the H-D exchange rates of labile amide hydrogens in TIGIT when free and when bound in a complex with an antibody of interest (Zinn-Justin et al. (1992) *Biochemistry* 31:11335; Zinn-Justin et al. (1993) *Biochemistry* 32:6884).

With regard to X-ray crystallography, crystallization may be accomplished using any of the known methods in the art (e.g. Giege et al. (1994) *Acta Crystallogr.* D50:339; McPherson (1990) *Eur. J. Biochem.* 189:1), including microbatch (e.g. Chayen (1997) *Structure* 5:1269), hanging-drop vapor diffusion (e.g. McPherson (1976) *J. Biol. Chem.* 251:6300), seeding and dialysis. It is desirable to use a protein preparation having a concentration of at least about 1 mg/mL and preferably about 10 mg/mL to about 20 mg/mL. Crystallization may be best achieved in a precipitant solution containing polyethylene glycol 1000-20,000 (PEG; average molecular weight ranging from about 1000 to about 20,000 Da), preferably about 5000 to about 7000 Da, more preferably about 6000 Da, with concentrations ranging from about 10% to about 30% (w/v). It may also be desirable to include a protein stabilizing agent, e.g. glycerol at a concentration ranging from about 0.5% to about 20%. A suitable salt, such as sodium chloride, lithium chloride or sodium citrate may also be desirable in the precipitant solution, preferably in a concentration ranging from about 1 mM to about 1000 mM. The precipitant is preferably buffered to a pH of from about 3.0 to about 5.0, preferably about 4.0. Specific buffers useful in the precipitant solution may vary and are well-known in the art (Scopes, Protein Purification: Principles and Practice, Third ed., (1994) Springer-Verlag, New York). Examples of useful buffers include, but are not limited to, HEPES, Tris, MES and acetate. Crystals may be grow at a wide range of temperatures, including 2° C., 4° C., 8° C. and 26° C.

Antibody:antigen crystals may be studied using well-known X-ray diffraction techniques and may be refined using computer software such as X-PLOR (Yale University, 1992, distributed by Molecular Simulations, Inc.; see e.g. Blundell & Johnson (1985) *Meth. Enzymol.* 114 & 115, H. W. Wyckoff et al., eds., Academic Press; U.S. Patent Application Publication No. 2004/0014194), and BUSTER (Bricogne (1993) Acta Cryst. D49:37-60; Bricogne (1997) *Meth. Enzymol.* 276A:361-423, Carter & Sweet, eds.; Roversi et al. (2000) *Acta Cryst. D*56:1313-1323), the disclosures of which are hereby incorporated by reference in their entireties.

Anti-TIGIT Antibodies that Bind with High Affinity

In some embodiments the anti-huTIGIT antibodies of the present invention bind to huTIGIT with high affinity, like the anti-huTIGIT antibodies disclosed herein, increasing their likelihood of being effective therapeutic agents. In various embodiments anti-huTIGIT antibodies of the present invention bind to huTIGIT with a $K_D$ of less than 10 nM, 5 nM, 2 nM, 1 nM, 300 pM, 100 pM or 60 pM. In other embodiments, the anti-huTIGIT antibodies of the present invention bind to huTIGIT with a $K_D$ between 2 nM and 60 pM. Standard assays to evaluate the binding ability of the antibodies toward huTIGIT include ELISAs, RIAs, Western blots, biolayer interferometry (BLI) and BIACORE® SPR analysis (see Example 2).

Anti-TIGIT Antibody Sequence Variants

Some variability in the antibody sequences disclosed herein may be tolerated and still maintain the desirable properties of the antibody. The CDR regions are delineated using the Kabat system (Kabat, E. A., et al. (1991) Sequences of Proteins of Immunological Interest, Fifth Edition, U.S. Department of Health and Human Services, NIH Publication No. 91-3242). Accordingly, the present invention further provides anti-huTIGIT antibodies comprising CDR sequences that are at least 70%, 75%, 80%, 85%, 90%, 95%, 96%, 97%, 98%, or 99% identical to the CDR sequences of the antibodies disclosed herein (e.g. 15A6, 22G2 and 11G11). The present invention also provides anti-huTIGIT antibodies comprising heavy and/or light chain variable domain sequences that are at least 70%, 75%, 80%, 85%, 90%, 95%, 96%, 97%, 98%, or 99% identical to the heavy and/or light chain variable domain sequences of the antibodies disclosed herein (e.g. 15A6, 22G2 and 11G11).

Anti-TIGIT Antibodies Derived from the Same Germlines

Given that antigen-binding specificity is determined primarily by the CDRs, antibodies sharing CDRs sequences with antibodies disclosed herein (e.g. 15A6, 22G2 and 11G11) are likely to share their desirable properties. In addition, selected antibodies disclosed herein (15A6, 22G2 and 11G11) bind to similar regions along the primary sequence of huTIGIT, and some heavy and light chains are derived from the same germline sequences. Accordingly, antibodies combining ("mixing and matching") CDR regions from antibodies with 15A6, 22G2 and 11G11 might also be expected to bind to huTIGIT and retain desirable properties thereof "Mixed and matched" antibodies having binding affinity, bioactivity and/or other properties equivalent or superior to the specific antibodies disclosed herein may be selected for use in the methods of the present invention.

In certain embodiments, anti-huTIGIT antibodies of the present invention comprises a heavy chain variable region derived from a particular human germline heavy chain immunoglobulin gene and/or a light chain variable region from a particular human germline light chain immunoglobulin gene. Antibody 15A6 has a heavy chain derived from human germlines V4-39, D6-19 and JH4b, and light chain germlines VA27 and JK2. Antibody 22G2 has a heavy chain derived from human germlines V4-61, D3-10 and JH6b, and light chain germlines VL6 and JK3. Antibody 11G11 has a heavy chain derived from human germlines V4-39, D3-10 and JH4b, and light chain germlines VL6 and JK2. Antibody 10D7 has a heavy chain derived from human germlines V1-69, D6-13 and JH6b, and light chain germlines VL15 and JK5. Other antibodies that bind to human TIGIT and derived from some or all of these germline sequences are likely to be closely related in sequence, particularly those derived from the same V-region genes, and thus would be expected to share the same desirable properties.

As used herein, a human antibody comprises heavy or light chain variable regions that are "derived from" a particular germline sequence if the variable regions of the antibody are obtained from a system that uses human germline immunoglobulin genes, and the antibody sequence is sufficiently related to the germline that it is more likely derived from the given germline than from any other. Such systems include immunizing a transgenic mouse carrying human immunoglobulin genes with the antigen of interest or screening a human immunoglobulin gene library displayed on phage with the antigen of interest. The human germline immunoglobulin sequence(s) from which the sequence of an antibody is "derived" can be identified by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "derived from" a particular human germline immunoglobulin sequence may contain amino acid differences as compared to the germline sequence due to, for example, naturally-occurring somatic mutations or intentional introduction of site-directed mutation. However, a selected human antibody typically is at least 90% identical in amino acids sequence to an amino acid sequence encoded by a human germline immunoglobulin gene (e.g. V regions) and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene (e.g. V regions). Typically, a human antibody derived from a particular human germline sequence will display no more than 10 amino acid differences from the amino acid sequence encoded by the human germline immunoglobulin gene (e.g. V regions). In certain cases, the human antibody may display no more than 5, or even no more than 4, 3, 2, or 1 amino acid difference from the amino acid sequence encoded by the germline immunoglobulin gene (e.g. V regions).

II. Engineered and Modified Antibodies VH and VL Regions

Also provided are engineered and modified antibodies that can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Such grafting is of particular use in humanizing non-human anti-TIGIT antibodies that compete for binding with the anti-huTIGIT antibodies disclosed herein and/or bind to the same epitope as the anti-huTIGIT antibodies disclosed herein. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific reference antibodies by constructing expression vectors that include CDR sequences from the specific reference antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.)

Such framework sequences can be obtained from public DNA databases or published references that include germline antibody gene sequences. For example, germline DNA sequences for human heavy and light chain variable region genes can be found in the "VBase" human germline sequence database, as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" J. Mol. Biol. 227:776-798; and Cox, J. P. L. et al. (1994) "A Directory of Human Germ-line $V_H$ Segments Reveals a Strong Bias in their Usage" Eur. J. Immunol. 24:827-836; the contents of each of which are expressly incorporated herein by reference.

Preferred framework sequences for use in the antibodies described herein are those that are structurally similar to the framework sequences used by antibodies described herein. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain up to 20, preferably conservative, amino acid substitutions as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Engineered antibodies described herein include those in which modifications have been made to framework residues within $V_H$ and/or $V_L$, e.g. to improve the properties of the antibody. Often such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

Another type of variable region modification is to mutate amino acid residues within the CDR regions to improve one or more binding properties (e.g., affinity) of the antibody of interest. Site-directed mutagenesis or PCR-mediated mutagenesis can be performed to introduce the mutation(s) and the effect on antibody binding, or other functional property of interest. Preferably conservative modifications are introduced. The mutations may be amino acid additions, deletions, or preferably substitutions. Moreover, typically no more than one, two, three, four or five residues within a CDR region are altered.

Methionine residues in CDRs of antibodies can be oxidized, resulting in potential chemical degradation and consequent reduction in potency of the antibody. Accordingly, also provided are anti-TIGIT antibodies that have one or more methionine residues in the heavy and/or light chain CDRs replaced with amino acid residues that do not undergo oxidative degradation.

Similarly, deamidation sites may be removed from anti-TIGIT antibodies, particularly in the CDRs.

Potential glycosylation sites within the antigen binding domain are preferably eliminated to prevent glycosylation that may interfere with antigen binding. See, e.g., U.S. Pat. No. 5,714,350.

Targeted Antigen Binding

In various embodiments, the antibody of the present invention is modified to selectively block antigen binding in tissues and environments where antigen binding would be detrimental, but allow antigen binding where it would be beneficial. In one embodiment, a blocking peptide "mask" is generated that specifically binds to the antigen binding surface of the antibody and interferes with antigen binding, which mask is linked to each of the binding arms of the antibody by a peptidase cleavable linker. See, e.g., U.S. Pat. No. 8,518,404 to CytomX. Such constructs are useful for treatment of cancers in which protease levels are greatly increased in the tumor microenvironment compared with non-tumor tissues. Selective cleavage of the cleavable linker in the tumor microenvironment allows disassociation of the masking/blocking peptide, enabling antigen binding selectively in the tumor, rather than in peripheral tissues in which antigen binding might cause unwanted side effects.

Alternatively, in a related embodiment, a bivalent binding compound ("masking ligand") comprising two antigen binding domains is developed that binds to both antigen binding surfaces of the (bivalent) antibody and interfere with antigen binding, in which the two binding domains masks are linked to each other (but not the antibody) by a cleavable linker, for example cleavable by a peptidase. See, e.g., Int'l Pat. App. Pub. No. WO 2010/077643 to Tegopharm Corp. Masking ligands may comprise, or be derived from, the antigen to which the antibody is intended to bind, or may be independently generated. Such masking ligands are useful for treatment of cancers in which protease levels are greatly increased in the tumor microenvironment compared with non-tumor tissues. Selective cleavage of the cleavable linker in the tumor microenvironment allows disassociation of the two binding domains from each other, reducing the avidity for the antigen-binding surfaces of the antibody. The resulting dissociation of the masking ligand from the antibody enables antigen binding selectively in the tumor, rather than in peripheral tissues in which antigen binding might cause unwanted side effects.

Fcs and Modified Fcs

In addition to the activity of a therapeutic antibody arising from binding of the antigen binding domain to the antigen (e.g. blocking of a cognate ligand or receptor protein in the case of antagonist antibodies, or induced signaling in the case of agonist antibodies), the Fc portion of the antibody interact with the immune system generally in complex ways to elicit any number of biological effects. Effector functions, such as The Fc region of an immunoglobulin is responsible for many important antibody functions, such as antigen-dependent cellular cytotoxicity (ADCC), complement dependent cytotoxicity (CDC), and antibody-dependent cell-mediated phagocytosis (ADCP), result in killing of target cells, albeit by different mechanisms. There are five major classes, or isotypes, of heavy chain constant region (IgA, IgG, IgD, IgE, IgM), each with characteristic effector functions. These isotypes can be further subdivided into subclasses, for example, IgG is separated into four subclasses known as IgG1, IgG2, IgG3, and IgG4. IgG molecules interact with three classes of Fcγ receptors (FcγR) specific for the IgG class of antibody, namely FcγRI, FcγRII, and FcγRIII. The important sequences for the binding of IgG to the FcγR receptors have been reported to be located in the CH2 and CH3 domains. The serum half-life of an antibody is influenced by the ability of that antibody to bind to the neonatal Fc receptor (FcRn).

Antibodies of the present invention may comprise the variable domains of the invention combined with constant domains comprising different Fc regions, selected based on the biological activities (if any) of the antibody for the intended use. Salfeld (2007) *Nat. Biotechnol.* 25:1369. Human IgGs, for example, can be classified into four subclasses, IgG1, IgG2, IgG3, and IgG4, and each these of these comprises an Fc region having a unique profile for binding to one or more of Fcγ receptors (activating receptors FcγRI (CD64), FcγRIIA, FcγRIIC (CD32); FcγRIIIA and FcγRIIIB (CD16) and inhibiting receptor FcγRIIB), and for the first component of complement (C1q). Human IgG1 and IgG3 bind to all Fcγ receptors; IgG2 binds to FcγRIIA$_{H131}$, and with lower affinity to FcγRIIA$_{R131}$ FcγRIIIA$_{V158}$; IgG4 binds to FcγRI, FcγRIIA, FcγRIIB, FcγRIIC, and FcγRIIIA$_{V158}$; and the inhibitory receptor FcγRIIB has a lower affinity for IgG1, IgG2 and IgG3 than all other Fcγ receptors. Bruhns et al. (2009) *Blood* 113:3716. Studies have shown that FcγRI does not bind to IgG2, and FcγRIIIB does not bind to IgG2 or IgG4. Id. In general, with regard to ADCC activity, human IgG1≥IgG3>>IgG4≥IgG2. As a consequence, for example, an IgG1 constant domain, rather than an IgG2 or IgG4, might be chosen for use in a drug where ADCC is desired; IgG3 might be chosen if activation of FcγRIIIA-expressing NK cells, monocytes of macrophages; and IgG4 might be chosen if the antibody is to be used to desensitize allergy patients. IgG4 may also be selected if it is desired that the antibody lack all effector function.

Anti-TIGIT variable regions described herein may be linked (e.g., covalently linked or fused) to an Fc, e.g., an IgG1, IgG2, IgG3 or IgG4 Fc, which may be of any allotype or isoallotype, e.g., for IgG1: G1m, G1m1 (a), G1m2(x), G1m3(f), G1m17(z); for IgG2: G2m, G2m23(n); for IgG3: G3m, G3m21(g1), G3m28(g5), G3m11(b0), G3m5(b1), G3m13(b3), G3m14(b4), G3m10(b5), G3m15(s), G3m16 (t), G3m6(c3), G3m24(c5), G3m26(u), G3m27(v). See, e.g., Jefferis et al. (2009) *mAbs* 1:1). Selection of allotype may be influenced by the potential immunogenicity concerns, e.g. to minimize the formation of anti-drug antibodies.

In certain embodiments, anti-TIGIT variable regions described herein are linked to an Fc that binds to one or more activating Fc receptors (FcγRI/CD64, FcγRIIa/CD32 or FcγRIIIa/CD16), and thereby stimulate ADCC and may cause T cell depletion. In certain embodiments, anti-TIGIT variable regions described herein are linked to a human IgG1 or IgG3 Fc, i.e., the antibodies are of the IgG1 or IgG3 isotype. In certain embodiments, anti-TIGIT antibodies are depleting antibodies, in particular, they deplete T$_{reg}$ cells, but not T$_{eff}$ cells, in the tumor microenvironment (and thereby enhance anti-tumor activity), but do not significantly deplete T$_{reg}$ and T$_{eff}$ cells outside of the tumor microenvironment, e.g., in the periphery. In certain embodiments, anti-TIGIT antibodies are of an isotype, either naturally occurring or non-naturally occurring (e.g., including mutation(s)) that stimulate T$_{reg}$ cell depletion or elimination at the tumor site and concomitant activation of T$_{eff}$ cells. In certain embodiments, anti-TIGIT antibodies create an elevated T$_{eff}$ to T$_{reg}$ ratio at the tumor site, which is indicative of potent anti-tumor activity, preferably without significantly depleting T$_{reg}$ and T$_{eff}$ cells that are outside of the tumor microenvironment, e.g., in the periphery.

In other embodiments, anti-TIGIT antibodies block the immunosuppressive activity of T$_{regs}$. In certain embodiments, anti-TIGIT antibodies have an Fc with reduced or eliminated FcR binding, e.g., reduced binding to activating FcRs.

Anti-TIGIT variable regions described herein may be linked to a non-naturally occurring Fc region, e.g., an effectorless or mostly effectorless Fc (e.g., human IgG2 or IgG4) or, alternatively, an Fc with enhanced binding to one or more activating Fc receptors (FcγRI, FcγRIIa or FcγRIIIa), such as to enhance T$_{reg}$ depletion in the tumor environment.

Variable regions described herein may be linked to an Fc comprising one or more modifications, typically to alter one or more functional properties of the antibody, such as serum half-life, complement fixation, Fc receptor binding, and/or antigen-dependent cellular cytotoxicity. Furthermore, an antibody described herein may be chemically modified (e.g., one or more chemical moieties can be attached to the antibody) or it may be modified to alter its glycosylation, to alter one or more functional properties of the antibody. Each of these embodiments is described in further detail below. The numbering of residues in the Fc region is that of the EU index of Kabat. Sequence variants disclosed herein are provided with reference to the residue number followed by the amino acid that is substituted in place of the naturally occurring amino acid, optionally preceded by the naturally occurring residue at that position. Where multiple amino acids may be present at a given position, e.g. if sequences differ between naturally occurring isotypes, or if multiple mutations may be substituted at the position, they are separated by slashes (e.g. "X/Y/Z").

For example, one may make modifications in the Fc region in order to generate an Fc variant with (a) increased or decreased antibody-dependent cell-mediated cytotoxicity (ADCC), (b) increased or decreased complement mediated cytotoxicity (CDC), (c) increased or decreased affinity for C1q and/or (d) increased or decreased affinity for a Fc receptor relative to the parent Fc. Such Fc region variants will generally comprise at least one amino acid modification in the Fc region. Combining amino add modifications is thought to be particularly desirable. For example, the variant Fc region may include two, three, four, five, etc. substitutions therein, e.g. of the specific Fc region positions identified herein. Exemplary Fc sequence variants are disclosed herein, and are also provided at U.S. Pat. Nos. 5,624,821; 6,277,375; 6,737; 056; 6,194,551; 7,317,091; 8,101,720; PCT Patent Publications WO 00/42072; WO 01/58957; WO 04/016750; WO 04/029207; WO 04/035752; WO 04/074455; WO 04/099249; WO 04/063351; WO 05/070963; WO 05/040217, WO 05/092925 and WO 06/020114.

Reducing Effector Function

ADCC activity may be reduced by modifying the Fc region. In certain embodiments, sites that affect binding to Fc receptors may be removed, preferably sites other than salvage receptor binding sites. In other embodiments, an Fc region may be modified to remove an ADCC site. ADCC sites are known in the art; see, for example, Sarmay et al. (1992) *Molec. Immunol.* 29 (5): 633-9 with regard to ADCC sites in IgG1. In one embodiment, the G236R and L328R variant of human IgG1 effectively eliminates FcγR binding. Horton et al. (2011) *J. Immunol.* 186:4223 and Chu et al. (2008) *Mol. Immunol.* 45:3926. In other embodiments, the Fc having reduced binding to FcγRs comprised the amino acid substitutions L234A, L235E and G237A. Gross et al. (2001) *Immunity* 15:289.

CDC activity may also be reduced by modifying the Fc region. Mutations at IgG1 positions D270, K322, P329 and P331, specifically alanine mutations D270A, K322A, P329A and P331A, significantly reduce the ability of the corresponding antibody to bind C1q and activate complement. Idusogie et al. (2000) *J. Immunol.* 164:4178; WO 99/51642. Modification of position 331 of IgG1 (e.g. P331S) has been shown to reduce complement binding. Tao et al. (1993) *J. Exp. Med.* 178:661 and Canfield & Morrison (1991) *J. Exp. Med.* 173:1483. In another example, one or more amino acid residues within amino acid positions 231 to 239 are altered to thereby reduce the ability of the antibody to fix complement. WO 94/29351.

In some embodiments, the Fc with reduced complement fixation has the amino acid substitutions A330S and P331S. Gross et al. (2001) *Immunity* 15:289.

For uses where effector function is to be avoided altogether, e.g. when antigen binding alone is sufficient to generate the desired therapeutic benefit, and effector function only leads to (or increases the risk of) undesired side effects, IgG4 antibodies may be used, or antibodies or fragments lacking the Fc region or a substantial portion thereof can be devised, or the Fc may be mutated to eliminate glycosylation altogether (e.g. N297A). Alternatively, a hybrid construct of human IgG2 ($C_H1$ domain and hinge region) and human IgG4 ($C_H2$ and $C_H3$ domains) has been generated that is devoid of effector function, lacking the ability to bind the FcγRs (like IgG2) and unable to activate complement (like IgG4). Rother et al. (2007) *Nat. Biotechnol* 25:1256. See also Mueller et al. (1997) *Mol. Immunol.* 34:441; Labrijn et al. (2008) *Curr. Op. Immunol.* 20:479 (discussing Fc modifications to reduce effector function generally).

In other embodiments, the Fc region is altered by replacing at least one amino acid residue with a different amino acid residue to reduce all effector function(s) of the antibody. For example, one or more amino acids selected from amino acid residues 234, 235, 236, 237, 297, 318, 320 and 322 can be replaced with a different amino acid residue such that the antibody has decreased affinity for an effector ligand but retains the antigen-binding ability of the parent antibody. The effector ligand to which affinity is altered can be, for example, an Fc receptor (residues 234, 235, 236, 237, 297) or the C1 component of complement (residues 297, 318, 320, 322). U.S. Pat. Nos. 5,624,821 and 5,648,260, both by Winter et al.

One early patent application proposed modifications in the IgG Fc region to decrease binding to FcγRI to decrease ADCC (234A; 235E; 236A; G237A) or block binding to complement component C1q to eliminate CDC (E318A or V/K320A and K322A/Q). WO 88/007089. See also Duncan & Winter (1988) *Nature* 332:563; Chappel et al. (1991) *Proc. Nat'l Acad. Sci.* (USA) 88:9036; and Sondermann et al. (2000) *Nature* 406:267 (discussing the effects of these mutations on FcγRIII binding).

Fc modifications reducing effector function also include substitutions, insertions, and deletions at positions 234, 235, 236, 237, 267, 269, 325, and 328, such as 234G, 235G, 236R, 237K, 267R, 269R, 325L, and 328R. An Fc variant may comprise 236R/328R. Other modifications for reducing FcγR and complement interactions include substitutions 297A, 234A, 235A, 237A, 318A, 228P, 236E, 268Q, 309L, 330S, 331S, 220S, 226S, 229S, 238S, 233P, and 234V. These and other modifications are reviewed in Strohl (2009) *Current Opinion in Biotechnology* 20:685-691. Effector functions (both ADCC and complement activation) can be reduced, while maintaining neonatal FcR binding (maintaining half-life), by mutating IgG residues at one or more of positions 233-236 and 327-331, such as E233P, L234V, L235A, optionally G236∆, A327G, A330S and P331S in IgG1; E233P, F234V, L235A, optionally G236∆ in IgG4; and A330S and P331S in IgG2. See Armour et al. (1999) *Eur. J. Immunol.* 29:2613; WO 99/58572. Other mutations that reduce effector function include L234A and L235A in IgG1 (Alegre et al. (1994) *Transplantation* 57:1537); V234A and G237A in IgG2 (Cole et al. (1997) *J. Immunol.* 159:3613; see also U.S. Pat. No. 5,834,597); and S228P and L235E for IgG4 (Reddy et al. (2000) *J. Immunol.* 164:1925).

Another combination of mutations for reducing effector function in a human IgG1 include L234F, L235E and P331S. Oganesyan et al. (2008) *Acta Crystallogr. D. Biol. Crystallogr.* 64:700. See generally Labrijn et al. (2008) *Curr. Op. Immunol.* 20:479. Additional mutations found to decrease effector function in the context of an Fc (IgG1) fusion protein (abatacept) are C226S, C229S and P238S (EU residue numbering). Davis et al. (2007) *J. Immunol.* 34:2204.

Other Fc variants having reduced ADCC and/or CDC are disclosed at Glaesner et al. (2010) *Diabetes Metab. Res. Rev.* 26:287 (F234A and L235A to decrease ADCC and ADCP in an IgG4); Hutchins et al. (1995) *Proc. Nat'l Acad. Sci. (USA)* 92:11980 (F234A, G237A and E318A in an IgG4); An et al. (2009) *MAbs* 1:572 and U.S. Pat. App. Pub. 2007/0148167 (H268Q, V309L, A330S and P331S in an IgG2); McEarchern et al. (2007) *Blood* 109:1185 (C226S, C229S, E233P, L234V, L235A in an IgG1); Vafa et al. (2014) *Methods* 65:114 (V234V, G237A, P238S, H268A, V309L, A330S, P331S in an IgG2).

In certain embodiments, an Fc is chosen that has essentially no effector function, i.e., it has reduced binding to FcγRs and reduced complement fixation. An exemplary Fc, e.g., IgG1 Fc, that is effectorless comprises the following five mutations: L234A, L235E, G237A, A330S and P331S. Gross et al. (2001) *Immunity* 15:289. These five substitutions may be combined with N297A to eliminate glycosylation as well.

Enhancing Effector Function

Alternatively, ADCC activity may be increased by modifying the Fc region. With regard to ADCC activity, human IgG1≥IgG3>>IgG4≥IgG2, so an IgG1 constant domain, rather than an IgG2 or IgG4, might be chosen for use in a drug where ADCC is desired. Alternatively, the Fc region may be modified to increase antibody dependent cellular cytotoxicity (ADCC) and/or to increase the affinity for an Fcγ receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 434, 433, 435, 436, 437, 438 or 439. See WO 2012/142515 see also WO 00/42072. Exemplary substitutions include 236A, 239D, 239E, 268D, 267E, 268:E, 268F, 324T, 332D, and 332E. Exemplary variants include 239D-332E, 236A-332E, 236A-239D-332E, 268F-324T, 267E-268F, 267E-324T, and 267E-268F-324T. For example, human IgG1Fcs comprising the G236A variant, which can optionally be combined with I332E, have been shown to increase the FcγRIIA/FcγRIIB binding affinity ratio approximately 15-fold. Richards et al. (2008) *Mol. Cancer Therap.* 7:2517; Moore et al. (2010) *mAbs* 2:181. Other modifications for enhancing FcγR and complement interactions include but are not limited to substitutions 298A, 333A, 334A, 326A, 247I, 339D, 339Q, 280H, 290S, 298D, 298V, 243L, 292P, 300L, 396L, 305I and 396L. These and other modifications are reviewed in Strohl (2009) *Current Opinion in Biotechnology* 20:685-691. Specifically, both ADCC and CDC may be enhanced by changes at position E333 of IgG1, e.g. E333A. Shields et al. (2001) *J. Biol. Chem.* 276:6591. The use of P247I and A339D/Q mutations to enhance effector function in an IgG1 is disclosed at WO 2006/020114, and D280H, K290S±S298D/V is disclosed at WO 2004/074455, The K326A/W and E333A/S variants have been shown to increase effector function in human IgG1, and E333S in IgG2. Idusogie et al. (2001) *J. Immunol.* 166:2571.

Specifically, the binding sites on human IgG1 for FcγR1, FcγRII, FcγRIII and FcRn have been mapped, and variants with improved binding have been described. Shields et al. (2001) *J. Biol. Chem.* 276:6591-6604. Specific mutations at positions 256, 290, 298, 333, 334 and 339 were shown to improve binding to FcγRIII, including the combination mutants T256A-S298A, S298A-E333A, S298A-K224A and S298A-E333A-K334A (having enhanced FcγRIIIa binding and ADCC activity). Other IgG1 variants with strongly enhanced binding to FcγRIIIa have been identified, including variants with 5239D-I332E and 5239D-I332E-A330L mutations, which showed the greatest increase in affinity for FcγRIIIa, a decrease in FcγRIIb binding, and strong cytotoxic activity in cynomolgus monkeys. Lazar et al. (2006) *Proc. Nat'l Acad. Sci. (USA)* 103:4005; Awan et al. (2010) *Blood* 115:1204; Desjarlais & Lazar (2011) *Exp. Cell Res.* 317:1278. Introduction of the triple mutations into antibodies such as alemtuzumab (CD52-specific), trastuzumab (HER2/neu-specific), rituximab (CD20-specific), and cetuximab (EGFR-specific) translated into greatly enhanced ADCC activity in vitro, and the 5239D-I332E variant showed an enhanced capacity to deplete B cells in monkeys. Lazar et al. (2006) *Proc. Nat'l Acad. Sci. (USA)* 103:4005. In addition, IgG1 mutants containing L235V, F243L, R292P, Y300L, V305I and P396L mutations, which exhibited enhanced binding to FcγRIIIa and concomitantly enhanced ADCC activity in transgenic mice expressing human FcγRIIIa in models of B cell malignancies and breast cancer have been identified. Stavenhagen et al. (2007) *Cancer Res.* 67:8882; U.S. Pat. No. 8,652,466; Nordstrom et al. (2011) *Breast Cancer Res.* 13:R123.

Different IgG isotypes also exhibit differential CDC activity (IgG3>IgG1>>IgG2≈IgG4). Dangl et al. (1988) *EMBO J.* 7:1989. For uses in which enhanced CDC is desired, it is also possible to introduce mutations that increase binding to C1q. The ability to recruit complement (CDC) may be enhanced by mutations at K326 and/or E333 in an IgG2, such as K326W (which reduces ADCC activity) and E333S, to increase binding to C1q, the first component of the complement cascade. Idusogie et (2001) *J. Immunol.* 166: 2571. Introduction of S267E/H268F/S324T (alone or in any combination) into human IgG1 enhances C1q binding. Moore et al. (2010) *mAbs* 2:181. The Fc region of the IgG1/IgG3 hybrid isotype antibody "113F" of Natsume et al. (2008) *Cancer Res.* 68:3863 (FIG. 1 therein) also confers enhanced CDC. See also Michaelsen et (2009) *Scand. J. Immunol.* 70:553 and Redpath et al. (1998) *Immunology* 93:595.

Additional mutations that can increase or decrease effector function are disclosed at Dall' Acqua et al. (2006) *J. Immunol.* 177:1129. See also Carter (2006) *Nat. Rev. Immunol.* 6:343; Presta (2008) *Curr. Op. Immunol.* 20:460.

Although not necessarily relevant to the antagonist anti-TIGIT mAbs of the present invention, Fc variants that enhance affinity for the inhibitory receptor FcγRIIb may enhance apoptosis-inducing or adjuvant activity, Li & Ravetch (2011) *Science* 333:1030; Li & Ravetch (2012) *Proc. Nat'l Acad. Sci. (USA)* 109:10966; U.S. Pat. App. Pub. 2014/0010812. Such variants may provide an antibody with immunomodulatory activities related to FcγRIIb$^+$ cells, including for example B cells and monocytes. In one embodiment, the Fc variants provide selectively enhanced affinity to FcγRIIb relative to one or more activating receptors. Modifications for altering binding to FcγRIIb include one or more modifications at a position selected from the group consisting of 234, 235, 236, 237, 239, 266, 267, 268, 325, 326, 327, 328, and 332, according to the EU index. Exemplary substitutions for enhancing FcγRIIb affinity include but are not limited to 234D, 234E, 234F, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. Exemplary substitutions include 235Y, 236D, 239D, 266M, 267E, 268D, 268E, 328F, 328W, and 328Y. Other Fc variants for enhancing binding to FcγRIIb include 235Y-267E, 236D-267E, 239D-268D, 239D-267E, 267E-268D, 267E-268E, and 267E-328F. Specifically, the S267E, G236D, S239D, L328F and I332E variants, including the S267E-L328F double variant, of human IgG1 are of particular value in specifically enhancing affinity for the inhibitory FcγRIIb receptor. Chu et al. (2008) *Mol. Immunol.* 45:3926; U.S. Pat. App. Pub. 2006/024298; WO 2012/087928. Enhanced specificity for FcγRIIb (as distinguished from FcγRIIa$^{R131}$) may be obtained by adding the P238D substitution and other mutations (Mimoto et al. (2013) *Protein. Eng. Des. & Selection* 26:589; WO 2012/115241), as well as V262E and V264E (Yu et al. (2013) *J. Am. Chem. Soc.* 135:9723, and WO 2014/184545).

Half-Life Extension

In certain embodiments, the antibody is modified to increase its biological half-life. Various approaches are possible. For example, this may be done by increasing the binding affinity of the Fc region for FcRn. In one embodiment, the antibody is altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Other exemplary Fc variants that increase binding to FcRn and/or improve pharmacokinetic properties include substitutions at positions 259, 308, and 434, including for example 259I, 308F, 428L, 428M, 434S, 434H, 434F, 434Y, and 434M. Other variants that increase Fc binding to FcRn include: 250E, 250Q, 428L, 428F, 250Q/428L (Hinton et al., 2004, J. Biol. Chem. 279(8): 6213-6216, Hinton et al. 2006 *Journal of Immunology* 176:346-356), 256A, 272A, 305A, 307A, 311A, 312A, 378Q, 380A, 382A, 434A (Shields et al, Journal of Biological Chemistry, 2001, 276 (9):6591-6604), 252F, 252Y, 252W, 254T, 256Q, 256E, 256D, 433R, 434F, 434Y, 252Y/254T/256E, 433K/434F/436H (Dall' Acqua et al. Journal of Immunology, 2002, 169:5171-5180, Dall' Acqua et al., 2006, Journal of Biological Chemistry 281:23514-23524). See U.S. Pat. No. 8,367,805.

Modification of certain conserved residues in IgG Fc (I253, H310, Q311, H433, N434), such as the N434A variant (Yeung et al. (2009) *J. Immunol.* 182:7663), have been proposed as a way to increase FcRn affinity, thus increasing the half-life of the antibody in circulation. WO 98/023289. The combination Fc variant comprising M428L and N434S has been shown to increase FcRn binding and increase serum half-life up to five-fold. Zalevsky et al. (2010) *Nat. Biotechnol.* 28:157. The combination Fc variant comprising T307A, E380A and N434A modifications also extends half-life of IgG1 antibodies. Petkova et al. (2006) *Int. Immunol.* 18:1759. In addition, combination Fc variants comprising M252Y-M428L, M428L-N434H, M428L-N434F, M428L-N434Y, M428L-N434A, M428L-N434M, and M428L-N434S variants have also been shown to extend half-life. WO 2009/086320.

Further, a combination Fc variant comprising M252Y, S254T and T256E increases half-life-nearly 4-fold. Dall'Acqua et all. (2006) *J. Biol. Chem.* 281:23514. A related IgG1 modification providing increased FcRn affinity but reduced pH dependence (M252Y-S254T-T256E-H433K-N434F) has been used to create an IgG1 construct ("MST-HN Abdeg") for use as a competitor to prevent binding of other antibodies to FcRn, resulting in increased clearance of that other antibody, either endogenous IgG (e.g. in an autoimmune setting) or another exogenous (therapeutic) mAb. Vaccaro et al. (2005) *Nat. Biotechnol.* 23:1283; WO 2006/130834.

Other modifications for increasing FcRn binding are described in Yeung et al. (2010) *J. Immunol.* 182:7663-7671; 6,277,375, 6,821,505; WO 97/34631; WO 2002/060919.

In certain embodiments, hybrid IgG isotypes may be used to increase FcRn binding, and potentially increase half-life. For example, an IgG1/IgG3 hybrid variant may be constructed by substituting IgG1 positions in the CH2 and/or CH3 region with the amino acids from IgG3 at positions where the two isotypes differ. Thus a hybrid variant IgG antibody may be constructed that comprises one or more substitutions, e.g., 274Q, 276K, 300F, 339T, 356E, 358M, 384S, 392N, 397M, 422I, 435R, and 436F. In other embodiments described herein, an IgG1/IgG2 hybrid variant may be constructed by substituting IgG2 positions in the CH2 and/or CH3 region with amino acids from IgG1 at positions where the two isotypes differ. Thus a hybrid variant IgG antibody may be constructed that comprises one or more substitutions, e.g., one or more of the following amino acid substitutions: 233E, 234L, 235L, -236G (referring to an insertion of a glycine at position 236), and 327A. See U.S. Pat. No. 8,629,113. A hybrid of IgG1/IgG2/IgG4 sequences has been generated that purportedly increases serum half-life and improves expression. U.S. Pat. No. 7,867,491 (sequence number 18 therein).

The serum half-life of the antibodies of the present invention can also be increased by pegylation. An antibody can be pegylated to, for example, increase the biological (e.g., serum) half-life of the antibody. To pegylate an antibody, the antibody, or fragment thereof, typically is reacted with a polyethylene glycol (PEG) reagent, such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies described herein. See for example, EP 0154316 by Nishimura et al. and EP 0401384 by Ishikawa et al.

Alternatively, under some circumstances it may be desirable to decrease the half-life of an antibody of the present invention, rather than increase it. Modifications such as I253A (Hornick et al. (2000) *J. Nucl. Med.* 41:355) and H435A/R, I253A or H310A (Kim et al. (2000) *Eur. J. Immunol.* 29:2819) in Fc of human IgG1 can decrease FcRn binding, thus decreasing half-life (increasing clearance) for use in situations where rapid clearance is preferred, such a medical imaging. See also Kenanova et al. (2005) *Cancer Res.* 65:622. Other means to enhance clearance include formatting the antigen binding domains of the present invention as antibody fragments lacking the ability to bind FcRn, such as Fab fragments. Such modification can reduce the circulating half-life of an antibody from a couple of weeks to a matter of hours. Selective PEGylation of antibody fragments can then be used to fine-tune (increase) the half-life of the antibody fragments if necessary. Chapman et al. (1999) *Nat. Biotechnol.* 17:780. Antibody fragments may also be fused to human serum albumin, e.g. in a fusion protein construct, to increase half-life. Yeh et al. (1992) *Proc. Nat'l Acad. Sci.* 89:1904. Alternatively, a bispecific antibody may be constructed with a first antigen binding domain of the present invention and a second antigen binding domain that binds to human serum albumin (HSA). See Int'l Pat. Appl. Pub. WO 2009/127691 and patent references cited therein. Alternatively, specialized polypeptide sequences can be added to antibody fragments to increase half-life, e.g. "XTEN" polypeptide sequences. Schellenberger et al. (2009) *Nat. Biotechnol.* 27:1186; Int'l Pat. Appl. Pub. WO 2010/091122.

Additional Fc Variants

When using an IgG4 constant domain, it is usually preferable to include the substitution S228P, which mimics the hinge sequence in IgG1 and thereby stabilizes IgG4 molecules, e.g. reducing Fab-arm exchange between the therapeutic antibody and endogenous IgG4 in the patient being treated. Labrijn et al. (2009) *Nat. Biotechnol.* 27:767; Reddy et al. (2000) *J. Immunol.* 164:1925.

A potential protease cleavage site in the hinge of IgG1 constructs can be eliminated by D221G and K222S modifications, increasing the stability of the antibody. WO 2014/043344.

The affinities and binding properties of an Fc variant for its ligands (Fe receptors) may be determined by a variety of in vitro assay methods (biochemical or immunological based assays) known in the art including but not limited to, equilibrium methods (e.g., enzyme-linked immunosorbent assay (ELISA), or radioimmunoassay (RIA)), or kinetics (e.g., BIACORE® SPR analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

In still other embodiments, the glycosylation of an antibody is modified to increase or decrease effector function. For example, an aglycoslated antibody can be made that lacks all effector function by mutating the conserved asparagine residue at position 297 (e.g. N297A), thus abolishing complement and FcγRI binding. Bolt et al. (1993) *Eur. J. Immunol.* 23:403. See also Tao & Morrison (1989) *J. Immunol.* 143:2595 (using N297Q in IgG1 to eliminate glycosylation at position 297).

Although aglycosylated antibodies generally lack effector function, mutations can be introduced to restore that function. Aglycosylated antibodies, e.g. those resulting from N297A/C/D/or H mutations or produced in systems (e.g. *E. coli*) that do not glycosylate proteins, can be further mutated to restore FcγR binding, e.g. S298G and/or T299A/G/or H (WO 2009/079242), or E382V and M428I (Jung et al. (2010) *Proc. Nat'l Acad. Sci.* (USA) 107:604).

Additionally, an antibody with enhanced ADCC can be made by altering the glycosylation. For example, removal of fucose from heavy chain Asn297-linked oligosaccharides has been shown to enhance ADCC, based on improved binding to FcγRIIIa. Shields et al. (2002) *JBC* 277:26733; Niwa et al. (2005) *J. Immunol. Methods* 306: 151; Cardarelli et al. (2009) *Clin. Cancer Res.* 15:3376 (MDX-1401); Cardarelli et al. (2010) *Cancer Immunol. Immunotherap.* 59:257 (MDX-1342). Such low fucose antibodies may be produced, e.g., in knockout Chinese hamster ovary (CHO) cells lacking fucosyltransferase (FUT8) (Yamane-Ohnuki et al. (2004) *Biotechnol. Bioeng.* 87:614), or in other cells that generate afucosylated antibodies. See, e.g., Zhang et al. (2011) *mAbs* 3:289 and Li et al. (2006) *Nat. Biotechnot* 24:210 (both describing antibody production in glycoengineered *Pichia pastoris.*); Mossner et al. (2010) *Blood* 115: 4393; Shields et al. (2002) *J. Biol. Chem.* 277:26733; Shinkawa et al. (2003) *J. Biol. Chem.* 278:3466; EP 1176195B1. ADCC can also be enhanced as described in PCT Publication WO 03/035835, which discloses use of a variant CHO cell line, Lec13, with reduced ability to attach fucose to Asn(297)-linked carbohydrates, also resulting in hypofucosylation of antibodies expressed in that host cell. See also Shields, R. L. et al. (2002) *J. Biol. Chem.* 277: 26733-26740. Alternatively, fucose analogs may be added to culture medium during antibody production to inhibit incorporation of fucose into the carbohydrate on the antibody. WO 2009/135181.

Increasing bisecting GlcNac structures in antibody-linked oligosaccharides also enhances ADCC. PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180).

Additional glycosylation variants have been developed that are devoid of galactose, sialic acid, fucose and xylose residues (so-called GNGN glycoforms), which exhibit enhanced ADCC and ADCP but decreased CDC, as well as others that are devoid of sialic acid, fucose and xylose (so-called G1/G2 glycoforms), which exhibit enhanced ADCC, ADCP and CDC. U.S. Pat. App. Pub. No. 2013/0149300. Antibodies having these glycosylation patterns are optionally produced in genetically modified *N. benthamiana* plants in which the endogenous xylosyl and fucosyl transferase genes have been knocked-out.

Glycoengineering can also be used to modify the anti-inflammatory properties of an IgG construct by changing the α2,6 sialyl content of the carbohydrate chains attached at Asn297 of the Fc regions, wherein an increased proportion of α2,6 sialylated forms results in enhanced anti-inflammatory effects. See Nimmerjahn et al. (2008) *Ann. Rev. Immunol.* 26:513. Conversely, reduction in the proportion of antibodies having α2,6 sialylated carbohydrates may be useful in cases where anti-inflammatory properties are not wanted. Methods of modifying α2,6 sialylation content of antibodies, for example by selective purification of α2,6 sialylated forms or by enzymatic modification, are provided at U.S. Pat. Appl. Pub. No. 2008/0206246. In other embodiments, the amino acid sequence of the Fc region may be modified to mimic the effect of α2,6 sialylation, for example by inclusion of an F241A modification. WO 2013/095966.

III. Antibody Physical Properties

Antibodies described herein can contain one or more glycosylation sites in either the light or heavy chain variable region. Such glycosylation sites may result in increased immunogenicity of the antibody or an alteration of the pK of the antibody due to altered antigen binding (Marshall et al. (1972) *Ann. Rev. Biochem.* 41:673-702; Gala and Morrison (2004) *J. Immunol.* 172:5489-94; Wallick et al. (1988) *J. Exp. Med.* 168:1099-109; Spiro (2002) *Glycobiology* 12:43R-56R; Parekh et al. (1985) *Nature* 316:452-7; Mimura et al. (2000) *Mol. Immunol.* 37:697-706). Glycosylation has been known to occur at motifs containing an N-X-S/T sequence. In some instances, it is preferred to have an anti-TIGIT antibody that does not contain variable region glycosylation. This can be achieved either by selecting antibodies that do not contain the glycosylation motif in the variable region or by mutating residues within the glycosylation region.

In certain embodiments, the antibodies described herein do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-TIGIT antibody that contains a pI value that falls in the normal range. This can be achieved either by selecting antibodies with a pI in the normal range or by mutating charged surface residues.

Each antibody will have a characteristic melting temperature, with a higher melting temperature indicating greater overall stability in vivo (Krishnamurthy R and Manning M C (2002) *Curr Pharm Biotechnol* 3:361-71). Generally, it is preferred that the $T_{M1}$ (the temperature of initial unfolding) be greater than 60° C., preferably greater than 65° C., even more preferably greater than 70° C. The melting point of an antibody can be measured using differential scanning calorimetry (Chen et al (2003) *Pharm Res* 20:1952-60; Ghirlando et al. (1999) *Immunol Lett.* 68:47-52) or circular dichroism (Murray et al. (2002) *J. Chromatogr. Sci.* 40:343-9).

In a preferred embodiment, antibodies are selected that do not degrade rapidly. Degradation of an antibody can be measured using capillary electrophoresis (CE) and MALDI-MS (Alexander A J and Hughes D E (1995) *Anal Chem.* 67:3626-32).

In another preferred embodiment, antibodies are selected that have minimal aggregation effects, which can lead to the triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation can be measured by several techniques, including size-exclusion column (SEC), high performance liquid chromatography (HPLC), and light scattering.

IV. Nucleic Acid Molecules

Another aspect described herein pertains to nucleic acid molecules that encode the antibodies described herein. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and may or may not contain intronic sequences. In a certain embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, for example, an IgG1 region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

V. Antibody Generation

Various antibodies of the present invention, e.g. those that compete with or bind to the same epitope as the anti-human TIGIT antibodies disclosed herein, can be produced using a variety of known techniques, such as the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies described herein can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693, 762 and 6,180,370 to Queen et al.).

In one embodiment, the antibodies described herein are human monoclonal antibodies. Such human monoclonal antibodies directed against TIGIT can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode unrearranged human heavy (µ and γ) and κ light chain immunoglobulin sequences, together with targeted mutations that inactivate the endogenous µ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). The preparation and use of HuMab mice, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In certain embodiments, antibodies described herein are raised using a mouse that carries human immunoglobulin sequences on transgenes and transchromosomes, such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-TIGIT antibodies described herein. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise anti-TIGIT antibodies described herein. For example, mice carrying both a human heavy chain transchromosome and a human light chain transchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-TIGIT antibodies described herein.

Additional mouse systems described in the art for raising human antibodies, e.g., human anti-TIGIT antibodies, include (i) the VELOCIMMUNE® mouse (Regeneron Pharmaceuticals, Inc.), in which the endogenous mouse heavy and light chain variable regions have been replaced, via homologous recombination, with human heavy and light chain variable regions, operatively linked to the endogenous mouse constant regions, such that chimeric antibodies (human V/mouse C) are raised in the mice, and then subsequently converted to fully human antibodies using standard recombinant DNA techniques; and (ii) the MeMo® mouse (Merus Biopharmaceuticals, Inc.), in which the mouse contains unrearranged human heavy chain variable regions but a single rearranged human common light chain variable region. Such mice, and use thereof to raise antibodies, are described in, for example, WO 2009/15777, US 2010/0069614, WO 2011/072204, WO 2011/097603, WO 2011/163311, WO 2011/163314, WO 2012/148873, US 2012/0070861 and US 2012/0073004.

Human monoclonal antibodies described herein can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos.

5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies described herein can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunizations

To generate fully human antibodies to human TIGIT, transgenic or transchromosomal mice containing human immunoglobulin genes (e.g., HCo12, HCo7 or KM mice) can be immunized with a purified or enriched preparation of the TIGIT antigen and/or cells expressing TIGIT, as described for other antigens, for example, by Lonberg et al. (1994) Nature 368(6474): 856-859; Fishwild et al. (1996) Nature Biotechnology 14: 845-851 and WO 98/24884. Alternatively, mice can be immunized with DNA encoding human TIGIT. Preferably, the mice will be 6-16 weeks of age upon the first infusion. For example, a purified or enriched preparation (5-50 µg) of the recombinant TIGIT antigen can be used to immunize the HuMAb mice intraperitoneally. In the event that immunizations using a purified or enriched preparation of the TIGIT antigen do not result in antibodies, mice can also be immunized with cells expressing TIGIT, e.g., a cell line, to promote immune responses. Exemplary cell lines include TIGIT-overexpressing stable CHO and Raji cell lines.

Cumulative experience with various antigens has shown that the HuMAb transgenic mice respond best when initially immunized intraperitoneally (IP) or subcutaneously (SC) with antigen in Ribi's adjuvant, followed by every other week IP/SC immunizations (up to a total of 10) with antigen in Ribi's adjuvant. The immune response can be monitored over the course of the immunization protocol with plasma samples being obtained by retroorbital bleeds. The plasma can be screened by ELISA and FACS (as described below), and mice with sufficient titers of anti-TIGIT human immunoglobulin can be used for fusions. Mice can be boosted intravenously with antigen 3 days before sacrifice and removal of the spleen and lymph nodes. It is expected that 2-3 fusions for each immunization may need to be performed. Between 6 and 24 mice are typically immunized for each antigen. Usually, HCo7, HCo12, and KM strains are used. In addition, both HCo7 and HCo12 transgene can be bred together into a single mouse having two different human heavy chain transgenes (HCo7/HCo12).

Generation of Hybridomas Producing Monoclonal Antibodies to TIGIT

To generate hybridomas producing monoclonal antibodies described herein, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to Sp2/0 nonsecreting mouse myeloma cells (ATCC, CRL 1581) with 50% PEG. Cells are plated at approximately $2 \times 10^5$ in flat bottom microtiter plate, followed by a two week incubation in selective medium containing 10% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify monoclonal antibodies, selected hybridomas can be grown in two-liter spinner-flasks for monoclonal antibody purification. Supernatants can be filtered and concentrated before affinity chromatography with protein A-Sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

VI. Antibody Manufacture

Generation of Transfectomas Producing Monoclonal Antibodies to TIGIT

Antibodies of the present invention, including both specific antibodies for which sequences are provided and other, related anti-TIGIT antibodies, can be produced in a host cell transfectoma using, for example, a combination of recombinant DNA techniques and gene transfection methods as is well known in the art (Morrison, S. (1985) Science 229: 1202).

For example, to express antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or both genes are inserted into the same expression vector. The antibody genes are inserted into the expression vector(s) by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, recombinant expression vectors may carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, CA (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, recombinant expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr– host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies described herein in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13). Antibodies of the present invention can also be produced in glycoengineered strains of the yeast *Pichia pastoris*. Li et al. (2006) *Nat. Biotechnol.* 24:210.

Preferred mammalian host cells for expressing the recombinant antibodies described herein include Chinese Hamster Ovary (CHO cells) (including dhfr– CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

The N- and C-termini of antibody polypeptide chains of the present invention may differ from the expected sequence due to commonly observed post-translational modifications. For example, C-terminal lysine residues are often missing from antibody heavy chains. Dick et al. (2008) *Biotechnol. Bioeng.* 100:1132. N-terminal glutamine residues, and to a lesser extent glutamate residues, are frequently converted to pyroglutamate residues on both light and heavy chains of therapeutic antibodies. Dick et al. (2007) *Biotechnol. Bioeng.* 97:544; Liu et al. (2011) *JBC* 28611211; Liu et al. (2011) *J. Biol. Chem.* 286:11211.

Amino acid sequences for various agonist anti-huTIGIT antibodies of the present invention are provided in the Sequence Listing, which is summarized at Table 5. For the reasons mentioned above, the C-terminal lysine is not included in any of sequences in the Sequence Listing for heavy chains or heavy chain constant domains. However, in an alternative embodiment, each heavy chain for the anti-huTIGIT antibodies of the present invention, and/or genetic construct encoding such antibodies or the heavy or light chains thereof, includes this additional lysine residue at the C-terminus of the heavy chain(s).

VII. Assays

Antibodies described herein can be tested for binding to TIGIT by, for example, standard ELISA. Briefly, microtiter plates are coated with purified TIGIT at 1-2 µg/ml in PBS, and then blocked with 5% bovine serum albumin in PBS. Dilutions of antibody (e.g., dilutions of plasma from TIGIT-immunized mice) are added to each well and incubated for 1-2 hours at 37° C. The plates are washed with PBS/Tween and then incubated with secondary reagent, e.g., for human antibodies, or antibodies otherwise having a human heavy chain constant region, a goat-anti-human IgG Fc-specific polyclonal reagent conjugated to horseradish peroxidase (HRP) for 1 hour at 37° C. After washing, the plates are developed with ABTS substrate (Moss Inc, product: ABTS-1000) and analyzed by a spectrophotometer at OD 415-495. Sera from immunized mice are then further screened by flow cytometry for binding to a cell line expressing human TIGIT, but not to a control cell line that does not express TIGIT. Briefly, the binding of anti-TIGIT antibodies is assessed by incubating TIGIT expressing CHO cells with the anti-TIGIT antibody at 1:20 dilution. The cells are washed and binding is detected with a PE-labeled anti-human IgG Ab. Flow cytometric analyses are performed using a FACScan flow cytometry (Becton Dickinson, San Jose, CA). Preferably, mice that develop the highest titers will be used for fusions.

Analogous experiments may be performed using anti-mouse detection antibodies if mouse anti-huTIGIT antibodies are to be detected.

An ELISA assay as described above can be used to screen for antibodies and, thus, hybridomas that produce antibodies that show positive reactivity with the TIGIT immunogen. Hybridomas that produce antibodies that bind, preferably with high affinity, to TIGIT can then be subcloned and further characterized. One clone from each hybridoma, which retains the reactivity of the parent cells (by ELISA), can then be chosen for making a cell bank, and for antibody purification.

To purify anti-TIGIT antibodies, selected hybridomas can be grown in two-liter spinner-flasks for monoclonal antibody purification. Supernatants can be filtered and concentrated before affinity chromatography with protein A-Sepharose (Pharmacia, Piscataway, NJ). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected anti-TIGIT monoclonal antibodies bind to unique epitopes, each antibody can be biotinylated using commercially available reagents (Pierce, Rockford, IL). Biotinylated MAb binding can be detected with a streptavidin labeled probe. Competition studies using unlabeled monoclonal antibodies and biotinylated monoclonal antibodies can be performed using TIGIT coated-ELISA plates as described above.

To determine the isotype of purified antibodies, isotype ELISAs can be performed using reagents specific for antibodies of a particular isotype. For example, to determine the isotype of a human monoclonal antibody, wells of microtiter plates can be coated with 1 μg/ml of anti-human immunoglobulin overnight at 4° C. After blocking with 1% BSA, the plates are reacted with 1 μg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

To test the binding of monoclonal antibodies to live cells expressing TIGIT, flow cytometry can be used, as described in the Examples. Briefly, cell lines expressing membrane-bound TIGIT (grown under standard growth conditions) are mixed with various concentrations of monoclonal antibodies in PBS containing 0.1% BSA at 4° C. for 1 hour. After washing, the cells are reacted with Phycoerythrin (PE)-labeled anti-IgG antibody under the same conditions as the primary antibody staining. The samples can be analyzed by FACScan instrument using light and side scatter properties to gate on single cells and binding of the labeled antibodies is determined. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-TIGIT antibodies can be further tested for reactivity with the TIGIT antigen by Western blotting. Briefly, cell extracts from cells expressing TIGIT can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. IgG binding can be detected using anti-IgG alkaline phosphatase and developed with BCIP/NBT substrate tablets (Sigma Chem. Co., St. Louis, MO).

Methods for analyzing binding affinity, cross-reactivity, and binding kinetics of various anti-TIGIT antibodies include standard assays known in the art, for example, Biolayer Interferometry (BLI) analysis, and BIACORE® surface plasmon resonance (SPR) analysis using a BIACORE® 2000 SPR instrument (Biacore AB, Uppsala, Sweden).

In one embodiment, an antibody specifically binds to the extracellular region of human TIGIT. An antibody may specifically bind to a particular domain (e.g., a functional domain) within the extracellular domain of TIGIT. In a particular embodiment, the antibody specifically binds to the site on TIGIT to which PVR binds. In certain embodiments, the antibody specifically binds to the extracellular region of human TIGIT and the extracellular region of cynomolgus TIGIT. Preferably, an antibody binds to human TIGIT with high affinity.

VIII. Bispecific Molecules

Antibodies described herein may be used for forming bispecific molecules. An anti-TIGIT antibody, or antigen-binding fragments thereof, can be derivatized or linked to another functional molecule, e.g., another peptide or protein (e.g., another antibody or ligand for a receptor) to generate a bispecific molecule that binds to at least two different binding sites or target molecules. The antibody described herein may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule described herein, an antibody described herein can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, provided herein are bispecific molecules comprising at least one first binding specificity for TIGIT and a second binding specificity for a second target epitope. In an embodiment described herein in which the bispecific molecule is multispecific, the molecule can further include a third binding specificity.

In one embodiment, the bispecific molecules described herein comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

While human monoclonal antibodies are preferred, other antibodies that can be employed in the bispecific molecules described herein are murine, chimeric and humanized monoclonal antibodies.

The bispecific molecules described herein can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) *J. Exp. Med.* 160:1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, IL).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAbxmAb, mAbxFab, FabxF(ab')$_2$ or ligand x Fab fusion protein. A bispecific molecule described herein can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed using art-recognized methods, such as enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

IX. Compositions

Further provided are compositions, e.g., a pharmaceutical compositions, containing anti-TIGIT antibodies, or antigen-binding fragment(s) thereof, described herein, formulated together with a pharmaceutically acceptable carrier. Such compositions may include one or a combination of (e.g., two or more different) antibodies, or immunoconjugates or bispecific molecules described herein. For example, a pharmaceutical composition described herein can comprise a combination of antibodies (or immunoconjugates or bispecifics) that bind to different epitopes on the target antigen or that have complementary activities.

In certain embodiments, a composition comprises an anti-TIGIT antibody at a concentration of at least 1 mg/ml, 5 mg/ml, 10 mg/ml, 50 mg/ml, 100 mg/ml, 150 mg/ml, 200 mg/ml, or at 1-300 mg/ml, or 100-300 mg/ml.

Pharmaceutical compositions described herein also can be administered in combination therapy, i.e., combined with other agents. For example, the combination therapy can include an anti-TIGIT antibody described herein combined with at least one other anti-cancer and/or T-cell stimulating (e.g., activating) agent. Examples of therapeutic agents that can be used in combination therapy are described in greater detail below in the section on uses of the antibodies described herein.

In some embodiments, therapeutic compositions disclosed herein can include other compounds, drugs, and/or agents used for the treatment of cancer. Such compounds, drugs, and/or agents can include, for example, chemotherapy drugs, small molecule drugs or antibodies that stimulate the immune response to a given cancer. In some instances, therapeutic compositions can include, for example, one or more of an anti-CTLA-4 antibody, an anti-PD-1 antibody, an anti-PD-L1 antibody, an anti-CD40 antibody, an anti-OX40 (also known as CD134, TNFRSF4, ACT35 and/or TXGP1L) antibody, an anti-LAG-3 antibody, an anti-CD73 antibody, an anti-CD137 antibody, an anti-CD27 antibody, an anti-CSF-1R antibody, a TLR agonist, or a small molecule antagonist of IDO or TGFβ.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate.

Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient that can be combined with a carrier material to produce a single dosage form will vary depending upon the subject being treated, and the particular mode of administration. The amount of active ingredient that can be combined with a carrier material to produce a single dosage form will generally be that amount of the composition that produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. In a preferred embodiment, anti-TIGIT antibody of the present invention is administered every two weeks. Other preferred dosage regimens for an anti-TIGIT antibody described herein include 1 mg/kg, 3 mg/kg or 5 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. A therapeutic antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

An antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can optionally be administered a prophylactic regime, although in many immune-oncology indications continued treatment is not necessary.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-TIGIT antibody described herein preferably results in a decrease in severity of disease symptoms, an increase in frequency and duration of disease symptom-free periods, or a prevention of impairment or disability due to the disease affliction. In the context of cancer, a therapeutically effective dose preferably prevents further deterioration of physical symptoms associated with cancer. Symptoms of cancer are well-known in the art and include, for example, unusual mole features, a change in the appearance of a mole, including asymmetry, border, color and/or diameter, a newly pigmented skin area, an abnormal mole, darkened area under nail, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreatic metastases, difficulty swallowing, and the like. Therapeutic efficacy may be observable immediately after the first administration of an anti-huTIGIT mAb of the present invention, or it may only be observed after a period of time and/or a series of doses. Such delayed efficacy my only be observed after several months of treatment, up to 6, 9 or 12 months. It is critical not to decide prematurely that an anti-huTIGIT mAb of the present invention lacks therapeutically efficacy in light of the delayed efficacy exhibited by some immune-oncology agents.

A therapeutically effective dose may prevent or delay onset of cancer, such as may be desired when early or preliminary signs of the disease are present. Laboratory tests utilized in the diagnosis of cancer include chemistries (including the measurement of TIGIT levels), hematology, serology and radiology. Accordingly, any clinical or biochemical assay that monitors any of the foregoing may be used to determine whether a particular treatment is a therapeutically effective dose for treating cancer. One of ordinary skill in the art would be able to determine such amounts based on such factors as the subject's size, the severity of the subject's symptoms, and the particular composition or route of administration selected.

A composition described herein can be administered via one or more routes of administration using one or more of a variety of methods known in the art. As will be appreciated by the skilled artisan, the route and/or mode of administration will vary depending upon the desired results. Preferred routes of administration for antibodies described herein include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody described herein can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition described herein can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules for use with anti-TIGIT antibodies described herein include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the anti-TIGIT antibodies described herein can be formulated to ensure proper distribution in vivo. For example, the blood-brain barrier (BBB) excludes many highly hydrophilic compounds. To ensure that the therapeutic compounds described herein cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

X. Uses and Methods

The antibodies, antibody compositions and methods described herein have numerous in vitro and in vivo utilities involving, for example, enhancement of immune response by blocking TIGIT signaling, or detection of TIGIT. In a preferred embodiment, the antibodies described herein are human or humanized antibodies. For example, anti-TIGIT antibodies described herein can be administered to cells in culture, in vitro or ex vivo, or to human subjects, e.g., in vivo, to enhance immunity in a variety of diseases. Accordingly, provided herein are methods of modifying an immune response in a subject comprising administering to the subject an antibody, or antigen-binding fragment thereof, described herein such that the immune response in the subject is enhanced, stimulated or up-regulated.

Preferred subjects include human patients in whom enhancement of an immune response would be desirable. The methods are particularly suitable for treating human patients having a disorder that can be treated by augmenting an immune response (e.g., the T-cell mediated immune response). In a particular embodiment, the methods are particularly suitable for treatment of cancer in vivo. To achieve antigen-specific enhancement of immunity, anti-TIGIT antibodies described herein can be administered together with an antigen of interest or the antigen may already be present in the subject to be treated (e.g., a tumor-bearing or virus-bearing subject). When antibodies to TIGIT are administered together with another agent, the two can be administered separately or simultaneously.

Also encompassed are methods for detecting the presence of human TIGIT antigen in a sample, or measuring the amount of human TIGIT antigen, comprising contacting the sample, and a control sample, with a human monoclonal antibody, or an antigen binding fragment thereof, which specifically binds to human TIGIT, under conditions that allow for formation of a complex between the antibody or fragment thereof and human TIGIT. The formation of a complex is then detected, wherein a difference in complex formation between the sample compared to the control sample is indicative the presence of human TIGIT antigen in the sample. Moreover, the anti-TIGIT antibodies described herein can be used to purify human TIGIT via immunoaffinity purification.

Given the ability of anti-TIGIT antibodies described herein to block inhibition or co-inhibition of T cell responses, e.g., antigen-specific T cell responses, provided herein are in vitro and in vivo methods of using the antibodies described herein to stimulate, enhance or upregulate antigen-specific T cell responses, e.g., anti-tumor T cell responses. In certain embodiments, CD3 stimulation is also provided (e.g., by coincubation with a cell expressing membrane CD3), which stimulation can be provided at the same time, before, or after treatment with an anti-TIGIT antibody. For example, provided herein are methods of enhancing an antigen-specific T cell response comprising contacting said T cell with an anti-TIGIT antibody described herein, and optionally with CD3, such that an antigen-specific T cell response is enhanced, e.g. by removal of a TIGIT-mediated inhibitory effect. Any suitable indicator of an antigen-specific T cell response can be used to measure the antigen-specific T cell response. Non-limiting examples of such suitable indicators include increased T cell proliferation in the presence of the antibody and/or increase cytokine production in the presence of the antibody. In a preferred embodiment, interleukin-2 and/or interferon-γ production by the antigen-specific T cell is enhanced.

Further encompassed are methods of enhancing an immune response (e.g., an antigen-specific T cell response) in a subject comprising administering an anti-TIGIT antibody described herein to the subject such that an immune response (e.g., an antigen-specific T cell response) in the subject is enhanced. In a preferred embodiment, the subject is a tumor-bearing subject and an immune response against the tumor is enhanced. A tumor may be a solid tumor or a liquid tumor, e.g., a hematological malignancy. In certain embodiments, a tumor is an immunogenic tumor. In certain embodiments, a tumor is non-immunogenic. In certain embodiments, a tumor is PD-L1 positive. In certain embodiments a tumor is PD-L1 negative. A subject may also be a virus-bearing subject and an immune response against the virus is enhanced.

Further provided are methods for inhibiting growth of tumor cells in a subject comprising administering to the subject an anti-TIGIT antibody described herein such that growth of the tumor is inhibited in the subject. Also provided are methods of treating chronic viral infection in a subject comprising administering to the subject an anti-TIGIT antibody described herein such that the chronic viral infection is treated in the subject.

Also encompassed herein are methods for depleting $T_{reg}$ cells from the tumor microenvironment of a subject having a tumor, e.g., cancerous tumor, comprising administering to the subject a therapeutically effective amount of an anti-TIGIT antibody described herein that comprises an Fc that stimulates depletion of $T_{reg}$ cells in the tumor microenvironment. An Fc may, e.g., be an Fc with effector function or enhanced effector function, such as binding or having enhanced binding to one or more activating Fc receptors. In a preferred embodiment, $T_{reg}$ depletion occurs without significant depletion or inhibition of $T_{eff}$ in the tumor microenvironment, and without significant depletion or inhibition of $T_{eff}$ cells and $T_{reg}$ cells outside of the tumor microenvironment. In certain embodiments, the subject has higher levels of TIGIT on $T_{reg}$ cells than on $T_{eff}$ cells, e.g., in the tumor microenvironment. In certain embodiments, anti-TIGIT antibodies may deplete Tregs in tumors and/or Tregs in tumor infiltrating lymphocytes (TILs). For example, in the CT26 tumor model, an anti-mouse TIGIT antibody formatted as a mouse IgG2a (which exhibits effector function) partially depleted both $T_{reg}$ and CD8$^+$ T cells, but did not deplete CD4$^+$ T cells. An effectorless counterpart anti-TIGIT antibody, formatted as a mouse IgG1 D265A, did not deplete T cells. When considering whether or not to use an having effector function or an effectorless anti-TIGIT antibody due consideration must be paid to the tradeoff between depletion of $T_{regs}$, which may enhance anti-tumor immune response, and depletion of CD8$^+$ T cells, which would eliminate some of the cells needed to actually kill tumor cells. Although depletion of $T_{regs}$ might be expected to enhance anti-tumor activity, recent studies have demonstrated that ligation of TIGIT on TIGIT+$T_{regs}$ promotes $T_{reg}$ cell-mediated suppression of $T_{eff}$ cell proliferation (Joller et al. (2014) *Immunity* 40:569), suggesting that blocking of TIGIT signaling (e.g. using an antagonist anti-TIGIT antibody of the present invention) might also enhance anti-tumor activity. Accordingly, it may be most efficacious to use an antagonist anti-TIGIT antibody lacking effector function, which i) blocks TIGIT signaling in $T_{regs}$ thus reducing their immunesuppresive activity, ii) activates anti-tumor CD8$^+$ T cells by blocking TIGIT's inhibitory effects, while at the same time avoiding their effector-function-mediated depletion, and iii) enhances DNAM-mediated activation by allowing DNAM to bind to PVR that would otherwise have been bound by TIGIT (and by reducing direct TIGIT-DNAM interactions) (Johnston et al. (2014) *Cancer Cell* 26:923).

In certain embodiments, an anti-TIGIT antibody is given to a subject as an adjunctive therapy. Treatments of subjects having cancer with an anti-TIGIT antibody may lead to a long-term durable response relative to the current standard of care; long term survival of at least 1, 2, 3, 4, 5, 10 or more years, recurrence free survival of at least 1, 2, 3, 4, 5, or 10 or more years. In certain embodiments, treatment of a subject having cancer with an anti-TIGIT antibody prevents recurrence of cancer or delays recurrence of cancer by, e.g., 1, 2, 3, 4, 5, or 10 or more years. An anti-TIGIT treatment can be used as a primary or secondary line of treatment.

These and other methods described herein are discussed in further detail below.

Cancer

Blocking of PVR/Nectin-2 signaling through TIGIT by anti-TIGIT antibodies can enhance the immune response to cancerous cells in the patient. Provided herein are methods for treating a subject having cancer, comprising administering to the subject an anti-TIGIT antibody described herein, such that the subject is treated, e.g., such that growth of cancerous tumors is inhibited or reduced and/or that the tumors regress. An anti-TIGIT antibody can be used alone to inhibit the growth of cancerous tumors. Alternatively, an anti-TIGIT antibody can be used in conjunction with another agent, e.g., other immunogenic agents, standard cancer treatments, or other antibodies, as described below. Combination with an inhibitor of PD-1, such as an anti-PD-1 or anti-PD-L1 antibody, is also provided.

Accordingly, provided herein are methods of treating cancer, e.g., by inhibiting growth of tumor cells, in a subject, comprising administering to the subject a therapeutically effective amount of an anti-TIGIT antibody described herein, e.g., 15A6, 22G2, 11G11 or 10D7, or antigen-binding fragment thereof. The antibody may be a human anti-TIGIT antibody (such as any of the human anti-huTIGIT antibodies described herein), or it may be a chimeric or humanized non-human anti-huTIGIT antibody, e.g., a chimeric or humanized anti-TIGIT antibody that competes for binding with, or binds to the same epitope as, at least one of the anti-TIGIT antibodies described herein.

Cancers whose growth may be inhibited using the antibodies of the invention include cancers typically responsive to immunotherapy. Non-limiting examples of cancers for treatment include squamous cell carcinoma, small-cell lung cancer, non-small cell lung cancer, squamous non-small cell lung cancer (NSCLC), non NSCLC, glioma, gastrointestinal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (M0), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. The methods described herein may also be used for treatment of metastatic cancers, refractory cancers (e.g., cancers refractory to previous immunotherapy, e.g., with a blocking CTLA-4 or PD-1 antibody), and recurrent cancers.

An anti-TIGIT antibody can be administered as a monotherapy, or as the only immunostimulating therapy, or it can be combined with an immunogenic agent, such as cancerous cells, purified tumor antigens (including recombinant proteins, peptides, and carbohydrate molecules), or cells transfected with genes encoding immune stimulating cytokines, in a cancer vaccine strategy (He et al. (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita et al. (eds.), 1997, Cancer: Principles and Practice of Oncology, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci. U.S.A.* 90: 3539-43).

The study of gene expression and large scale gene expression patterns in various tumors has led to the definition of so called tumor specific antigens (Rosenberg, S A (1999) *Immunity* 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. TIGIT inhibition can be used in conjunction with a collection of recombinant proteins and/or peptides expressed in a tumor in order to generate an immune response to these proteins. These proteins are normally viewed by the immune system as self antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) *Science* 266: 2011-2013). Tumor antigen can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen that can be used in conjunction with TIGIT inhibition is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) *Science* 269:1585-1588; Tamura et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle et al. (1998) *Nature Medicine* 4: 328-332). DCs can also be transduced by genetic means to express these tumor antigens as well. DCs have also been fused directly to tumor cells for the purposes of immunization (Kugler et al. (2000) *Nature Medicine* 6:332-336). As a method of vaccination, DC immunization can be effectively combined with TIGIT blocking to activate (unleash) more potent anti-tumor responses.

TIGIT inhibition can also be combined with standard cancer treatments (e.g., surgery, radiation, and chemotherapy). TIGIT inhibition can be effectively combined with chemotherapeutic regimes. In these instances, it may be possible to reduce the dose of chemotherapeutic reagent administered (Mokyr et al. (1998) *Cancer Research* 58: 5301-5304). An example of such a combination is an anti-TIGIT antibody in combination with decarbazine for the treatment of melanoma. Another example of such a combination is an anti-TIGIT antibody in combination with interleukin-2 (IL-2) for the treatment of melanoma. The scientific rationale behind the combined use of TIGIT inhibition and chemotherapy is that cell death, that is a consequence of the cytotoxic action of most chemotherapeutic compounds, should result in increased levels of tumor antigen in the antigen presentation pathway. Other combination therapies that may result in synergy with TIGIT inhibition through cell death are radiation, surgery, and hormone deprivation. Each of these protocols creates a source of tumor antigen in the host. Angiogenesis inhibitors can also be combined with TIGIT inhibition. Inhibition of angiogenesis leads to tumor cell death, which may feed tumor antigen into host antigen presentation pathways.

The anti-TIGIT antibodies described herein can also be used in combination with bispecific antibodies that target Fcα or Fcγ receptor-expressing effectors cells to tumor cells (see, e.g., U.S. Pat. Nos. 5,922,845 and 5,837,243). Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would be augmented by the inhibition of TIGIT. Alternatively, antigen may be delivered directly to DCs by the use of bispecific antibodies that bind to tumor antigen and a dendritic cell specific cell surface marker.

Tumors evade host immune surveillance by a large variety of mechanisms. Many of these mechanisms may be overcome by the inactivation of immunosuppressive proteins expressed by the tumors. These include among others TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). Antibodies to each of these entities can be used in combination with anti-TIGIT antibodies to counteract the effects of the immunosuppressive agent and favor tumor immune responses by the host.

Other antibodies that activate host immune responsiveness can be used in combination with anti-TIGIT antibodies. These include molecules on the surface of dendritic cells that activate DC function and antigen presentation. Anti-CD40 antibodies are able to substitute effectively for T cell helper activity (Ridge et al. (1998) *Nature* 393: 474-478) and can be used in conjunction with anti-TIGIT antibodies. Activating antibodies to T cell costimulatory molecules such as OX-40 (Weinberg et al. (2000) *Immunol* 164: 2160-2169), CD137/4-1BB (Melero et al. (1997) *Nature Medicine* 3: 682-685 (1997), and ICOS (Hutloff et al. (1999) *Nature* 397: 262-266) may also provide for increased levels of T cell activation. Inhibitors of PD-1 or PD-L1, or CTLA-4 (e.g., U.S. Pat. No. 5,811,097), may also be used in conjunction with anti-TIGIT antibodies.

Bone marrow transplantation is currently being used to treat a variety of tumors of hematopoietic origin. While graft versus host disease is a consequence of this treatment, therapeutic benefit may be obtained from graft vs. tumor responses. TIGIT inhibition can be used to increase the effectiveness of the donor engrafted tumor specific T cells.

There are also several experimental treatment protocols that involve ex vivo activation and expansion of antigen specific T cells and adoptive transfer of these cells into recipients in order to stimulate antigen-specific T cells against tumor (Greenberg & Riddell (1999) *Science* 285: 546-51). These methods can also be used to activate T cell responses to infectious agents such as CMV. Ex vivo activation in the presence of anti-TIGIT antibodies can increase the frequency and activity of the adoptively transferred T cells.

Chronic Viral Infections

In another aspect, the invention described herein provides a method of treating an infectious disease in a subject comprising administering to the subject an anti-TIGIT antibody, or antigen-binding fragment thereof, such that the subject is treated for the infectious disease.

Similar to its application to tumors as discussed above, antibody-mediated TIGIT inhibition can be used alone, or as an adjuvant, in combination with vaccines, to enhance the immune response to pathogens, toxins, and self-antigens. Examples of pathogens for which this therapeutic approach can be particularly useful include, but are not limited to, HIV, Hepatitis (A, B, & C), Influenza, Herpes, *Giardia*, Malaria, *Leishmania, Staphylococcus aureus, Pseudomonas aeruginosa*. TIGIT inhibition is particularly useful against established infections by agents such as HIV that present altered antigens over the course of the infections. These novel epitopes are recognized as foreign at the time of anti-human TIGIT antibody administration, thus provoking a strong T cell response.

Some examples of pathogenic viruses causing infections treatable by methods described herein include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods described herein include chlamydia, rickettsial bacteria, mycobacteria, staphylococci, streptococci, pneumonococci, meningococci and gonococci, *Klebsiella, Proteus, Serratia, Pseudomonas, Legionella*, diphtheria, *Salmonella*, bacilli, cholera, tetanus, botulism, anthrax, plague, leptospirosis, and Lymes disease bacteria.

Some examples of pathogenic fungi causing infections treatable by methods described herein include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizopus*), *Sporothrix schenkii, Blastomyces dermatitides, Paracoccidioides brasiliensis, Coccidioides immitis* and *Histoplasma capsulatum*.

Some examples of pathogenic parasites causing infections treatable by methods described herein include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia micron, Trypanosoma brucei, Trypanosoma cruzi, Leishmania donovani, Toxoplasma gondii, Nippostrongylus brasiliensis*.

In all of the above methods, TIGIT inhibition can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) *Proc. Natl. Acad. Sci. USA* 90:6444-6448; Poljak (1994) *Structure* 2:1121-1123).

Vaccine Adjuvants

Anti-TIGIT antibodies described herein can be used to enhance antigen-specific immune responses by co-administration of an anti-TIGIT antibody with an antigen of interest (e.g., a vaccine). Accordingly, provided herein are methods of enhancing an immune response to an antigen in a subject, comprising administering to the subject: (i) the antigen; and (ii) an anti-TIGIT antibody, or antigen-binding fragment thereof, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

In certain embodiments, a peptide or fusion protein comprising the epitope to which an anti-TIGIT antibody binds is used as a vaccine instead of, or in addition to, an anti-TIGIT antibody.

Suitable routes of administering the antibody compositions (e.g., human monoclonal antibodies, multispecific and bispecific molecules and immunoconjugates) described herein in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, anti-TIGIT antibodies described herein can be co-administered with one or other more therapeutic agents, e.g., a cytotoxic agent, a radiotoxic agent or an immunosuppressive agent. The antibody can be linked to the agent (as an immuno-complex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, dacarbazine and cyclophosphamide hydroxyurea which, by themselves, are only effective at levels that are toxic or subtoxic to a patient. Cisplatin is intravenously administered as a 100 mg/ml dose once every four weeks and adriamycin is intravenously administered as a 60-75 mg/ml dose once every 21 days. Co-administration of anti-TIGIT antibodies, or antigen binding fragments thereof, described herein with chemotherapeutic agents provides two anti-cancer agents that operate via different mechanisms to yield a cytotoxic effect to human tumor cells. Such co-administration can solve problems due to development of resistance to drugs or a change in the antigenicity of the tumor cells that would render them unreactive with the antibody.

Also within the scope described herein are kits comprising the antibody compositions described herein (e.g., human antibodies, bispecific or multispecific molecules, or immunoconjugates) and instructions for use. The kit can further contain at least one additional reagent, or one or more additional human antibodies described herein (e.g., a human antibody having a complementary activity that binds to an epitope in TIGIT antigen distinct from the first human antibody). Kits typically include a label indicating the intended use of the contents of the kit. The term label includes any writing, or recorded material supplied on or with the kit, or which otherwise accompanies the kit.

Combination Therapies

In addition to the combinations therapies provided above, anti-TIGIT antibodies described herein can also be used in combination therapy, e.g., for treating cancer, as described below.

The present invention provides methods of combination therapy in which an anti-TIGIT antibody is co-administered with one or more additional agents, e.g., antibodies, that are effective in stimulating immune responses to thereby further enhance, stimulate or upregulate immune responses in a subject. As shown in Example 7, and shown in FIGS. 5A and 5B, administration of an antagonist anti-TIGIT antibody and an antagonist anti-PD-1 antibody to mice had an enhanced effect in inhibiting tumor growth.

Generally, an anti-TIGIT antibody described herein can be combined with (i) an agonist of a co-stimulatory receptor and/or (ii) an antagonist of an inhibitory signal on T cells, either of which results in amplifying antigen-specific T cell responses (immune checkpoint regulators). Most of the co-stimulatory and co-inhibitory molecules are members of the immunoglobulin super family (IgSF), and anti-TIGIT antibodies described herein may be administered with an agent that targets a member of the IgSF family to increase an immune response. One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which include CD40 and CD40L, OX-40, OX-40L, CD70, CD27L, CD30, CD30L, 4-1BBL, CD137/4-1BB, TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR (see, e.g., Tansey (2009) *Drug Discovery Today* 00:1).

T cell activation is also regulated by soluble cytokines. Thus, anti-TIGIT antibodies can be used in combination with (i) antagonists (or inhibitors or blocking agents) of proteins of the IgSF family or B7 family or the TNF family that inhibit T cell activation or antagonists of cytokines that inhibit T cell activation (e.g., IL-6, IL-10, TGF-β, VEGF, or other immunosuppressive cytokines) and/or (ii) agonists of stimulatory receptors of the IgSF family, B7 family or the TNF family or of cytokines that stimulate T cell activation, for stimulating an immune response, e.g., for treating proliferative diseases, such as cancer.

In one aspect, T cell responses can be stimulated by a combination of the anti-TIGIT mAbs of the present invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, CD113, GPR56, VISTA, 2B4, CD48, GARP, PD1H, LAIR1, TIM-1, CD96 (WO 2015/024060; Bernhardt et al. (2014) *Nat. Immunol.* 15:406) and TIM-4, and (ii) an agonist of a protein that stimulates T cell activation such as B7-1, B7-2, CD28, 4-1BB (CD137), 4-1BBL, ICOS, CD40, ICOS-L, OX40, OX40L, GITR, GITRL, CD70, CD27, CD40, DR3 and CD28H.

Exemplary agents that modulate one of the above proteins and may be combined with agonist anti-TIGIT antibodies, e.g., those described herein, for treating cancer, include: YERVOY®/ipilimumab or tremelimumab (to CTLA-4), galiximab (to B7.1), OPDIVO®/nivolumab/BMS-936558 (to PD-1), pidilizumab/CT-011 (to PD-1), KEYTRUDA®/pembrolizumab/MK-3475 (to PD-1), AMP224 (to B7-DC/PD-L2), BMS-936559 (to B7-H1), MPDL3280A (to B7-H1), MEDI-570 (to ICOS), AMG557 (to B7H2), MGA271 (to B7H3—WO 11/109400), IMP321 (to LAG-3), urelumab/BMS-663513 and PF-05082566 (to CD137/4-1BB), CDX-1127 (to CD27), MEDI-6383 and MEDI-6469 (to OX40), RG-7888 (to OX40L—WO 06/029879), Atacicept (to TACI), CP-870893 (to CD40), lucatumumab (to CD40), dacetuzumab (to CD40), and muromonab-CD3 (to CD3).

Other molecules that can be combined with antagonist anti-TIGIT antibodies for the treatment of cancer include antagonists of inhibitory receptors on NK cells or agonists of activating receptors on NK cells. For example, antagonist anti-TIGT antibodies can be combined with antagonists of MR (e.g., lirilumab).

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

Generally, antagonist anti-TIGIT antibodies described herein can be used together with one or more of agonistic agents that ligate positive co-stimulatory receptors, blocking agents that attenuate signaling through inhibitory receptors, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit $T_{reg}$s (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

Provided herein are methods for stimulating an immune response in a subject comprising administering to the subject an antagonist anti-TIGIT molecule, e.g., an antibody, and one or more additional immunostimulatory antibodies, such as a PD-1 antagonist, e.g., antagonist antibody, a PD-L1 antagonist, e.g., antagonist antibody, a CTLA-4 antagonist, e.g., antagonist antibody and/or a LAG3 antagonist, e.g., an antagonist antibody, such that an immune response is stimulated in the subject, for example to inhibit tumor growth or to stimulate an anti-viral response. In one embodiment, the subject is administered an antagonist anti-TIGIT antibody and an antagonist anti-PD-1 antibody. In one embodiment, the subject is administered an antagonist anti-TIGIT antibody and an antagonist anti-PD-L1 antibody. In one embodiment, the subject is administered an antagonist anti-TIGIT antibody and an antagonist anti-CTLA-4 antibody. In one embodiment, the at least one additional immunostimulatory antibody (e.g., anti-PD-1, anti-PD-L1, anti-CTLA-4 and/or anti-LAG3) is a human antibody. Alternatively, the at least one additional immunostimulatory antibody can be, for example, a chimeric or humanized antibody, e.g., prepared from a mouse anti-PD-1, anti-PD-L1, anti-CTLA-4 and/or anti-LAG3 antibody.

Provided herein are methods for treating a hyperproliferative disease (e.g., cancer), comprising administering an antagonist anti-TIGIT antibody and an antagonist PD-1 antibody to a subject. TIGIT and PD-1 are co-expressed in melanoma (Chauvin et al. (2015) *J. Clin. Invest.* 125:2046), and are also co-expressed at relatively high levels on $CD8^+$ TILS from non-small cell lung cancer (NSCLC) and renal cell carcinoma (RCC) patients. See Table 2 (showing the percentage of $TIGIT^+/PD-1^+$ cells as a percentage of total $CD3^+$ $CD8^+$ TILS for samples from several patients).

TABLE 2

Percentage TIGIT+/PD-1+ TILS in Cancers

| Sample | % TIGIT+/PD-1+ |
|---|---|
| NSCLC-1 | 13 |
| NSCLC-3 | 5.8 |
| NSCLC-4 | 37.4 |
| NSCLC-5 | 14.6 |
| NSCLC-6 | 49.1 |
| NSCLC-7 | 57.8 |
| NSCLC-8 | 50.5 |
| NSCLC-9 | 21 |
| RCC-002 | 25.5 |
| RCC-003 | 65.6 |
| RCC-006 | 20.5 |

In certain embodiments, the anti-TIGIT antibody is administered at a subtherapeutic dose, the anti-PD-1 antibody is administered at a subtherapeutic dose, or both are administered at a subtherapeutic dose. Also provided herein are methods for altering an adverse event associated with treatment of a hyperproliferative disease with an immunostimulatory agent, comprising administering an anti-TIGIT antibody and a subtherapeutic dose of anti-PD-1 antibody to a subject. In certain embodiments, the subject is human. In certain embodiments, the anti-PD-1 antibody is a human sequence monoclonal antibody and the anti-TIGIT antibody is human sequence monoclonal antibody, such as an antibody comprising the CDRs or variable regions of the antibodies disclosed herein.

In one embodiment, only subjects with tumors exhibiting high expression of PVR and/or Nectin-2 and high expression PD-L1 are selected for combination treatment with the anti-TIGIT antibody of the present invention and a PD-1 antagonist. In another embodiment, subjects with tumors exhibiting high expression of PVR and/or Nectin-2 but low expression PD-L1 are selected for monotherapy with anti-TIGIT antibodies of the present invention, or combination therapy with another therapeutic agent other than the PD-1 antagonist.

In other embodiments, the present invention provides combination therapy in which the anti-TIGIT antibody of the present invention is administered subsequent to treatment with the PD-1/PD-L1 antagonist. In one embodiment, anti-TIGIT antibodies are administered only after treatment with a PD-1/PD-L1 antagonist has failed, led to incomplete therapeutic response, or there has been recurrence of the tumor or relapse (referred to herein as "PD-1 failures"). In a further embodiment, tumors in such PD-1 failures are screened for expression of PVR and/or Nectin-2 and only those having high level expression are treated with anti-TIGIT antibodies.

Suitable PD-1 antagonists for use in the methods described herein, include, without limitation, ligands, antibodies (e.g., monoclonal antibodies and bispecific antibodies), and multivalent agents. In one embodiment, the PD-1 antagonist is a fusion protein, e.g., an Fc fusion protein, such as AMP-244. In one embodiment, the PD-1 antagonist is an anti-PD-1 or anti-PD-L1 antibody.

An exemplary anti-PD-1 antibody is OPDIVO®/ nivolumab (BMS-936558) or an antibody that comprises the CDRs or variable regions of one of antibodies 17D8, 2D3, 4H1, 5C4, 7D3, 5F4 and 4A11 described in WO 2006/121168. In certain embodiments, an anti-PD-1 antibody is MK-3475 (KEYTRUDA®/pembrolizumab/formerly lambrolizumab) described in WO2012/145493; AMP-514/MEDI-0680 described in WO 2012/145493; and CT-011 (pidilizumab; previously CT-AcTibody or BAT; see, e.g., Rosenblatt et al. (2011) J. Immunotherapy 34:409). Further known PD-1 antibodies and other PD-1 inhibitors include those described in WO 2009/014708, WO 03/099196, WO 2009/114335, WO 2011/066389, WO 2011/161699, WO 2012/145493, U.S. Pat. Nos. 7,635,757 and 8,217,149, and U.S. Patent Publication No. 2009/0317368. Any of the anti-PD-1 antibodies disclosed in WO2013/173223 may also be used. An anti-PD-1 antibody that competes for binding with, and/or binds to the same epitope on PD-1 as, as one of these antibodies may also be used in combination treatments.

Provided herein are methods for treating a hyperproliferative disease (e.g., cancer), comprising administering an antagonist anti-TIGIT antibody and an antagonist PD-L1 antibody to a subject. In certain embodiments, the anti-TIGIT antibody is administered at a subtherapeutic dose, the anti-PD-L1 antibody is administered at a subtherapeutic dose, or both are administered at a subtherapeutic dose. Provided herein are methods for altering an adverse event associated with treatment of a hyperproliferative disease with an immunostimulatory agent, comprising administering an anti-TIGIT antibody and a subtherapeutic dose of anti-PD-L1 antibody to a subject. In certain embodiments, the subject is human. In certain embodiments, the anti-PD-L1 antibody is a human sequence monoclonal antibody and the anti-TIGIT antibody is human sequence monoclonal antibody, such as an antibody comprising the CDRs or variable regions of the antibodies disclosed herein.

In one embodiment, the anti-PD-L1 antibody is BMS-936559 (referred to as 12A4 in WO 2007/005874 and U.S. Pat. No. 7,943,743), MSB0010718C (WO2013/79174), or an antibody that comprises the CDRs or variable regions of 3G10, 12A4, 10A5, 5F8, 10H10, 1B12, 7H1, 11E6, 12B7 and 13G4, which are described in PCT Publication WO 07/005874 and U.S. Pat. No. 7,943,743. In certain embodiment an anti-PD-L1 antibody is MEDI4736 (also known as Anti-B7-H1) or MPDL3280A (also known as RG7446). Any of the anti-PD-L1 antibodies disclosed in WO2013/173223, WO2011/066389, WO2012/145493, U.S. Pat. Nos. 7,635,757 and 8,217,149 and U.S. Publication No. 2009/145493 may also be used. Anti-PD-L1 antibodies that compete with and/or bind to the same epitope as that of any of these antibodies may also be used in combination treatments.

In yet further embodiment, the agonist anti-huCD40 antibody of the present invention is combined with an antagonist of PD-1/PD-L1 signaling, such as a PD-1 antagonist or a PD-L1 antagonist, in combination with a third immunotherapeutic agent. In one embodiment the third immunotherapeutic agent is a GITR antagonist or an OX-40 antagonist, such as the anti-GITR or anti-OX40 antibodies disclosed herein.

In another aspect, the immuno-oncology agent is a GITR agonist, such as an agonistic GITR antibody. Suitable GITR antibodies include, for example, BMS-986153, BMS-986156, TRX-518 (WO 06/105021, WO 09/009116) and MK-4166 (WO 11/028683).

In another aspect, the immuno-oncology agent is an IDO antagonist. Suitable IDO antagonists include, for example, INCB-024360 (WO 2006/122150, WO 07/75598, WO 08/36653, WO 08/36642), indoximod, or NLG-919 (WO 09/73620, WO 09/1156652, WO 11/56652, WO 12/142237).

Provided herein are methods for treating a hyperproliferative disease (e.g., cancer), comprising administering an anti-TIGIT antibody described herein and a CTLA-4 antagonist antibody to a subject. In certain embodiments, the anti-TIGIT antibody is administered at a subtherapeutic dose, the anti-CTLA-4 antibody is administered at a subtherapeutic dose, or both are administered at a subtherapeutic dose. Provided herein are methods for altering an adverse event associated with treatment of a hyperproliferative disease with an immunostimulatory agent, comprising administering an anti-TIGIT antibody and a subtherapeutic dose of anti-CTLA-4 antibody to a subject. In certain embodiments, the subject is human. In certain embodiments, the anti-CTLA-4 antibody is an antibody selected from the group consisting of: YERVOY® (ipilimumab or antibody 10D1, described in PCT Publication WO 01/14424), tremelimumab (formerly ticilimumab, CP-675,206), and the anti-CTLA-4 antibody described in the following publications: WO 98/42752; WO 00/37504; U.S. Pat. No. 6,207,156; Hurwitz et al. (1998) *Proc. Natl. Acad. Sci. USA* 95(17): 10067-10071; Camacho et al. (2004) *J. Clin. Oncology* 22(145): Abstract No. 2505 (antibody CP-675206); and Mokyr et al. (1998) *Cancer Res.* 58:5301-5304. Any of the anti-CTLA-4 antibodies disclosed in WO2013/173223 may also be used.

Provided herein are methods for treating a hyperproliferative disease (e.g., cancer), comprising administering an anti-TIGIT antibody and an anti-LAG-3 antibody to a subject. In further embodiments, the anti-TIGIT antibody is administered at a subtherapeutic dose, the anti-LAG-3 antibody is administered at a subtherapeutic dose, or both are administered at a subtherapeutic dose. Provide herein are methods for altering an adverse event associated with treatment of a hyperproliferative disease with an immunostimulatory agent, comprising administering an anti-TIGIT antibody and a subtherapeutic dose of anti-LAG-3 antibody to a subject. In certain embodiments, the subject is human. In certain embodiments, the anti-LAG-3 antibody is a human sequence monoclonal antibody and the anti-TIGIT antibody is human sequence monoclonal antibody, such as an antibody comprising the CDRs or variable regions of the antibodies disclosed herein. Examples of anti-LAG3 antibodies include antibodies comprising the CDRs or variable regions of antibodies 25F7, 26H10, 25E3, 8B7, 11F2 or 17E5, which are described in U.S. Patent Publication No. US2011/0150892 and WO2014/008218. In one embodiment, an anti-LAG-3 antibody is BMS-986016. Other art recognized anti-LAG-3 antibodies that can be used include IMP731 described in US 2011/007023. IMP-321 may also be used. Anti-LAG-3 antibodies that compete with and/or bind to the same epitope as that of any of these antibodies may also be used in combination treatments.

Administration of anti-TIGIT antibodies described herein and antagonists, e.g., antagonist antibodies, to one or more second target antigens such as LAG-3 and/or CTLA-4 and/or PD-1 and/or PD-L1 can enhance the immune response to cancerous cells in the patient. Cancers whose growth may be inhibited using the antibodies of the instant disclosure include cancers typically responsive to immunotherapy. Representative examples of cancers for treatment with the combination therapy of the instant disclosure include those cancers specifically listed above in the discussion of monotherapy with anti-TIGIT antibodies.

In certain embodiments, the combination of therapeutic antibodies discussed herein can be administered concurrently as a single composition in a pharmaceutically acceptable carrier, or concurrently as separate compositions with each antibody in a pharmaceutically acceptable carrier. In another embodiment, the combination of therapeutic antibodies can be administered sequentially. For example, an anti-CTLA-4 antibody and an anti-TIGIT antibody can be administered sequentially, such as anti-CTLA-4 antibody being administered first and anti-TIGIT antibody second, or anti-TIGIT antibody being administered first and anti-CTLA-4 antibody second. Additionally or alternatively, an anti-PD-1 antibody and an anti-TIGIT antibody can be administered sequentially, such as anti-PD-1 antibody being administered first and anti-TIGIT antibody second, or anti-TIGIT antibody being administered first and anti-PD-1 antibody second. Additionally or alternatively, an anti-PD-L1 antibody and an anti-TIGIT antibody can be administered sequentially, such as anti-PD-L1 antibody being administered first and anti-TIGIT antibody second, or anti-TIGIT antibody being administered first and anti-PD-L1 antibody second. Additionally or alternatively, an anti-LAG-3 antibody and an anti-TIGIT antibody can be administered sequentially, such as anti-LAG-3 antibody being administered first and anti-TIGIT antibody second, or anti-TIGIT antibody being administered first and anti-LAG-3 antibody second.

Furthermore, if more than one dose of the combination therapy is administered sequentially, the order of the sequential administration can be reversed or kept in the same order at each time point of administration, sequential administrations can be combined with concurrent administrations, or any combination thereof. For example, the first administration of a combination anti-CTLA-4 antibody and anti-TIGIT antibody can be concurrent, the second administration can be sequential with anti-CTLA-4 antibody first and anti-TIGIT antibody second, and the third administration can be sequential with anti-TIGIT antibody first and anti-CTLA-4 antibody second, etc. Additionally or alternatively, the first administration of a combination anti-PD-1 antibody and anti-TIGIT antibody can be concurrent, the second administration can be sequential with anti-PD-1 antibody first and anti-TIGIT antibody second, and the third administration can be sequential with anti-TIGIT antibody first and anti-PD-1 antibody second, etc. Additionally or alternatively, the first administration of a combination anti-PD-L1 antibody and anti-TIGIT antibody can be concurrent, the second administration can be sequential with anti-PD-L1 antibody first and anti-TIGIT antibody second, and the third administration can be sequential with anti-TIGIT antibody first and anti-PD-L1 antibody second, etc. Additionally or alternatively, the first administration of a combination anti-LAG-3 antibody and anti-TIGIT antibody can be concurrent, the second administration can be sequential with anti-LAG-3 antibody first and anti-TIGIT antibody second, and the third administration can be sequential with anti-TIGIT antibody first and anti-LAG-3 antibody second, etc. Another representative dosing scheme can involve a first administration that is sequential with anti-TIGIT first and anti-CTLA-4 antibody (and/or anti-PD-1 antibody and/or anti-PD-L1 antibody and/or anti-LAG-3 antibody) second, and subsequent administrations may be concurrent.

Optionally, an anti-TIGIT as sole immunotherapeutic agent, or the combination of an anti-TIGIT antibody and one or more additional immunotherapeutic antibodies (e.g., anti-CTLA-4 and/or anti-PD-1 and/or anti-PD-L1 and/or anti-LAG-3 blockade) can be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below). A TIGIT inhibitor and one or more additional antibodies (e.g., CTLA-4 and/or PD-1 and/or PD-L1 and/or LAG-3 blockade) can also be further combined with standard cancer treatments. For example, a TIGIT inhibitor and one or more additional antibodies (e.g., CTLA-4 and/or PD-1 and/or PD-L1 and/or LAG-3 blockade) can be effectively combined with chemotherapeutic regimes. In these instances, it is possible to reduce the dose of other chemotherapeutic reagent administered with the combination of the instant disclosure (Mokyr et al. (1998) *Cancer Research* 58: 5301-5304). An example of such a combination is a combination of anti-TIGIT agonist antibody with or without and an additional antibody, such as anti-CTLA-4 antibodies and/or anti-PD-1 antibodies and/or anti-PD-L1 antibodies and/or anti-LAG-3 antibodies) further in combination with decarbazine for the treatment of melanoma. Another example is a combination of anti-TIGIT antibody with or without and anti-CTLA-4 antibodies and/or anti-PD-1 antibodies and/or anti-PD-L1 antibodies and/or LAG-3 antibodies further in combination with interleukin-2 (IL-2) for the treatment of melanoma. The scientific rationale behind the combined use of TIGIT inhibition and CTLA-4 and/or PD-1 and/or PD-L1 and/or LAG-3 blockade with chemotherapy is that cell death, which is a consequence of the cytotoxic action of most chemotherapeutic compounds, should result in increased levels of tumor antigen in the antigen presentation pathway. Other combination therapies that may result in synergy with a combined TIGIT inhibition with or without and CTLA-4 and/or PD-1 and/or PD-L1 and/or LAG-3 blockade through cell death include radiation, surgery, or hormone deprivation. Each of these protocols creates a source of tumor antigen in the host. Angiogenesis inhibitors can also be combined with a combined TIGIT inhibition and CTLA-4 and/or PD-1 and/or PD-L1 and/or LAG-3 blockade. Inhibition of angiogenesis leads to tumor cell death, which can be a source of tumor antigen fed into host antigen presentation pathways.

An anti-TIGIT antagonist antibody as sole immunotherapeutic agent, or a combination of TIGIT antagonistic and CTLA-4 and/or PD-1 and/or PD-L1 and/or LAG-3 blocking antibodies can also be used in combination with bispecific antibodies that target Fcα or Fcγ receptor-expressing effector cells to tumor cells (see, e.g., U.S. Pat. Nos. 5,922,845 and 5,837,243). Bispecific antibodies can be used to target two separate antigens. The T cell arm of these responses would be augmented by the use of a combined TIGIT inhibition and CTLA-4 and/or PD-1 and/or PD-L1 and/or LAG-3 blockade.

In another example, an anti-TIGIT antagonist antibody as sole immunotherapeutic agent or a combination of an anti-TIGIT antibody and additional immunostimulating agent, e.g., anti-CTLA-4 antibody and/or anti-PD-1 antibody and/or anti-PD-L1 antibody and/or LAG-3 agent, e.g., antibody, can be used in conjunction with an anti-neoplastic antibody, such as RITUXAN® (rituximab), HERCEPTIN® (trastuzumab), BEXXAR® (tositumomab), ZEVALIN® (ibritumomab), CAMPATH® (alemtuzumab), LYMPHOCIDE® (epratuzumab), AVASTIN® (bevacizumab), and TARCEVA® (erlotinib), and the like. By way of example and not wishing to be bound by theory, treatment with an anti-cancer antibody or an anti-cancer antibody conjugated to a toxin can lead to cancer cell death (e.g., tumor cells) which would potentiate an immune response mediated by the immunostimulating agent, e.g., TIGIT, CTLA-4, PD-1, PD-L1 or LAG-3 agent, e.g., antibody. In an exemplary embodiment, a treatment of a hyperproliferative disease (e.g., a cancer tumor) can include an anti-cancer agent, e.g., antibody, in combination with anti-TIGIT and optionally an additional immunostimulating agent, e.g., anti-CTLA-4 and/or anti-PD-1 and/or anti-PD-L1 and/or anti-LAG-3 agent, e.g., antibody, concurrently or sequentially or any combination thereof, which can potentiate an anti-tumor immune responses by the host.

Tumors evade host immune surveillance by a large variety of mechanisms. Many of these mechanisms may be overcome by the inactivation of proteins, which are expressed by the tumors and which are immunosuppressive. These include, among others, TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). Antibodies to each of these entities can be further combined with an anti-TIGIT antibody with or without an additional immunostimulating agent, e.g., an anti-CTLA-4 and/or anti-PD-1 and/or anti-PD-L1 and/or anti-LAG-3 agent, such as antibody, to counteract the effects of immunosuppressive agents and favor anti-tumor immune responses by the host.

Other agents, e.g., antibodies, that can be used to activate host immune responsiveness can be further used in combination with an anti-TIGIT antibody with or without an additional immunostimulating agent, such as anti-CTLA-4 and/or anti-PD-1 and/or anti-PD-L1 and/or anti-LAG-3 antibody. These include molecules on the surface of dendritic cells that activate DC function and antigen presentation. Anti-CD40 antibodies (Ridge et al., supra) can be used in conjunction with an anti-TIGIT antibody and optionally an additional immunostimulating agent, e.g., an anti-CTLA-4 and/or anti-PD-1 and/or anti-PD-L1 and/or anti-LAG-3 agent, e.g., antibody. Other activating antibodies to T cell co-stimulatory molecules OX-40 (Weinberg et al. (2000) *Immunol* 164:2160-2169), CD137/4-1BB (Melero et al. (1997) *Nature Medicine* 3:682-685 (1997), and ICOS (Hutloff et al. (1999) *Nature* 397:262-266) may also provide for increased levels of T cell activation.

As discussed above, bone marrow transplantation is currently being used to treat a variety of tumors of hematopoietic origin. Anti-TIGIT immunotherapy alone or combined with CTLA-4 and/or PD-1 and/or PD-L1 and/or LAG-3 blockade can be used to increase the effectiveness of the donor engrafted tumor specific T cells.

Several experimental treatment protocols involve ex vivo activation and expansion of antigen specific T cells and adoptive transfer of these cells into recipients in order to antigen-specific T cells against tumor (Greenberg & Riddell, supra). These methods can also be used to activate T cell responses to infectious agents such as CMV. Ex vivo activation in the presence of anti-TIGIT with or without an additional immunostimulating therapy, e.g., anti-CTLA-4 and/or anti-PD-1 and/or anti-PD-L1 and/or anti-LAG-3 antibodies can be expected to increase the frequency and activity of the adoptively transferred T cells.

Provided herein are methods for altering an adverse event associated with treatment of a hyperproliferative disease (e.g., cancer) with an immunostimulatory agent, comprising administering an anti-TIGIT antibody with or without and a subtherapeutic dose of anti-CTLA-4 and/or anti-PD-1 and/or anti-PD-L1 and/or anti-LAG-3 agent, e.g., antibody, to a subject. For example, the methods described herein provide for a method of reducing the incidence of immunostimulatory therapeutic antibody-induced colitis or diarrhea by administering a non-absorbable steroid to the patient. As used herein, a "non-absorbable steroid" is a glucocorticoid that exhibits extensive first pass metabolism such that, following metabolism in the liver, the bioavailability of the steroid is low, i.e., less than about 20%. In one embodiment described herein, the non-absorbable steroid is budesonide. Budesonide is a locally-acting glucocorticosteroid, which is extensively metabolized, primarily by the liver, following oral administration. ENTOCORT EC® (Astra-Zeneca) is a pH- and time-dependent oral formulation of budesonide developed to optimize drug delivery to the ileum and throughout the colon. ENTOCORT EC® is approved in the U.S. for the treatment of mild to moderate Crohn's disease involving the ileum and/or ascending colon. The usual oral dosage of ENTOCORT EC® for the treatment of Crohn's disease is 6 to 9 mg/day. ENTOCORT EC® is released in the intestines before being absorbed and retained in the gut mucosa. Once it passes through the gut mucosa target tissue, ENTOCORT EC® is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT EC® can result in systemic glucocorticoid effects such as hypercorticism and adrenal suppression. See PDR 58th ed. 2004; 608-610.

In still further embodiments, a TIGIT inhibition with or without CTLA-4 and/or PD-1 and/or PD-L1 and/or LAG-3 blockade (i.e., immunostimulatory therapeutic antibodies anti-TIGIT and optionally anti-CTLA-4 and/or anti-PD-1 and/or anti-PD-L1 and/or anti-LAG-3 antibodies) in conjunction with a non-absorbable steroid can be further combined with a salicylate. Salicylates include 5-ASA agents such as, for example: sulfasalazine (AZULFIDINE®, Pharmacia & UpJohn); olsalazine (DIPENTUM®, Pharmacia & UpJohn); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

In accordance with the methods described herein, a salicylate administered in combination with anti-TIGIT with or without anti-CTLA-4 and/or anti-PD-1 and/or anti-PD-L1 and/or LAG-3 antibodies and a non-absorbable steroid can includes any overlapping or sequential administration of the salicylate and the non-absorbable steroid for the purpose of decreasing the incidence of colitis induced by the immunostimulatory antibodies. Thus, for example, methods for reducing the incidence of colitis induced by the immunostimulatory antibodies described herein encompass administering a salicylate and a non-absorbable steroid concurrently or sequentially (e.g., a salicylate is administered 6 hours after a non-absorbable steroid), or any combination thereof. Further, a salicylate and a non-absorbable steroid can be administered by the same route (e.g., both are administered orally) or by different routes (e.g., a salicylate is administered orally and a non-absorbable steroid is administered rectally), which may differ from the route(s) used to administer the anti-TIGIT and anti-CTLA-4 and/or anti-PD-1 and/or anti-PD-L1 and/or anti-LAG-3 antibodies.

The anti-TIGIT antibodies and combination antibody therapies described herein may also be used in conjunction with other well-known therapies that are selected for their particular usefulness against the indication being treated (e.g., cancer). Combinations of the anti-TIGIT antibodies described herein may be used sequentially with known pharmaceutically acceptable agent(s).

For example, the anti-TIGIT antibodies and combination antibody therapies described herein can be used in combination (e.g., simultaneously or separately) with an additional treatment, such as irradiation, chemotherapy (e.g., using camptothecin (CPT-11), 5-fluorouracil (5-FU), cisplatin, doxorubicin, irinotecan, paclitaxel, gemcitabine, cisplatin, paclitaxel, carboplatin-paclitaxel (Taxol), doxorubicin, 5-fu, or camptothecin+apo2l/TRAIL (a 6× combo)), one or more proteasome inhibitors (e.g., bortezomib or MG132), one or more Bcl-2 inhibitors (e.g., BH3I-2' (bcl-xl inhibitor), indoleamine dioxygenase-1 (IDO1) inhibitor (e.g., INCB24360), AT-101 (R-(−)-gossypol derivative), ABT-263 (small molecule), GX-15-070 (obatoclax), or MCL-1 (myeloid leukemia cell differentiation protein-1) antagonists), iAP (inhibitor of apoptosis protein) antagonists (e.g., smac7, smac4, small molecule smac mimetic, synthetic smac peptides (see Fulda et al., Nat Med 2002; 8:808-15), ISIS23722 (LY2181308), or AEG-35156 (GEM-640)), HDAC (histone deacetylase) inhibitors, anti-CD20 antibodies (e.g., rituximab), angiogenesis inhibitors (e.g., bevacizumab), anti-angiogenic agents targeting VEGF and VEGFR (e.g., AVASTIN®), synthetic triterpenoids (see Hyer et al., Cancer Research 2005; 65:4799-808), c-FLIP (cellular FLICE-inhibitory protein) modulators (e.g., natural and synthetic ligands of PPARγ (peroxisome proliferator-activated receptor γ), 5809354 or 5569100), kinase inhibitors (e.g., Sorafenib), trastuzumab, cetuximab, Temsirolimus, mTOR inhibitors such as rapamycin and temsirolimus, Bortezomib, JAK2 inhibitors, HSP90 inhibitors, PI3K-AKT inhibitors, Lenalildomide, GSK3β inhibitors, IAP inhibitors and/or genotoxic drugs.

The anti-TIGIT antibodies and combination antibody therapies described herein can further be used in combination with one or more anti-proliferative cytotoxic agents. Classes of compounds that may be used as anti-proliferative cytotoxic agents include, but are not limited to, the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN™) fosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Suitable anti-proliferative agents for combining with antagonist anti-TIGIT antibodies, without limitation, taxanes, paclitaxel (paclitaxel is commercially available as TAXOL™), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone B1, [17]-dehydrodesoxyepothilone B, [18]dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone B10, discoderomolide, patupilone (EPO-906), KOS-862, KOS-1584, ZK-EPO, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptophycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14,16-didemethyl-(+)-discodermolides, and cryptothilone 1, in addition to other microtubuline stabilizing agents known in the art.

In cases where it is desirable to render aberrantly proliferative cells quiescent in conjunction with or prior to treatment with anti-TIGIT antibodies described herein, hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, ZOLADEX™, can also be administered to the patient. When employing the methods or compositions described herein, other agents used in the modulation of tumor growth or metastasis in a clinical setting, such as antimimetics, can also be administered as desired.

Methods for the safe and effective administration of chemotherapeutic agents are known to those skilled in the art. In addition, their administration is described in the standard literature. For example, the administration of many of the chemotherapeutic agents is described in the Physicians' Desk Reference (PDR), e.g., 1996 edition (Medical Economics Company, Montvale, N.J. 07645-1742, USA); the disclosure of which is incorporated herein by reference thereto.

The chemotherapeutic agent(s) and/or radiation therapy can be administered according to therapeutic protocols well known in the art. It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

Patient Selection

Figure 6A:
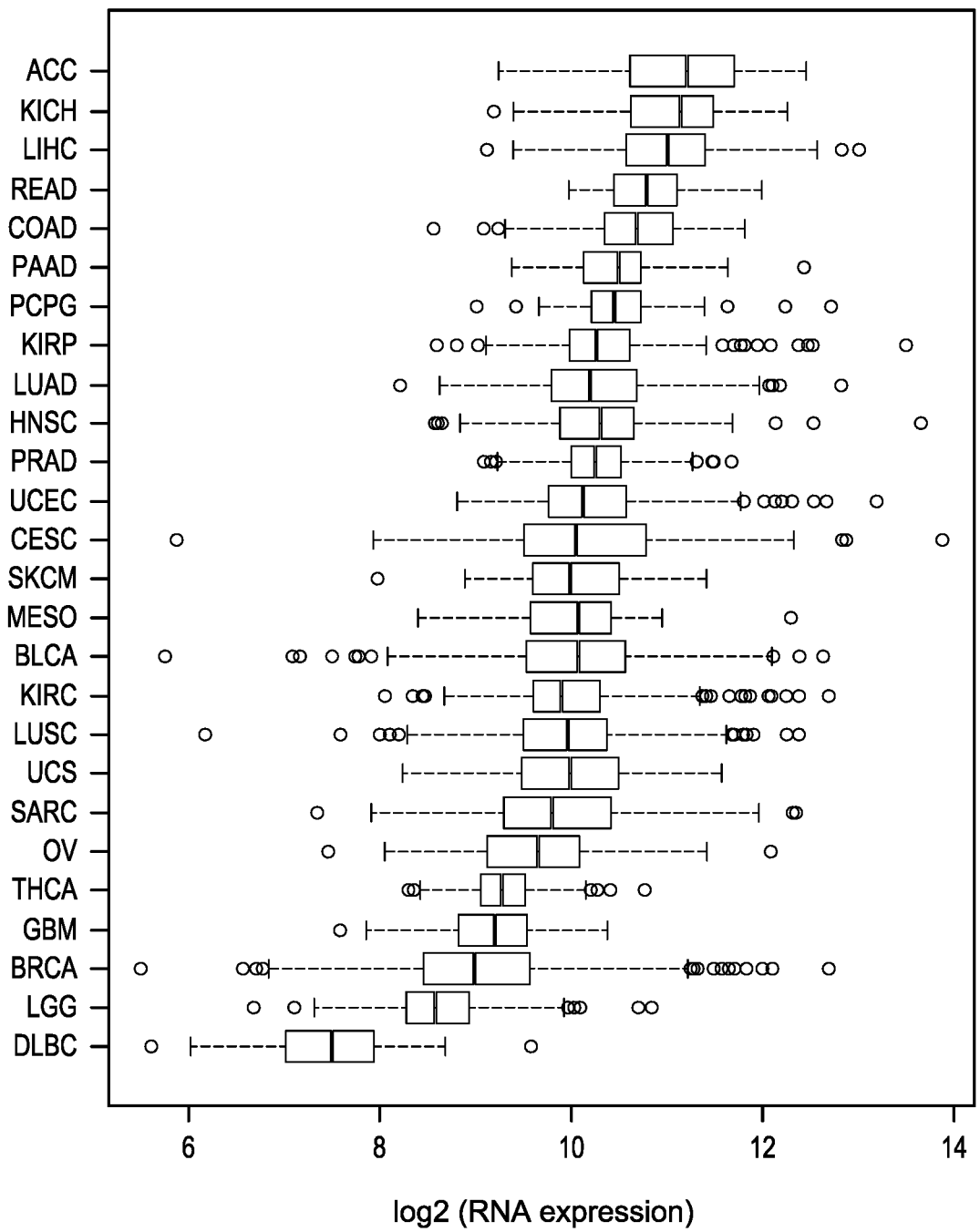
FIGS. 6A and 6B show elevated PVR expression in cancer tissues.

In various embodiments of the present invention, patients are tested prior to being treated with anti-TIGIT antibodies of the present invention to determine whether they are likely to respond to anti-TIGIT therapy, and only those exhibiting traits associated with a therapeutic response are treated. Expression of proteins associated with the TIGIT pathway, including TIGIT, DNAM, PVR, Nectin-2, soluble PVR (sPVR) and soluble Nectin-2 (sNectin-2), or combinations thereof, may be measured. PVR and Nectin-2 mRNA are both highly expressed in the majority of human tumors. See Example 9, and FIG. 6A. In one embodiment sPVR and/or sNectin-2 are detected in human serum, for example by ELISA, wherein elevated sPVR and/or sNectin-2 levels are indicative of subjects having a cancer that is likely to respond to treatment with anti-TIGIT antibodies of the present invention.

In some embodiments, samples from patients are screened for expression of DNAM-1 on T cells to select patients most likely to respond to anti-TIGIT therapy, wherein the presence of DNAM-1 on T cells or NK cells suggests a the patient will have a beneficial anti-tumor response upon anti-TIGIT therapy, e.g. treatment with the anti-huTIGIT antibody or fragment of the present invention, and the absence of DNAM-1 on T cells or NK cells identifies patients that are less likely to benefit from anti-TIGIT therapy. In other embodiments, samples from patients are screened for expression of PVR and/or Nectin-2/CD112 on tumor cells or tumor-infiltrating myeloid cells to select patients most likely to respond to anti-TIGIT therapy, wherein the presence of PVR and/or Nectin-2/CD112 on tumor cells or tumor-infiltrating myeloid cells suggests a the patient will have a beneficial anti-tumor response upon anti-TIGIT therapy, e.g. treatment with the anti-huTIGIT antibody or fragment of the present invention, and the absence of PVR and/or Nectin-2/CD112 on tumor cells or tumor-infiltrating myeloid cells identifies patients that are less likely to benefit from anti-TIGIT therapy.

In one embodiment, the level of soluble PVR and/or Nectin-2 is measured in subjects being considered for treatment with anti-TIGIT antibodies of the present invention, and only subjects exhibiting elevated soluble PVR and/or Nectin-2 are treated with the antibodies. For example, high soluble PVR and/or Nectin-2 may be used as a patient selection biomarker.

Tumor types, and tumors in individual subjects, are most likely to respond to treatment with the anti-TIGIT antibodies of the present invention if the tumor cells express elevated levels of PVR and/or Nectin-2, and also if such tumors have high levels of infiltrating TIGIT$^+$ CD8$^+$ T cells.

XI. Exemplary Embodiments

Various embodiments of the present invention are provided in the following numbered paragraphs.

1. An isolated antibody, or antigen binding fragment thereof, that competes for binding to human TIGIT (T cell immunoreceptor with Ig and ITIM domains) with one or more antibodies selected from the group consisting of 14B2, 13E6, 6F9, 11G11, 10C9, 16F6, 11C9, 27A9, 10D7, 20G6, 24E8, 24G1, 27F1, 15A6, 4E4, 13D1, 9B11, 10B8, 22G2, 19H2, 8C8, 17G4, 25E7, 26D8 and 16A8.

2. The isolated antibody or fragment of Embodiment 1, wherein the competition in a cross-blocking assay comprises the ability to reduce binding of the selected antibody to human TIGIT (SEQ ID NO: 1) in a competition ELISA by at least 20% when used at a roughly equal molar concentration with the selected antibody.

3. An isolated antibody, or antigen binding fragment thereof, that binds to TIGIT (human T cell immunoreceptor with Ig and ITIM domains) at:
   a) an epitope comprising one or more of residues E60, I109, L65, N70, F107, T117, I68, H76 and N58 (antibody 22G2) of huTIGIT (SEQ ID NO: 1);
   b) an epitope comprising one or more of residues G74, N70, H76, L65, L73, Q56, I68, H111 and P114 (antibody 11G11); or
   c) an epitope comprising one or more of residues H76, G74, L65, N58, I68, Q139, G135, L73, F107, N70, E60, H134, A132 and I109 (antibody 15A6).

4. The isolated antibody or fragment of Embodiment 3 that binds to TIGIT at an epitope comprising one or more of residues L65, I68, N70 and H76.

5. The isolated antibody or fragment of Embodiment 3 that binds to TIGIT at:
   a) an epitope comprising the sequence NWEQQDQLLA-ICNADLGWH (SEQ ID NO: 38) and/or FCIYH-TYPDGT (SEQ ID NO: 39) (antibody 22G2);
   b) an epitope comprising the sequence QVNWEQQDQL-LAICNADLGWH (SEQ ID NO: 40) and/or HTYP (SEQ ID NO: 41) (antibody 11G11); or
   c) an epitope comprising the sequence NWEQQDQLLA-ICNADLGWH (SEQ ID NO: 38), FCI, and/or AEHGARFQ (SEQ ID NO: 43) (antibody 15A6).

6. The isolated antibody or fragment of Embodiment 5 that binds to TIGIT at an epitope comprising the sequence LLAICNADLGWH (SEQ ID NO: 44).

7. An isolated antibody, or antigen binding fragment thereof, that binds to TIGIT (human T cell immunoreceptor with Ig and ITIM domains) wherein the antibody heavy chain variable domain is derived from human V region germline sequence V4-39, V4-61, or V1-69.

8. The isolated antibody or fragment of Embodiment 7, wherein the antibody heavy and light chain variable domains are derived from human heavy and light chain V region germline sequence combinations V4-39/VA27, V4-61/VL6, V4-39/VL6 or V1-69NL15.

9. The isolated antibody or fragment of any one of the preceding embodiments wherein the antibody or fragment substantially inhibits the binding of human TIGIT to human PVR/CD155.

10. The isolated antibody or fragment of any one of Embodiments 1-8 wherein the antibody binds to human TIGIT with a $K_D$ of 2 nM or less as measured by BIA-CORE® SPR analysis.

11. The isolated antibody or fragment of any one of Embodiments 1-8 wherein the antibody binds to both human and cynomolgus TIGIT.

12. The isolated antibody or fragment of any one of the preceding embodiments wherein the antibody is not mAb 10A7 or 1F4 of U.S. Pat. Ap. Pub. No. 2009/0258013.

13. The isolated antibody or fragment of Embodiment 12, wherein the antibody or fragment does not bind to the same epitope on huTIGIT as, and does not compete for binding to TIGIT with, mAb 10A7 or 1F4 of U.S. Pat. Ap. Pub. No. 2009/0258013.

14. An isolated antibody, or antigen binding fragment thereof, that binds to TIGIT (human T cell immunoreceptor with Ig and ITIM domains) consisting essentially of:
   a) a heavy chain variable domain comprising:
      i) CDRH1 comprising the sequence of SEQ ID NO.:14, 20, 26, or 32;
      ii) CDRH2 comprising the sequence of SEQ ID NO.: 15, 21, 27, or 33; and
      iii) CDRH3 comprising the sequence of SEQ ID NO.: 16, 22, 28, or 34; and
   b) a light chain variable domain comprising:
      iv) CDRL1 comprising the sequence of SEQ ID NO.: 17, 23, 29, or 35;
      v) CDRL2 comprising the sequence of SEQ ID NO.:18, 24, 30, or 36; and
      vi) CDRL3 comprising the sequence of SEQ ID NO.: 19, 25, 31, or 37.

15. The isolated antibody or fragment of Embodiment 14 comprising one or more heavy chains and one or more light chains, wherein:
   a) the heavy chain comprises a heavy chain variable region having at least 80% sequence identity with the sequence of SEQ ID NOs: 2, 3, 4, 5, 7, 8, 10 or 12; and
   b) the light chain comprises a light chain variable region having at least 80% sequence identity with the sequence of SEQ ID NOs: 6, 9, 11, or 13.

16. The isolated antibody or fragment of Embodiment 14 comprising heavy and light chain variable domains comprising a specific combination of CDRH1, CDRH2, CDRH3, CDRL1, CDRL2 and CDRL3 sequences selected from the group consisting of:
   a) SEQ ID NOs: 14-19 (antibody 15A6);
   b) SEQ ID NOs: 20-25 (antibody 22G2);
   c) SEQ ID NOs: 26-31 (antibody 11G11); and
   d) SEQ ID NOs: 32-37 (antibody 10D7).

17. The isolated antibody or fragment of any one of the preceding embodiments wherein the antibody is a human IgG1 antibody or variant thereof having increased effector function.

18. The isolated antibody of any one of Embodiments 11-16 wherein the antibody is a human IgG1 Fc variant with reduced or eliminated effector function.

19. The isolated antibody or fragment Embodiment 18 comprising the following mutations: L234A, L235E, G237A, A330S and P331S (SEQ ID NO: 48) by EU numbering.

20. A nucleic acid encoding the heavy and/or light chain variable region of the antibody or fragment of any of the preceding embodiments.

21. An expression vector comprising the nucleic acid of Embodiment 20.

22. A host cell transformed with an expression vector of Embodiment 21.

23. A method of producing an anti-TIGIT antibody or antigen binding fragment thereof comprising culturing the host cell of Embodiment 22 under conditions that allows production of the antibody or fragment, and purifying the antibody from the cell.

24. A method of enhancing an antigen-specific T cell response in a subject in need thereof comprising contacting the T cell with the antibody or fragment of any one of Embodiments 1-19 such that an antigen-specific T cell response is enhanced.

25. The method of Embodiment 24 wherein the subject has a tumor or a chronic viral infection and an immune response against the tumor or viral infection is enhanced.

26. A method of reducing or depleting regulatory T cells in a tumor of a subject in need thereof comprising administering an effective amount of an antibody or fragment of any one of Embodiments 1-17 such that the number of regulatory T cells in a tumor is reduced.

27. A method of treating cancer comprising administering to a subject in need thereof a therapeutically effective amount of the antibody or fragment of any one of Embodiments 1-19.

28. The method of Embodiment 27, wherein the cancer is selected from the group consisting of: bladder cancer, breast cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, and virus-related cancer.

29. The method of Embodiment 27 wherein the cancer is a metastatic cancer, refractory cancer, or recurrent cancer.

30. The method of any one of Embodiments 24-29 further comprising administering one or more additional therapeutic agent selected from the group consisting of an anti-PD-1 antibody, an anti-LAG-3 antibody, an anti-CTLA-4 antibody, or an anti-PD-L1 antibody.

31. The method of Embodiment 30, wherein the additional therapeutic agent is anti-PD-1 antibody.

32. The method of Embodiment 30, wherein the additional therapeutic agent is an anti-PD-L1 antibody.

33. A bispecific antibody comprising a first antigen binding domain and a second antigen binding domain, wherein:
   a) the first antigen binding domain is from an anti-huTIGIT antibody of any one of Embodiments 1-16; and
   b) the second antigen binding domain is from an antibody selected from the group consisting of an anti-PD-1 antibody, an anti-LAG-3 antibody, an anti-CTLA-4 antibody, and an anti-PD-L1 antibody.

34. The bispecific antibody of Embodiment 33, wherein the second binding domain is from an anti-PD-1 antibody.

35. The bispecific antibody of Embodiment 33, wherein the second binding domain is from an anti-PD-L1 antibody.

36. A method of detecting the presence of TIGIT in a sample comprising contacting the sample with the antibody, or antigen binding fragment thereof, of any one of Embodiments 1-16 under conditions that allow for formation of a complex between the antibody, or antigen binding fragment thereof, and TIGIT, and detecting the formation of the complex.

37. A method of treating cancer comprising administering an antagonist anti-TIGIT antibody, or antigen binding fragment thereof, to a subject having a tumor if and only if the tumor comprises one or more of the following:
   a) high levels of infiltrating TIGIT$^+$ T cells and/or NK cells;
   b) elevated expression of PVR and/or Nectin-2 on tumor cells or tumor infiltrating myeloid cells; and
   c) a *Fusobacterium nucleatum* infection.

38. A method of treating cancer comprising administering an antagonist anti-TIGIT antibody of any one of Embodiments 1-19, or antigen binding fragment thereof, to a subject having a tumor if and only if the tumor comprises one or more of the following:
   a) high levels of infiltrating TIGIT$^+$ T cells and/or NK cells;
   b) elevated expression of PVR and/or Nectin-2 on tumor cells or tumor infiltrating myeloid cells; and
   c) a *Fusobacterium nucleatum* infection.

The present disclosure is further illustrated by the following examples, which should not be construed as further limiting. The contents of all figures and all references, Genbank sequences, patents and published patent applications cited throughout this application are expressly incorporated herein by reference. In particular, the disclosures of PCT publications WO 09/045957, WO 09/073533, WO 09/073546, WO 09/054863 and PCT/US2013/072918, and U.S. Patent Publication No. 2011/0150892 are expressly incorporated herein by reference.

EXAMPLES

Example 1

Generation of Anti-huTIGIT Antibodies

Human anti-huTIGIT monoclonal antibodies were generated using transgenic mice that express human antibody genes, as follows.

Antigen

A huTIGIT soluble recombinant protein was used as the antigen for immunizations. The soluble fusion protein has a MW of 40.7 kD and is composed of the extracellular portion of huTIGIT linked to a mouse IgG2a Fc at its C-terminus. This fusion protein is referred to herein as "huTIGIT-muFc fusion protein." The fusion protein was generated by standard recombinant DNA methods and expressed in transfected CHO cells, which secreted the soluble fusion protein into the culture supernatant. The CHO host cells used for transfection were obtained from Invitrogen (Cat #11619-012). The secreted soluble fusion protein was purified for use as immunogen. The sequence of full length human TIGIT including signal sequence is provided at SEQ ID NO: 1.

Transgenic Mice

Fully human monoclonal antibodies to human TIGIT were prepared using mice from the CHD;CKD2; CMD++;JKD++;KCo5(9272)+^;SC20+ genotype (hereafter called KM® mice). Individual transgene designations are in parentheses, followed by line numbers for randomly integrated transgenes. The symbols ++ and + indicate homozygous or hemizygous; however, because the mice are routinely screened using a PCR-based assay that does not allow us to distinguish between heterozygosity and homozygosity for the randomly integrated human Ig transgenes, a + designation may be given to mice that are actually homozygous for these elements. In this strain, the endogenous mouse kappa light chain gene has been homozygously disrupted as described in Chen et al. (1993) *EMBO J.* 12:811-820 and the endogenous mouse heavy chain gene has been homozygously disrupted as described in example 1 of WO 2001/09187. Furthermore, this mouse strain carries a human kappa light chain transgene, KCo5, as described in Fishwild et al. (1996) *Nature Biotechnology* 14:845-851, a yeast artificial chromosome (YAC) carrying most of the human kappa light chain locus, as described in WO 2000/026373.

Immunization of Mice

To generate fully human monoclonal antibodies to human TIGIT, KM mice were immunized with purified huTIGIT-muFc fusion protein. General immunization schemes are described in Lonberg, N. et al (1994) Nature 368(6474): 856-859; Fishwild, D. et al. (1996) Nature Biotechnology 14: 845-851 and WO 98/24884. The mice were approximately 4 months of age upon the first infusion of antigen. Either purified recombinant huTIGIT-muFc antigen preparation (10 μg purified from transfected mammalian cells expressing the fusion protein) or 300-19 cells transfected with human TIGIT were used to immunize the mice intraperitoneally and subcutaneously. The immunogens were mixed 1:1 with RIBI adjuvant (Sigma Cat #M6536).

The mice were immunized 5 times at 5-7 day intervals. The first and second immunizations were performed with the recombinant protein. The third immunization was with the cells, the 4th immunization with the protein and the 5th immunization with the cells. Mice were bled one week after the last immunizations to assess antigen specific titers. The immune response was monitored by retro orbital bleeds. The plasma was screened by FACS analysis using the transfected 300-19 cells, and mice with highest titers for anti-human TIGIT human IgG were used for fusions. Mice received a final boost by intravenous (IV) and intraperitoneal (IP) injection of soluble antigen 2 days and transfected cells 3 days before sacrifice and removal of the spleen.

Generation of Hybridomas Producing Human Monoclonal Antibodies to Human TIGIT

Mouse splenocytes isolated from high titer KM mice and a mouse myeloma fusion partner were fused with an electric field based electrofusion using a Cyto Pulse large chamber cell fusion electroporator (Cyto Pulse Sciences, Inc., Glen Burnie, MD). Single cell suspensions of splenic lymphocytes from immunized mice were fused to an equal number of P3X63 Ag8.6.53 (ATCC CRL 1580) non secreting mouse myeloma cells (fusion number: 2541). Resulting cells were plated at $2.0 \times 10^4$ cells/well in flat bottom microtiter plates in selective DMEM medium containing high glucose (Cellgro #10-013-CM) and 10% fetal calf serum (Hyclone #SH30071.03), and supplemented with beta-mercaptoethanol (1000×, Gibco #21985-023), 7 mM HEPES (Cellgro 25-060-C1), additional 2 mM L-glutamine (Cellgro 25-005-Cl), HAT (50×, Sigma #H-0262), 5% Hybridoma Cloning Factor (BioVeris #210001), 10% P388DI (ATCC #CRL TIB-63) conditioned medium and Penicillin-Streptomycin (100×, Cellgro #30-002-Cl). After about 7 days, some of the medium containing HAT was replaced with medium containing HT (Cellgro #25-047-CI).

After 10 to 12 days, individual wells were screened for the presence of human IgG/human kappa light chain antibodies using a homogenous HTRF assay. In this assay, supernatants from 96 well fusion plates were mixed with Europium-cryptate labeled goat anti-human IgG (Fc fragment specific), biotinylated goat anti-human kappa light chain (Bethyl #A80-115B), streptavidin-XLent and incubated for 1 hour. The plates were then read on a RUBYstar reader.

Hybridoma cells from wells positive for human IgG/human kappa light chain or human IgG/human lambda light chain antibodies were then screened by FACS using 300-19 cells transfected with human TIGIT and 300-19 untransfected cells as control. FACS positive parental lines were transferred to 24-well plates. A few days later, cell supernatants from individual wells were rescreened by FACS to confirm IgG specificity to human TIGIT.

The hybridomas were cloned by serial dilution and rescreened by FACS. Thirty six antibodies were selected for expansion and purification. Four antibodies (15A6, 22G2, 11G11, 10D7) were subsequently selected for sequencing and further analysis.

Example 2

Binding of Anti-huTIGIT Antibodies to Soluble Human TIGIT

Binding of anti-huTIGIT antibodies to soluble human TIGIT was determined by BIACORE® surface plasmon resonance (SPR) analysis. Anti-huTIGIT antibodies were captured on human kappa coated chips (~5KRUs; Southernbiotech cat #2060-01), and recombinant human TIGIT (rhTIGIT/Fc) was flowed across the chip at concentrations of 500 nM, 250 nM, 125 nM, 62 nM, and 31 nM. The capture concentration of the mAb/volume was 2-40 μg/mL (5 μl at 10 μL/min). The antigen association time was 5 minutes at 15 μL/min, the antigen dissociation time was 6 minutes, and regeneration was performed with 50 mM HCl/50 mM NaOH (12 μL each at 100 μL/min). Results are shown in Table 3.

TABLE 3

Binding of anti-huTIGIT mAbs to human TIGIT

| Antibody | $k_a$ ($M^{-1}s^{-1}$) ($\times 10^5$) | $k_d$ ($s^{-1}$) ($\times 10^{-3}$) | $K_D$ (nM) |
|---|---|---|---|
| 22G2 | 23.7 | 0.403 | 0.17 |
| 24E8 | 2.19 | 0.704 | 3.22 |
| 10B8 | 4.19 | 4.27 | 10.2 |
| 26F7 | 1.11 | 1.30 | 11.8 |
| 13D1 | 1.12 | 1.44 | 12.8 |
| 19H2 | 1.66 | 2.42 | 14.6 |
| 15A6 | 2.02 | 4.04 | 19.9 |
| 16F6 | 1.38 | 3.75 | 27.2 |
| 11G11 | 0.503 | 1.44 | 28.7 |
| 25E7 | 1.33 | 4.00 | 30.1 |
| 24G1 | 1.25 | 4.37 | 35.0 |
| 10D7 | 1.71 | 6.51 | 38.1 |
| 17G4 | 2.19 | 8.42 | 38.4 |
| 4E4 | 7.35 | 37.3 | 50.7 |
| 5F4 | 0.561 | 3.14 | 56.0 |
| 20G6 | 3.18 | 18.3 | 57.6 |
| 6F9 | 4.68 | 31.9 | 68.2 |
| 6F9 | 2.99 | 20.6 | 69.0 |
| 11C9 | 0.4 | 2.94 | 73.5 |
| 9B11 | 1.23 | 11.7 | 94.9 |
| 27F1 | 0.777 | 8.56 | 110 |
| 13E6 | 2.03 | 22.5 | 111 |
| 27F1 | 0.544 | 8.38 | 154 |
| 11G2 | 1.74 | 33.4 | 192 |
| 10C9 | 1.52 | 29.4 | 194 |
| 8C8 | 0.582 | 33.1 | 568 |

The binding of antibodies 14B2, 19H2 and 26D8 was too weak to be reliably measured.

The preliminary binding constant determination shown in Table 3 was used to help select anti-huTIGIT antibodies for further study. Binding constants for subcloned and purified antibodies 15A6 and 22G2 were then determined using full titration curves to be 1.5 nM and 90 pM, respectively.

Figure 7:
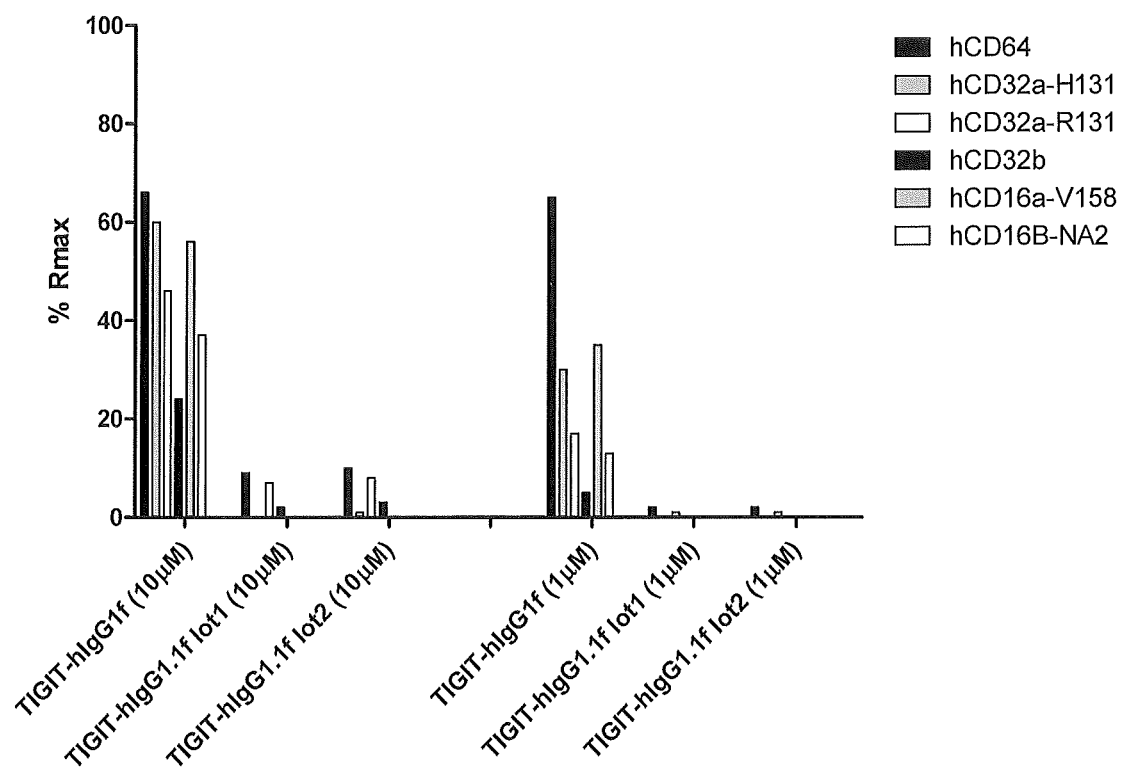
FIG. 7 shows Fcγ receptor binding, expressed as a percentage of the theoretical maximum receptor binding value ($R_{max}$), for anti-TIGIT mAb 22G2 formatted as an IgG1f (SEQ ID NO: 45) or an IgG1.1f (SEQ ID NO: 48). Data are presented for six different Fcγ receptors, for two different lots of IgG1.1f antibody, used at 10 µM and 1 µm, as indicated. Within each cluster of bars, the data for Fcγ receptors are presented in order, left to right: hCD64 (FcγRI); hCD32a-H131 (FcγRIIA-H131); hCD32a-R131 (FcγRIIA-R131); hCD32b (FcγRIIB); hCD16a-V158 (FcγRIIIA-V158); and hCD16b-NA2 (FcγRIIIB-NA2, where NA2 designates the allotypic variant). Although pairs of Fcγ receptors are represented by identical bars, their identities are clear from the order in which they are presented. The same decreases were observed for binding to cynomolgus monkey Fcγ receptors CD64, CD32a, CD32b, and CD16 (not shown).

Additional SPR experiments comparing 15A6 and 22G2 antibodies having modified framework residues and altered human IgG1 constant regions were performed. Human IgG1f sequence is provided at SEQ ID NO: 45, with an allotypic variant provided at SEQ ID NO: 46 (which differs from SEQ ID NO: 45 at R97K, E239D, and M241L). Human IgG1.3 is provided at SEQ ID NO: 47 (which differs from SEQ ID NO: 45 at L117A, L118E and G120A, which correspond to L234A, L235E and G237A under EU numbering). Another effectorless human IgG1 constant region, human IgG1.1f, is provided at SEQ ID NO: 48 (which differs from SEQ ID NO: 45 at L117A, L118E, G120A, A213S and P214S, which correspond to L234A, L235E, G237A, A330S and P331S under EU numbering). FIG. 7 shows the dramatic decrease in Fcγ receptor binding in IgG1.1f constructs. Use of such "inert" Fc regions may be advisable because TIGIT is highly expressed on CD8+ TILs, and anti-TIGIT antibodies having effector function might deplete the very anti-tumor CD8+ TILs and/or NK cells needed to eradicate the tumor.

SPR experiments comparing 15A6 having framework variants A72S and/or N112T, and 22G2 antibody having framework variant H3Q, to their unmodified forms demonstrated that neither the framework changes nor the isotype meaningfully effected binding to human TIGIT. Results are provided at Table 4.

TABLE 4

Binding of Selected Anti-huTIGIT mAbs to Human TIGIT

| Antibody | Sequence Variant | Isotype | $k_a$ ($M^{-1}s^{-1}$) ($\times 10^6$) | $k_d$ ($s^{-1}$) ($\times 10^{-3}$) | $K_D$ (nM) |
|---|---|---|---|---|---|
| 15A6 | — | IgG1f | 1.0 | 1.5 | 1.5 |
| 15A6 | — | IgG1.1f | 1.1 | 1.6 | 1.5 |
| 15A6 | A72S | IgG1.1f | 1.1 | 1.7 | 1.5 |
| 15A6 | N112T | IgG1.1f | 1.1 | 1.9 | 1.7 |
| 15A6 | A72S & N112T | IgG1.1f | 1.0 | 2.0 | 2.0 |
| 22G2 | — | IgG1f | 1.9 | 0.17 | 0.09 |
| 22G2 | — | IgG1.1f | 2.0 | 0.13 | 0.07 |
| 22G2 | H3Q | IgG1 | 1.9 | 0.30 | 0.16 |
| 22G2 | H3Q | IgG1.1f | 2.0 | 0.16 | 0.08 |

Additional SPR experiments found that mAb 22G2 bound to human TIGIT with $K_D$ of 0.06 nM and to cynomolgus monkey TIGIT with a $K_D$ of 0.09 nM.

Amino acid residue numbering in the Sequence Listing is 117 lower than the numbering in the literature due to use of EU numbering and to the absence of the variable domain in the IgG sequences in the Sequence Listing. The C-terminal lysine (K) residue present in the genetic constructs of human antibodies is often missing from commercially produced antibodies, such as therapeutic antibodies of the present invention. Dick et al. (2008) *Biotechnol. Bioeng.* 100:1132. Accordingly, this lysine is not included in any of SEQ ID NOs: 45-48, but in one embodiment, the anti-huTIGIT antibody of the present invention includes this additional lysine residue at the C-terminus of the heavy chain(s). In some embodiments the antibodies of the present invention are in preparations comprising a mixture of heavy chains having C-terminal lysine and heavy chains lacking C-terminal lysine, e.g. as the result of unintended C-terminal clipping. In some embodiments the anti-huTIGIT antibody of the present invention comprises one or more heavy chains and one or more light chains, such as two heavy chains and two light chains.

Example 3

Anti-TIGIT Antibodies Bin into Multiple Groups

Antibody binning experiments were conducted to determine which anti-human TIGIT antibodies complete with which others for binding to huTIGIT, and thus bind to similar epitopes. Antibodies 14B2, 13E6, 6F9, 11G11, 10C9, 16F6, 11C9, 27A9, 10D7, 20G6, 24E8, 24G1, 27F1, 15A6, 4E4, 13D1, 9B11, 10B8, 22G2, 19H2, 8C8, 17G4, 25E7, 26D8 and 16A8 were studied.

Pairwise competition between anti-huTIGIT antibodies was determined as follows, in which a first antibody is bound to the surface of a sensor chip, a second antibody is pre-incubated with a TIGIT polypeptide construct in a mixture, and the pre-incubated mixture is flowed over the sensor chip to determine the degree to which the second antibody interferes with binding of the TIGIT polypeptide construct to the first antibody on the chip surface. Briefly, first anti-huTIGIT antibodies were immobilized onto Sensor Chip CM5 chip (Series S, GE Healthcare CAT #BR-1005-30) surfaces, flowcell2, flowcell3 & flowcell4 (5000 RUs), and flowcell1 was used as a negative control. Second antibodies were diluted to 120 µg/mL (2×) at starting concentration. A series of dilutions of the second antibodies were made by diluting 1:3 concentration of antibody with buffer for seven different concentrations and a control sample with (0.0 µg/ml)—to obtain a titration curve. Each antibody concentration series was divided into two halves. In the first half of the concentration series, 40 nM (2×) TIGIT antigen (rhTIGIT/Fc) was added to make the final concentration series (60 µg/ml-0.0 µg/ml) and 20 nM of final antigen concentration in each well. In the second half of the concentration series, in place of antigen, buffer was added to have the antibody diluted to the same concentration, and this half was treated as the blank. Complexes of the second anti-TIGIT antibodies and rhTIGIT/Fc were incubated for 2 hours. 40 µL complexes were injected on the antibody (first) coated surface at a 30 µL/min flow rate. A BIACORE® T200 surface plasmon resonance instrument was used and the running buffer was HBE-EP, GE Healthcare CAT #BR-1001-88, filtered degassed, 0.01M HEPES, pH7.4, 0.15 NaCl, 3 mM EDTA, 0.005% Surfactant P20. The surface was regenerated with 25 mM NaOH (Order code: BR-1003-58, GE Healthcare) at 100 µL/min for 5 seconds. The data was analyzed using Microsoft Excel where the concentration series of second antibodies were plotted against the corresponding response unit to obtain titration curves.

The results indicate that the tested antibodies bin into four groups. See FIG. 1. Antibodies in Bin 1 (14B2, 13E6, 6F9, 11G11, 10C9, 16F6, 11C9, 27A9, 10D7, 20G6, 24E8, 24G1, 27F1, 15A6, 4E4, 13D1, 9B11, 10B8) block binding of other antibodies within Bin 1, as well as 22G2, 19H2, 8C8 and 17G4. Antibodies in Bin 2 (25E7, 26D8, 16A8) block binding of other antibodies within Bin 2, as well as 22G2, 19H2 and 8C8. Antibodies 22G2, 19H2 and 8C8 (Bin 3) block binding of other antibodies in Bin 3, as well as antibodies in both of Bins 1 and 2, but not 17G4 (Bin 4). Antibody 17G4 blocks binding of the antibodies within Bin 1 but not any of the other antibodies.

Example 4

Epitope Mapping by Yeast Display

The epitopes for selected anti-huTIGIT antibodies of the present invention (clones 22G2, 11G11 and 15A6) were determined by displaying randomly mutagenized huTIGIT extracellular region variants on yeast, and sorting these yeast based on their failure to bind to particular antibodies. Selected yeast cells that failed to bind were amplified and subjected to additional rounds of selection based on their inability to bind to particular antibodies of the present invention. See, e.g., Chao et al. (2004) *J. Mol. Biol.* 342:539. Sequences for huTIGIT variants were determined for the resulting yeast and analyzed for the effects of each residue on antibody binding. The binding epitope for the antibodies of the present invention was determined as the loci within the huTIGIT sequence where single amino acid mutations disrupted binding to the anti-huTIGIT antibodies of the present invention.

Briefly, error-prone PCR was used to clone human TIGIT-encoding DNA into constructs allowing expression of the huTIGIT variants as the amino-terminal portions of fusion proteins further comprising a c-myc tag sequence and yeast cell wall protein Agα1p. Such constructs, when expressed in yeast (*Saccharomyces cerevisiae*), display the variant huTIGIT polypeptides on the surface of yeast cells, anchored to the cell surface by the Aga1p polypeptide. The c-myc tag can optionally be used as a positive control for display of huTIGIT-fusion proteins on a given yeast cell. Yeast cells were sorted by FACS, and those that expressed as properly folded huTIGIT-fusion proteins (as determined by binding of a control mouse anti-huTIGIT antibody detected by an allophycocyanin (APC)-labeled goat anti-mouse IgG secondary), but did not bind to the antibodies of the present invention (as determined by detection with a phycoerythrin (PE) labeled goat anti-human IgG as a secondary), were pooled, amplified, and used in subsequent rounds of selection. The huTIGIT sequence was determined for constructs from yeast remaining after several rounds of selection. Control experiments without anti-huTIGIT antibody selection confirmed good mutant coverage at each position along the huTIGIT sequence, and provided a baseline for normalizing the results obtained with the selected libraries.

Millions of high quality sequence reads were performed for each antibody selected population of huTIGIT mutant molecules. It was found that residue 60 was structurally tolerant to mutation, but mutants at this position did not bind to antibody 22G2, indicating that E60 is involved in the epitope. Similarly, residues I109, L65, N70, F107, T117, I68, H76 and N58 were also found to be important residues in the epitope for antibody 22G2. The epitope residues for 22G2 cluster into primary sequence regions comprising residues 58-76 (NWEQQDQLLAICNADLGWH; SEQ ID NO: 38) and residues 107-117 (FCIYHTYPDGT; SEQ ID NO: 39). See FIG. 2A. This epitope overlaps with the TIGIT/PVR binding interface as determined by X-ray crystal structure. Stengel et al. (2012) *Proc. Nat'l Acad. Sci.* (USA) 109:5399.

Analogous experiments with antibody 11G11 showed important contact points at residues G74, N70, H76, L65, L73, Q56, I68, H111 and P114. The epitope residues for 11G11 cluster into primary sequence regions comprising residues 56-76 (QVNWEQQDQLLAICNADLGWH; SEQ ID NO: 40) and residues 111-114 (HTYP; SEQ ID NO: 41), with other potential contacts in residues 120-139 (GRIFLEVLESSVAEHGARFQ; SEQ ID NO: 42). See FIG. 2B.

Analogous experiments with antibody 15A6 showed important contact points at residues H76, G74, L65, N58, I68, Q139, G135, L73, F107, N70, E60, H134, A132 and I109. The epitope residues for 15A6 cluster into primary sequence regions comprising residues 58-76 (NWEQQDQLLAICNADLGWH; SEQ ID NO: 38) and residues 107-109 (FCI), with other potential contacts in residues 132-139 (AEHGARFQ; SEQ ID NO: 43). See FIG. 2C.

All three epitopes include residues L65, I68, N70 and H76, suggesting that these residues and this region, i.e. residues 65-76 (LLAICNADLGWH; SEQ ID NO: 44), or 58-76 considering only 15A6 and 22G2, represents an important region ("core epitope") for binding of the anti-huTIGIT antibodies of the present invention.

Analogous experiments on the binding of huTIGIT to human PVR/CD155 showed important contact points at residues Q56, N58, I68, N70, L73, G74, W75, H76, H111, T112, Y113, P114, D115 and G116, which contacts fall predominantly in the epitope regions bound by antibodies 22G2, 11G11 and 15A6.

Example 5

Enhanced Lysis of $PVR^+$ Cells by NK Cells Treated with Anti-TIGIT Antibody The effect of anti-human TIGIT antibody 22G2 on NK-cell mediated lysis of $PVR^+$ cells in vitro was assessed. P815 cells (mouse mastocytoma cell line), both wild type and engineered to express human PVR, were exposed to human NK cells in the presence anti-huTIGIT mAb 22G2-IgG1, 22G2-IgG1.1, or an isotype control.

Briefly, human NK cells, effectors, were isolated from whole blood and incubated overnight with IL-2. NK cells were plated with target cells, either P815/PVR or P815 [wt], at an E:T cell ratio of 10:1 or 20:1. Antibodies were added to the wells at a final concentration of 5 μg/mL. Plates were incubated for 2-4 hours and cell supernatant was evaluated for release of lactate dehydrogenase (LDH), a product of dead or dying cells.

Results are presented at FIG. 3. Percent (%) specific lysis was calculated as [(test signal-mean spontaneous lysis)/(mean maximum lysis-mean spontaneous lysis)]×100. TIGIT blockade using anti-TIGIT antibody 22G2 reduces inhibitory signaling on NK cells, which results in increased lysis of PVR-expressing target cells in a DNAM-1 specific manner.

Example 6

Activation of $CD8^+$ T Cells by Anti-TIGIT Antibody

Experiments were performed to determine the effect of anti-human TIGIT antibody, alone and in combination with anti-human PD-1 antibody, on human T cells stimulated with antigenic peptides. As a preliminary matter, it was observed that $PD\text{-}1^+/TIGIT^+$ $CD8^+$ T cells were more prevalent in blood from healthy human donors exposed to a cocktail of antigenic peptides (from CMV, EBV, influenza and tetanus) than from unexposed blood. See FIG. 4A. IFNγ production was measured in blood treated with CEFT. See FIG. 4B. Although ineffective as monotherapy, anti-TIGIT mAb 22G2 enhanced anti-PD-1's ability to stimulate IFNγ production from human T cells exposed to the cocktail of antigenic peptides. See also Chauvin et al. (2015) *J. Clin. Invest.* 125:2046, in which the effect of anti-human TIGIT antibody 10D7 on human tumor specific $CD8^+$ T cells was determined in peripheral blood mononuclear cells (PBMC) from melanoma patients exposed to NY-ESO-1 peptide, with or without concurrent administration of anti-huPD-1 antibody.

Example 7

Anti-Tumor Activity of Anti-TIGIT Antibodies in Murine CT26 Tumor Model

Anti-mouse TIGIT antibodies were tested for anti-tumor activity, alone and in combination with anti-mouse PD-1 antibodies, in the syngeneic CT26 colon adenocarcinoma model. The anti-muTIGIT antibodies used in these experiments are mouse surrogates of the anti-huTIGIT antibodies of the present invention.

Briefly, an anti-muTIGIT mAb (clone 4B1) was prepared with either a murine IgG2a or a murine IgG1 D265A (having reduced effector function) Fc region, as well as an anti-muPD-1 (clone 4H2) with a murine IgG1 D265A Fc region. These antibodies, and combinations thereof, were administered to mice together with a mouse IgG1 isotype control to determine for anti-tumor activity in a syngeneic CT26 colon adenocarcinoma model. The IgG1 control antibody used for the studies is a recombinant human anti-diphtheria toxin antibody with a mouse IgG1 isotype.

Fifteen BALB/c mice per group (90 mice in total) were subcutaneously injected with $1 \times 10^6$ CT26 tumor cells on day 0. Treatment was begun at Day 7 after implantation. Tumors were measured, randomized into treatment groups so as to have comparable mean tumor volumes (45-50 mm³), and then treated intraperitoneally (IP) with the designated antibody (200 μg/dose) and again on Days 10 and 14. Each experiment included 200 μg/dose of control IgG1 antibody as well, and thus the control IgG1 experiment itself included 400 μg/dose. Tumor volumes were measured twice weekly.

Figure 5A:
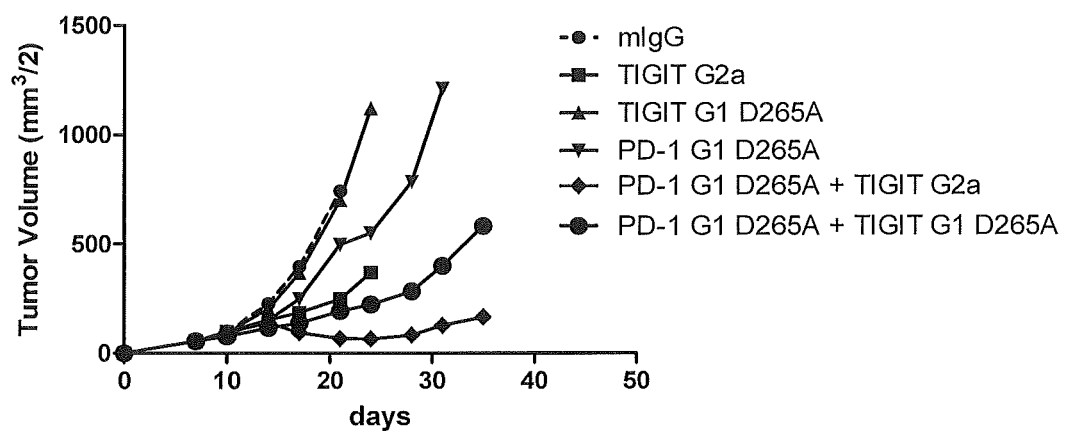
FIGS. 5A and 5B show the effects of anti-TIGIT antibodies, alone or in combination with other immunomodulatory therapy, on tumor growth in a mouse model.
Figure 5B:
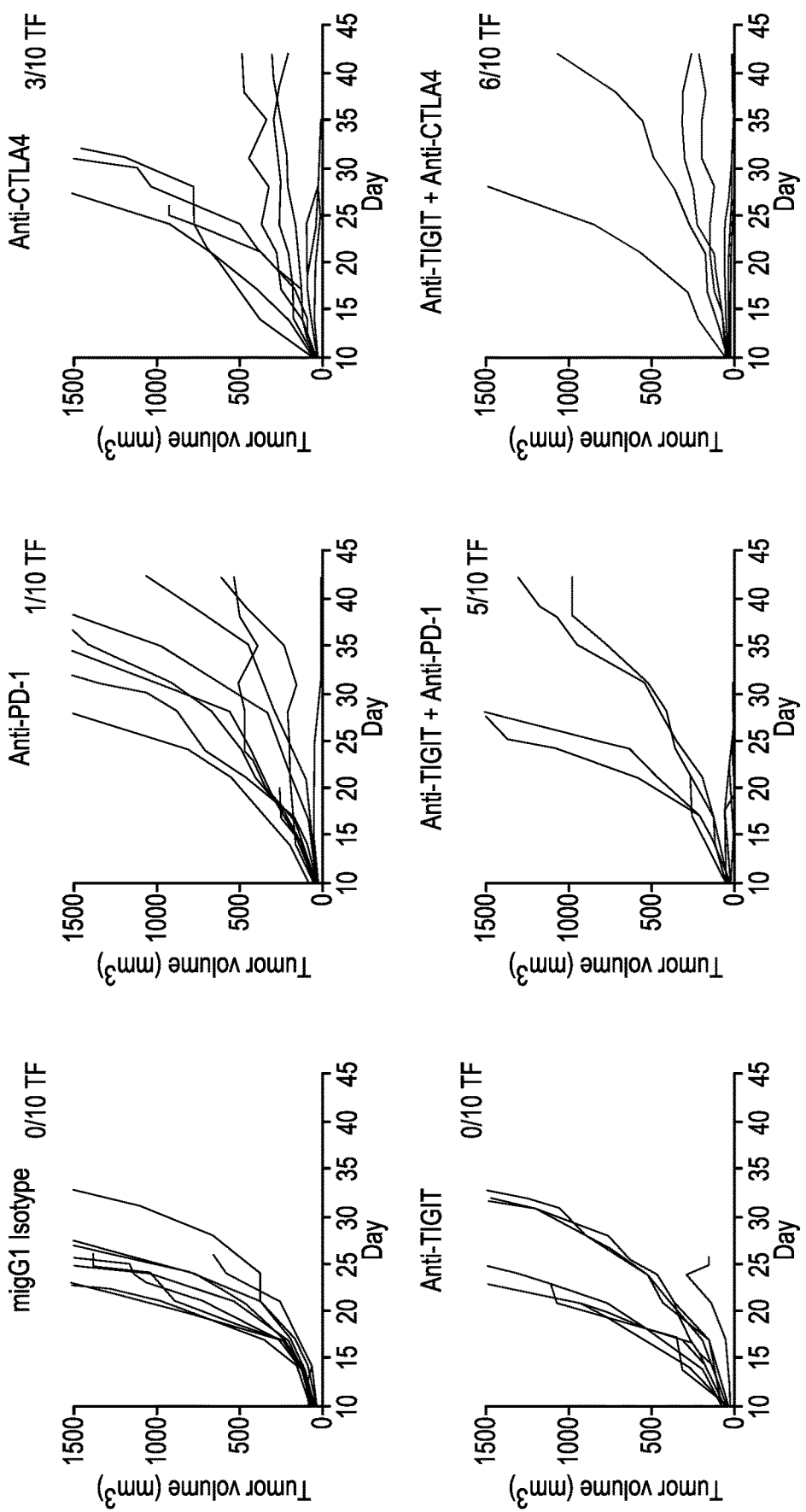

Results are presented in FIG. 5A, which presents the mean tumor volumes for each experiment as a function of time. The reduced effector function version of the anti-TIGIT antibody (G1 D265A) did not affect tumor growth and did not rid any mice of tumors, whereas the IgG2a reduced tumor growth and resulted in three of fifteen mice being tumor free at day 35. The combination of the IgG2a anti-TIGIT antibody with the anti-PD-1 antibody was highly effective at reducing tumor growth and led to ten of fifteen mice being tumor free, whereas the combination of anti-TIGIT G1 D265A with anti-PD-1 was somewhat less effective at reducing tumor growth and resulted in seven of fifteen mice being tumor free. Nevertheless, both the IgG2a and IgG1 D265A anti-TIGIT antibodies enhanced the activity of the anti-PD-1 antibody, which alone resulted in only two of fifteen mice being tumor free.

Similar experiments were performed to compare anti-TIGIT as monotherapy with anti-TIGIT/anti-PD-1 and anti-TIGIT/anti-CTLA-4 combination therapy. Both anti-TIGIT and anti-PD-1 antibodies were formatted as Fc-inert mouse IgG1-D265A isotype, and anti-CTLA-4 as a mouse IgG2b. Female BALB/c mice were implanted with $1 \times 10^6$ tumor cells on day 0, and antibodies were administered IP at 10 mg/kg on days 10, 14 and 17. Results are provided at FIG. 5B. Addition of anti-TIGIT to treatment with anti-PD-1 and anti-CTLA-4 significantly enhanced tumor growth inhibition (TGI), as is apparent from the combination therapy curves, with 56% TGI for anti-TIGIT/anti-PD-1 and 49% TGI for anti-TIGIT/anti-CTLA-4, compared with 7%, 18% and 13% TGI for monotherapy with anti-TIGIT, anti-PD-1 and anti-CTLA-4, respectively. Combination therapy also increased the number of tumor free mice at the end of the experiment from 1/10 to 5/10 for the combination with anti-PD-1, and from 3/10 to 6/10 for the combination with anti-CTLA-4.

Example 8

Other Properties of Anti-huTIGIT Antibodies 15A6, 22G2, 11G11 and 10D7

Various other in vitro assays were performed to determine the properties of selected antibodies of the present invention. Anti-huTIGIT mAbs 15A6, 22G2, 11G11 and 10D7 were found to bind to Jurkat cells expressing huTIGIT. Bioassay of Jurkat/hTIGIT cells demonstrated that antibodies 15A6, 11G11 and 10D7 are all block PVR signaling with roughly equivalent efficacy, and antibody 22G2 is about two-fold better (IC50=0.21 nM). Antibodies 15A6 and 22G2 were shown to bind to TIGIT from cynomolgus monkeys with substantially the same affinities as human TIGIT when expressed on CHO cells, whereas 11G11 and 10D7 did not. For example, antibody 22G2 IgG1.1f bound to human and monkey TIGIT with $K_D$ of 0.09 nM and 0.07 nM, respectively, and also had an EC50 for binding to CD8⁺ T cells of 0.55 nM and 0.28-0.58 nM, respectively, but did not bind to rat or mouse TIGIT. Subsequent experiments with primary cells, however, demonstrated that 15A6 did not bind well to cyno TIGIT in that context. Antibodies 22G2 and 15A6 stained human lymphocytes, but not 22 other human tissues up to a concentration of 10 μg/ml (cerebrum, cerebellum, heart, liver, lung, kidney, spleen, tonsil, thymus, colon, small intestine, stomach, pancreas, skin, skeletal muscle, adrenal, thyroid, peripheral nerve, prostate, placenta, testis, and uterus). Antibody 22G2 did not increase expression of 75 different cytokines and chemokines (including GM-CSF, IL-10, IL-12, IL-13, IL-2, IFNγ, IP-10) from human whole blood from eight donors when incubated at 10 μg/ml for 20 hours, suggesting low risk of cytokine release syndrome.

In separate experiments, anti-TIGIT mAb 22G2 IgG1.1f showed IC50s of 15.4 nM and 5.72 nM for blockade of TIGIT-mFc binding to P815 cells over-expressing human PVR and human Nectin-2, respectively, when each was present at its EC90 concentration (14.1 nM and 12.8 nM, respectively).

Antibody 22G2 IgG1.1f was found to have a single N-glycosylation site at N310 on the heavy chain, with a glycan profile typical for monoclonal antibodies produced in CHO.

These results suggest that antibody 22G2 has ideal properties for therapeutic use in the methods of the present invention, in that it binds to TIGIT when it is present on the surface of a cell, it inhibits PVR and Nectin-2 signaling, it does not bind to extraneous human tissues or induce unwanted cytokine or chemokine release, and it binds to cyno TIGIT, which is helpful in performing toxicology studies for use in studies in support of regulatory approval.

Example 9

Patient Selection Based on Expression of TIGIT, DNAM, PVR and Nectin-2

Expression levels of proteins associated with the TIGIT pathway (TIGIT, PVR/CD155, Nectin-2/CD112, DNAM/CD226) may be used to guide treatment with anti-TIGIT antibodies of the present invention. Soluble forms of PVR and Nectin-2 (sPVR and sNectin-2) may be detected in serum, e.g. by ELISA or other conventional means. TIGIT, PVR, Nectin-2, and DNAM may be detected on the surface of cells, such as tumor cells, CD8⁺ T cells, regulatory T cells, NK cells, or tumor infiltrating myeloid cells, e.g. by immunohistochemistry (IHC), flow cytometry (FACS), or mass spectrometric methods, including liquid chromatography mass spectrometry (LC-MS).

Without intending to be limited by theory, treatment with anti-TIGIT antibodies of the present invention will be based on blocking TIGIT binding to its ligands, e.g. PVR or Nectin-2, on an interacting cell and/or preventing interaction of TIGIT with DNAM on the same cell. Accordingly, tumors or tumor types most likely the respond to such treatment will be those in which TIGIT activity is important to tumor progression, such that blocking such TIGIT activity would enhance tumor erradication. Specifically, high levels of TIGIT+ TILs, such as TIGIT+ CD8+ T cells, TIGIT+ $T_{regs}$ or TIGIT+ NK cells, would suggest tumors likely to respond to antagonist anti-TIGIT treatment. DNAM expression on these TIGIT+ TILs would further suggest that the tumor may respond to anti-TIGIT treatment. Similarly, tumors that express high levels of the TIGIT ligands PVR and/or Nectin-2, either on tumor cells themselves or on tumor infiltrating myeloid cells, would also be good candidates for treatment with anti-TIGIT antibodies of the present invention.

Screening for expression levels of proteins of the TIGIT pathway may be performed at the level of a therapeutic indication selection or at the individual patient level ("patient stratification"). For example, expression levels may be determined in tissue samples from many patients having each of a number of different cancers, so as to determine which types of cancer show protein expression patterns suggesting that the particular type of cancer would be amenable to treatment with the antagonist anti-TIGIT mAbs of the present invention. Once such determination is made for a statistically adequate number of samples, anti-TIGIT therapy could be recommended for any individual patient suffering from the type of cancer expected to be responsive to anti-TIGIT therapy. Alternatively, samples from individual patients may be tested instead, to help guide treatment decisions specifically for that patient.

Because the relevant cells to be tested for expression of TIGIT pathway proteins are those in the tumor and surrounding microenviroment, such screening is likely to require obtain a sample of the tumor, e.g. by biopsy or resection.

Accordingly, the present invention also provides methods for identifying tumor types or specific tumors that are good candidates for treatment with the antagonist anti-TIGIT antibodies of the present invention by measuring levels of TIGIT in infiltrating CD8+ T cells, $T_{regs}$ or NK cells, and/or by measuring the expression of PVR and/or Nectin-2 in tumor cells or tumor infiltrating myeloid cells.

In one example, anti-TIGIT therapy is employed in place of, in conjunction with, or supplementary to, treatment with a PD-1 or PD-L1 inhibitor. Tumors exhibiting high PVR/Nectin-2 expression and low PD-L1 expression may be treated with anti-TIGIT antibody as monotherapy, or an anti-TIGIT antibody in combination with another immuno-oncology agent other than a PD-1/PD-L1 antagonist if there is a biological rationale for such agent. Anti-TIGIT antibodies of the present invention may be administered substantially concurrently with anti-PD-1/PD-L1 antibodies in tumors exhibiting high PVR/Nectin-2 expression and also high PD-L1 expression. Alternatively, anti-TIGIT antibodies of the present invention may be administered after anti-PD-1/PD-L1 therapy in refractory patients, relapsing patients, or those with any other incomplete or unsatisfactory response, if their tumors show elevated expression of PVR and/or Nectin-2.

In experiments to identify tumor types likely to be amenable to treatment with the antagonist anti-TIGIT antibodies of the present invention, expression of human PVR mRNA was determined for various human cancers using TCGA datasets. Results are presented at FIG. 6A. Results are presented in descending order, with tumors with highest levels of PVR mRNA, and thus most likely to amenable to treatment with anti-TIGIT antibodies of the present invention, at the top.

Figure 6B:
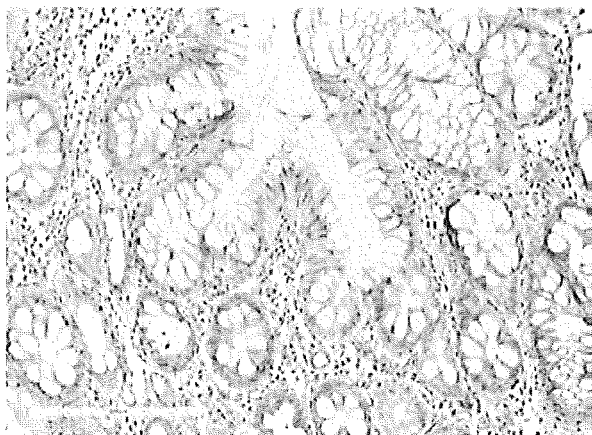
Figure 6B:

PVR was also detected at a much higher level in a colon adenocarcinoma sample than in a colon epithelium control sample by IHC. See FIG. 6B. Further IHC experiments revealed elevated PVR expression in 100% of hepatocellular cancer samples (10/10), 90% colorectal cancer samples (9/10), and 44% ovarian cancer samples (4/9). These results suggest that patients with these cancers, particularly hepatocellular and colorectal cancers, would be good candidates for treatment with the antagonist anti-TIGIT antibodies of the present invention.

The present invention also provides methods of treatment, e.g. treatment of colorectal cancer, comprising determining the presence of absence of intratumoral bacteria *Fusobacterium nucleatum*, the presence of which suggests that the tumor may be a good candidate for treatment of the anti-TIGIT antibody of the present invention. Such methods of treatment also optionally include administering an antibiotic to a subject having intratumoral bacteria *Fusobacterium nucleatum*, e.g. metronidazole, piperacillin/tazobactum, ticarcillin/clavulanate, amoxicillin/sulbactum, ampicillin/sulbactum, ertupenem, imipenem, meropenem, clindamycin, or cefoxitin.

TABLE 5

SUMMARY OF SEQUENCE LISTING

| SEQ ID NO. | Description |
| --- | --- |
| 1 | Human TIGIT polypeptide (NP_776160.2) |
| 2 | 15A6 VH domain |
| 3 | 15A6 VH domain A72S |
| 4 | 15A6 VH domain N112T |
| 5 | 15A6 VH domain A72S N112T |
| 6 | 15A6 VL domain |
| 7 | 22G2 VH domain |
| 8 | 22G2 VH domain H3Q |
| 9 | 22G2 VL domain |
| 10 | 11G11 VH domain |
| 11 | 11G11 VL domain) |
| 12 | 10D7 VH domain |
| 13 | 10D7 VL domain |
| 14 | 15A6 CDRH1 |
| 15 | 15A6 CDRH2 |
| 16 | 15A6 CDRH3 |
| 17 | 15A6 CDRL1 |
| 18 | 15A6 CDRL2 |
| 19 | 15A6 CDRL3 |
| 20 | 22G2 CDRH1 |
| 21 | 22G2 CDRH2 |
| 22 | 22G2 CDRH3 |
| 23 | 22G2 CDRL1 |
| 24 | 22G2 CDRL2 |
| 25 | 22G2 CDRL3 |
| 26 | 11G11 CDRH1 |
| 27 | 11G11 CDRH2 |
| 28 | 11G11 CDRH3 |
| 29 | 11G11 CDRL1 |
| 30 | 11G11 CDRL2 |
| 31 | 11G11 CDRL3 |
| 32 | 10D7 CDRH1 |
| 33 | 10D7 CDRH2 |
| 34 | 10D7 CDRH3 |
| 35 | 10D7 CDRL1 |
| 36 | 10D7 CDRL2 |
| 37 | 10D7 CDRL3 |
| 38 | 22G2/15A6 epitope - huTIGIT residues 58-76 |
| 39 | 22G2 epitope - huTIGIT residues 107-117 |
| 40 | 11G11 epitope - huTIGIT residues 56-76 |
| 41 | 11G11 epitope - huTIGIT residues 111-114 |
| 42 | 11G11 epitope - huTIGIT residues 120-139 |
| 43 | 15A6 epitope - huTIGIT residues 132-139 |
| 44 | 22G2/11G11/15A6 core epitope - huTIGIT residues 65-76 |
| 45 | IgG1f constant domain (human) |
| 46 | IgG1 constant domain, allotypic variant (human) |
| 47 | IgG1.3 constant domain (human) |

TABLE 5-continued

SUMMARY OF SEQUENCE LISTING

| SEQ ID NO. | Description |
|---|---|
| 48 | IgG1.1f constant domain (human) |
| 49 | Kappa constant domain (human) |
| 50 | PVR/CD155 precursor alpha (human) NP_006496.4 |
| 51 | PVR/CD155 precursor beta (human) NP_001129240.1 |
| 52 | PVR/CD155 precursor gamma (human) NP_001129241.1 |
| 53 | PVR/CD155 precursor delta (human) NP_001129242.2 |

With regard to antibody sequences, the Sequence Listing provides the sequences of the mature variable regions of the heavy and light chains, i.e. the sequences do not include signal peptides.

EQUIVALENTS

Those skilled in the art will recognize, or be able to ascertain using no more than routine experimentation, many equivalents of the specific embodiments disclosed herein. Such equivalents are intended to be encompassed by the following claims.

We claim:

1. A method of enhancing an antigen-specific T cell response in a subject in need thereof comprising contacting the T cell with an isolated antibody, or antigen binding fragment thereof, that binds to human TIGIT (T cell immunoreceptor with Ig and ITIM domains) comprising:
   a) a heavy chain comprising a heavy chain variable domain comprising:
      i) CDRH1 comprising the sequence of SEQ ID NO.: 20;
      ii) CDRH2 comprising the sequence of SEQ ID NO.: 21; and
      iii) CDRH3 comprising the sequence of SEQ ID NO.: 22; and
   b) a light chain comprising a light chain variable domain comprising:
      i) CDRL1 comprising the sequence of SEQ ID NO.: 23;
      ii) CDRL2 comprising the sequence of SEQ ID NO.: 24; and
      iii) CDRL3 comprising the sequence of SEQ ID NO.: 25,
such that an antigen-specific T cell response is enhanced.

2. The method of claim 1 wherein the subject has a tumor or a chronic viral infection and an immune response against the tumor or viral infection is enhanced.

3. A method of reducing or depleting regulatory T cells in a tumor of a subject in need thereof comprising administering an effective amount of an antibody, or antigen binding fragment thereof, that binds to human TIGIT (T cell immunoreceptor with Ig and ITIM domains) comprising:
   a) a heavy chain comprising a heavy chain variable domain comprising:
      i) CDRH1 comprising the sequence of SEQ ID NO.: 20;
      ii) CDRH2 comprising the sequence of SEQ ID NO.: 21; and
      iii) CDRH3 comprising the sequence of SEQ ID NO.: 22; and
   b) a light chain comprising a light chain variable domain comprising:
      i) CDRL1 comprising the sequence of SEQ ID NO.: 23;
      ii) CDRL2 comprising the sequence of SEQ ID NO.: 24; and
      iii) CDRL3 comprising the sequence of SEQ ID NO.: 25,
such that the number of regulatory T cells in a tumor is reduced.

4. A method of treating cancer comprising administering to a subject in need thereof a therapeutically effective amount of an antibody, or antigen binding fragment thereof, that binds to human TIGIT (T cell immunoreceptor with Ig and ITIM domains) comprising:
- a) a heavy chain comprising a heavy chain variable domain comprising:
  - i) CDRH1 comprising the sequence of SEQ ID NO.: 20;
  - ii) CDRH2 comprising the sequence of SEQ ID NO.: 21; and
  - iii) CDRH3 comprising the sequence of SEQ ID NO.: 22; and
- b) a light chain comprising a light chain variable domain comprising:
  - i) CDRL1 comprising the sequence of SEQ ID NO.: 23;
  - ii) CDRL2 comprising the sequence of SEQ ID NO.: 24; and
  - iii) CDRL3 comprising the sequence of SEQ ID NO.: 25.

5. The method of claim 4 further comprising administering one or more additional therapeutic agents selected from the group consisting of an anti-PD-1 antibody, an anti-LAG-3 antibody, an anti-CTLA-4 antibody, or an anti-PD-L1 antibody.

6. The method of treating cancer of claim 4 wherein the subject has a tumor comprising one or more of the following:
- a) high levels of infiltrating TIGIT+ T cells and/or NK cells;
- b) elevated expression of PVR and/or Nectin-2 on tumor cells or tumor infiltrating myeloid cells; and
- c) a *Fusobacterium nucleatum* infection.

* * * * *

SEQUENCE LISTING

<160> NUMBER OF SEQ ID NOS: 53

<210> SEQ ID NO 1
<211> LENGTH: 244
<212> TYPE: PRT
<213> ORGANISM: Homo sapiens

<400> SEQUENCE: 1

```
Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
        195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly
```

<210> SEQ ID NO 2
<211> LENGTH: 118
<212> TYPE: PRT
<213> ORGANISM: Homo sapiens

<400> SEQUENCE: 2

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Arg Tyr Phe Trp Gly Trp Ile Arg Gln Pro Pro Gly Lys Gly Leu Glu
        35                  40                  45

Trp Ile Gly Tyr Ile Tyr Tyr Arg Gly Ser Thr Tyr Tyr Asn Pro Ser
    50                  55                  60

Leu Lys Ser Arg Val Thr Ile Ala Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ser Ser Ser Ala Trp Tyr Phe Asp Tyr Trp Gly Gln Gly Asn
            100                 105                 110

Leu Val Thr Val Ser Ser
        115

<210> SEQ ID NO 3
<211> LENGTH: 118
<212> TYPE: PRT
<213> ORGANISM: Artificial Sequence
<220> FEATURE:
<223> OTHER INFORMATION: human sequence with A72S modification

<400> SEQUENCE: 3

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Arg Tyr Phe Trp Gly Trp Ile Arg Gln Pro Pro Gly Lys Gly Leu Glu
        35                  40                  45

Trp Ile Gly Tyr Ile Tyr Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ser Ser Ser Ala Trp Tyr Phe Asp Tyr Trp Gly Gln Gly Asn
            100                 105                 110

Leu Val Thr Val Ser Ser
        115

<210> SEQ ID NO 4
<211> LENGTH: 118
<212> TYPE: PRT
<213> ORGANISM: Artificial Sequence
<220> FEATURE:
<223> OTHER INFORMATION: human sequence with N112Q modification

<400> SEQUENCE: 4

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Arg Tyr Phe Trp Gly Trp Ile Arg Gln Pro Pro Gly Lys Gly Leu Glu
        35                  40                  45

```
Trp Ile Gly Tyr Ile Tyr Tyr Arg Gly Ser Thr Tyr Tyr Asn Pro Ser
        50                  55                  60

Leu Lys Ser Arg Val Thr Ile Ala Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ser Ser Ser Ala Trp Tyr Phe Asp Tyr Trp Gly Gln Gly Thr
                100                 105                 110

Leu Val Thr Val Ser Ser
        115

<210> SEQ ID NO 5
<211> LENGTH: 118
<212> TYPE: PRT
<213> ORGANISM: Artificial Sequence
<220> FEATURE:
<223> OTHER INFORMATION: human sequence with A72S and N112T
      modifications

<400> SEQUENCE: 5

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Arg Tyr Phe Trp Gly Trp Ile Arg Gln Pro Pro Gly Lys Gly Leu Glu
                35                  40                  45

Trp Ile Gly Tyr Ile Tyr Tyr Arg Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ser Ser Ser Ala Trp Tyr Phe Asp Tyr Trp Gly Gln Gly Thr
                100                 105                 110

Leu Val Thr Val Ser Ser
        115

<210> SEQ ID NO 6
<211> LENGTH: 107
<212> TYPE: PRT
<213> ORGANISM: Homo sapiens

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Tyr
                85                  90                  95

Thr Phe Gly Gln Gly Thr Lys Leu Glu Ile Lys
                100                 105
```

<210> SEQ ID NO 7
<211> LENGTH: 130
<212> TYPE: PRT
<213> ORGANISM: Homo sapiens

<400> SEQUENCE: 7

```
Gln Val His Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ile Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Tyr Tyr Val Ser Gly Asn Tyr Tyr Asn Val Asp Tyr
            100                 105                 110

Tyr Phe Phe Gly Val Asp Val Trp Gly Gln Gly Thr Thr Val Thr Val
            115                 120                 125

Ser Ser
    130
```

<210> SEQ ID NO 8
<211> LENGTH: 130
<212> TYPE: PRT
<213> ORGANISM: Artificial Sequence
<220> FEATURE:
<223> OTHER INFORMATION: human sequence with H3Q modification

<400> SEQUENCE: 8

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ile Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Tyr Tyr Val Ser Gly Asn Tyr Tyr Asn Val Asp Tyr
            100                 105                 110

Tyr Phe Phe Gly Val Asp Val Trp Gly Gln Gly Thr Thr Val Thr Val
            115                 120                 125

Ser Ser
    130
```

<210> SEQ ID NO 9
<211> LENGTH: 109
<212> TYPE: PRT
<213> ORGANISM: Homo sapiens

<400> SEQUENCE: 9

-continued

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Phe Thr Phe Gly Pro Gly Thr Lys Val Asp Ile Lys
            100                 105

<210> SEQ ID NO 10
<211> LENGTH: 126
<212> TYPE: PRT
<213> ORGANISM: Homo sapiens

<400> SEQUENCE: 10

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser His Tyr Trp Gly Trp Ile Arg Gln Pro Pro Gly Lys Gly Leu Glu
        35                  40                  45

Trp Ile Gly Asn Ile Phe Tyr Ser Gly His Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Gly Leu Leu Trp Phe Gly Gly Leu Ser Pro Tyr Tyr
            100                 105                 110

Phe Asp Tyr Trp Gly Gln Gly Thr Leu Val Thr Val Ser Ser
        115                 120                 125

<210> SEQ ID NO 11
<211> LENGTH: 106
<212> TYPE: PRT
<213> ORGANISM: Homo sapiens

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Leu Glu Ile Lys
            100                 105

<210> SEQ ID NO 12
<211> LENGTH: 128
<212> TYPE: PRT
<213> ORGANISM: Homo sapiens

<400> SEQUENCE: 12

Gln Gly Gln Leu Val Gln Ser Gly Ala Glu Val Lys Lys Pro Gly Ser
1               5                   10                  15

Ser Val Lys Val Ser Cys Lys Ala Ser Gly Gly Ile Phe Arg Asn Tyr
            20                  25                  30

Ala Ile Ser Trp Val Arg Gln Ala Pro Gly Gln Gly Leu Glu Trp Met
        35                  40                  45

Gly Gly Ile Ile Pro Phe Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ala Ala Gly Thr Thr Arg Tyr Gly Tyr Tyr Tyr
            100                 105                 110

Tyr Gly Met Asp Val Trp Gly Gln Gly Thr Thr Val Thr Val Ser Ser
            115                 120                 125

<210> SEQ ID NO 13
<211> LENGTH: 107
<212> TYPE: PRT
<213> ORGANISM: Homo sapiens

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105

<210> SEQ ID NO 14
<211> LENGTH: 7
<212> TYPE: PRT
<213> ORGANISM: Homo sapiens

<400> SEQUENCE: 14

Ser Ser Arg Tyr Phe Trp Gly
1               5

<210> SEQ ID NO 15
<211> LENGTH: 16

```
<212> TYPE: PRT
<213> ORGANISM: Homo sapiens

<400> SEQUENCE: 15

Tyr Ile Tyr Tyr Arg Gly Ser Thr Tyr Asn Pro Ser Leu Lys Ser
1               5                   10                  15

<210> SEQ ID NO 16
<211> LENGTH: 8
<212> TYPE: PRT
<213> ORGANISM: Homo sapiens

<400> SEQUENCE: 16

Ser Ser Ala Trp Tyr Phe Asp Tyr
1               5

<210> SEQ ID NO 17
<211> LENGTH: 12
<212> TYPE: PRT
<213> ORGANISM: Homo sapiens

<400> SEQUENCE: 17

Arg Ala Ser Gln Ser Val Ser Ser Ser Tyr Leu Ala
1               5                   10

<210> SEQ ID NO 18
<211> LENGTH: 7
<212> TYPE: PRT
<213> ORGANISM: Homo sapiens

<400> SEQUENCE: 18

Gly Ala Ser Ser Arg Ala Thr
1               5

<210> SEQ ID NO 19
<211> LENGTH: 8
<212> TYPE: PRT
<213> ORGANISM: Homo sapiens

<400> SEQUENCE: 19

Gln Gln Tyr Gly Ser Leu Tyr Thr
1               5

<210> SEQ ID NO 20
<211> LENGTH: 7
<212> TYPE: PRT
<213> ORGANISM: Homo sapiens

<400> SEQUENCE: 20

Ser Gly Ile Tyr Tyr Trp Ser
1               5

<210> SEQ ID NO 21
<211> LENGTH: 16
<212> TYPE: PRT
<213> ORGANISM: Homo sapiens

<400> SEQUENCE: 21

Tyr Ile Tyr Tyr Ser Gly Ser Thr Asn Tyr Asn Pro Ser Leu Lys Ser
1               5                   10                  15

<210> SEQ ID NO 22
<211> LENGTH: 20
<212> TYPE: PRT
<213> ORGANISM: Homo sapiens
```

<400> SEQUENCE: 22

Asp Tyr Tyr Val Ser Gly Asn Tyr Tyr Asn Val Asp Tyr Tyr Phe Phe
1               5                   10                  15

Gly Val Asp Val
            20

<210> SEQ ID NO 23
<211> LENGTH: 11
<212> TYPE: PRT
<213> ORGANISM: Homo sapiens

<400> SEQUENCE: 23

Arg Ala Ser Gln Ser Val Ser Ser Tyr Leu Ala
1               5                   10

<210> SEQ ID NO 24
<211> LENGTH: 7
<212> TYPE: PRT
<213> ORGANISM: Homo sapiens

<400> SEQUENCE: 24

Asp Ala Ser Asn Arg Ala Thr
1               5

<210> SEQ ID NO 25
<211> LENGTH: 11
<212> TYPE: PRT
<213> ORGANISM: Homo sapiens

<400> SEQUENCE: 25

Gln Gln Arg Ser Asn Trp Pro Pro Leu Phe Thr
1               5                   10

<210> SEQ ID NO 26
<211> LENGTH: 7
<212> TYPE: PRT
<213> ORGANISM: Homo sapiens

<400> SEQUENCE: 26

Ser Ser Ser His Tyr Trp Gly
1               5

<210> SEQ ID NO 27
<211> LENGTH: 16
<212> TYPE: PRT
<213> ORGANISM: Homo sapiens

<400> SEQUENCE: 27

Asn Ile Phe Tyr Ser Gly His Thr Tyr Tyr Asn Pro Ser Leu Lys Ser
1               5                   10                  15

<210> SEQ ID NO 28
<211> LENGTH: 16
<212> TYPE: PRT
<213> ORGANISM: Homo sapiens

<400> SEQUENCE: 28

Gln Gly Leu Leu Trp Phe Gly Gly Leu Ser Pro Tyr Tyr Phe Asp Tyr
1               5                   10                  15

<210> SEQ ID NO 29
<211> LENGTH: 11
<212> TYPE: PRT

```
<213> ORGANISM: Homo sapiens

<400> SEQUENCE: 29

Arg Ala Ser Gln Ser Val Ser Ser Tyr Leu Ala
1               5                   10

<210> SEQ ID NO 30
<211> LENGTH: 7
<212> TYPE: PRT
<213> ORGANISM: Homo sapiens

<400> SEQUENCE: 30

Asp Ala Ser Asn Arg Ala Thr
1               5

<210> SEQ ID NO 31
<211> LENGTH: 8
<212> TYPE: PRT
<213> ORGANISM: Homo sapiens

<400> SEQUENCE: 31

Gln Gln Arg Ser Asn Trp Pro Thr
1               5

<210> SEQ ID NO 32
<211> LENGTH: 5
<212> TYPE: PRT
<213> ORGANISM: Homo sapiens

<400> SEQUENCE: 32

Asn Tyr Ala Ile Ser
1               5

<210> SEQ ID NO 33
<211> LENGTH: 17
<212> TYPE: PRT
<213> ORGANISM: Homo sapiens

<400> SEQUENCE: 33

Gly Ile Ile Pro Phe Phe Gly Thr Ala Asn Tyr Ala Gln Lys Phe Gln
1               5                   10                  15

Gly

<210> SEQ ID NO 34
<211> LENGTH: 19
<212> TYPE: PRT
<213> ORGANISM: Homo sapiens

<400> SEQUENCE: 34

Gly Gly Ala Ala Ala Gly Thr Thr Arg Tyr Gly Tyr Tyr Tyr Tyr Gly
1               5                   10                  15

Met Asp Val

<210> SEQ ID NO 35
<211> LENGTH: 11
<212> TYPE: PRT
<213> ORGANISM: Homo sapiens

<400> SEQUENCE: 35

Arg Ala Ser Gln Gly Ile Ser Ser Trp Leu Ala
1               5                   10

<210> SEQ ID NO 36
```

```
<211> LENGTH: 7
<212> TYPE: PRT
<213> ORGANISM: Homo sapiens

<400> SEQUENCE: 36

Ala Ala Ser Ser Leu Gln Ser
1               5

<210> SEQ ID NO 37
<211> LENGTH: 9
<212> TYPE: PRT
<213> ORGANISM: Homo sapiens

<400> SEQUENCE: 37

Gln Gln Tyr Asn Ser Tyr Pro Ile Thr
1               5

<210> SEQ ID NO 38
<211> LENGTH: 19
<212> TYPE: PRT
<213> ORGANISM: Homo sapiens

<400> SEQUENCE: 38

Asn Trp Glu Gln Gln Asp Gln Leu Leu Ala Ile Cys Asn Ala Asp Leu
1               5                   10                  15

Gly Trp His

<210> SEQ ID NO 39
<211> LENGTH: 11
<212> TYPE: PRT
<213> ORGANISM: Homo sapiens

<400> SEQUENCE: 39

Phe Cys Ile Tyr His Thr Tyr Pro Asp Gly Thr
1               5                   10

<210> SEQ ID NO 40
<211> LENGTH: 21
<212> TYPE: PRT
<213> ORGANISM: Homo sapiens

<400> SEQUENCE: 40

Gln Val Asn Trp Glu Gln Gln Asp Gln Leu Leu Ala Ile Cys Asn Ala
1               5                   10                  15

Asp Leu Gly Trp His
            20

<210> SEQ ID NO 41
<211> LENGTH: 4
<212> TYPE: PRT
<213> ORGANISM: Homo sapiens

<400> SEQUENCE: 41

His Thr Tyr Pro
1

<210> SEQ ID NO 42
<211> LENGTH: 20
<212> TYPE: PRT
<213> ORGANISM: Homo sapiens

<400> SEQUENCE: 42

Gly Arg Ile Phe Leu Glu Val Leu Glu Ser Ser Val Ala Glu His Gly
1               5                   10                  15
```

Ala Arg Phe Gln
        20

<210> SEQ ID NO 43
<211> LENGTH: 8
<212> TYPE: PRT
<213> ORGANISM: Homo sapiens

<400> SEQUENCE: 43

Ala Glu His Gly Ala Arg Phe Gln
1               5

<210> SEQ ID NO 44
<211> LENGTH: 12
<212> TYPE: PRT
<213> ORGANISM: Homo sapiens

<400> SEQUENCE: 44

Leu Leu Ala Ile Cys Asn Ala Asp Leu Gly Trp His
1               5                   10

<210> SEQ ID NO 45
<211> LENGTH: 329
<212> TYPE: PRT
<213> ORGANISM: Homo sapiens

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

```
Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 46
<211> LENGTH: 329
<212> TYPE: PRT
<213> ORGANISM: Homo sapiens

<400> SEQUENCE: 46

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 47
<211> LENGTH: 329
<212> TYPE: PRT
<213> ORGANISM: Homo sapiens

<400> SEQUENCE: 47

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly

<210> SEQ ID NO 48
<211> LENGTH: 329
<212> TYPE: PRT
<213> ORGANISM: Homo sapiens

<400> SEQUENCE: 48

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 49
<211> LENGTH: 107
<212> TYPE: PRT
<213> ORGANISM: Homo sapiens -continued

```
<400> SEQUENCE: 49

Arg Thr Val Ala Ala Pro Ser Val Phe Ile Phe Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 50
<211> LENGTH: 417
<212> TYPE: PRT
<213> ORGANISM: Homo sapiens
<220> FEATURE:
<221> NAME/KEY: SIGNAL
<222> LOCATION: (1)..(20)

<400> SEQUENCE: 50

Met Ala Arg Ala Met Ala Ala Trp Pro Leu Leu Leu Val Ala Leu
1               5                   10                  15

Leu Val Leu Ser Trp Pro Pro Gly Thr Gly Asp Val Val Gln
            20                  25                  30

Ala Pro Thr Gln Val Pro Gly Phe Leu Gly Asp Ser Val Thr Leu Pro
        35                  40                  45

Cys Tyr Leu Gln Val Pro Asn Met Glu Val Thr His Val Ser Gln Leu
    50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
            100                 105                 110

Leu Arg Val Glu Asp Glu Gly Asn Tyr Thr Cys Leu Phe Val Thr Phe
        115                 120                 125

Pro Gln Gly Ser Arg Ser Val Asp Ile Trp Leu Arg Val Leu Ala Lys
    130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
                165                 170                 175

Ile Thr Trp His Ser Asp Leu Gly Gly Met Pro Asn Thr Ser Gln Val
            180                 185                 190

Pro Gly Phe Leu Ser Gly Thr Val Thr Val Thr Ser Leu Trp Ile Leu
        195                 200                 205

Val Pro Ser Ser Gln Val Asp Gly Lys Asn Val Thr Cys Lys Val Glu
    210                 215                 220

His Glu Ser Phe Glu Lys Pro Gln Leu Leu Thr Val Asn Leu Thr Val
225                 230                 235                 240
```

```
Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
            260                 265                 270

Glu Pro Thr Gly Tyr Asn Trp Ser Thr Thr Met Gly Pro Leu Pro Pro
        275                 280                 285

Phe Ala Val Ala Gln Gly Ala Gln Leu Leu Ile Arg Pro Val Asp Lys
290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
                325                 330                 335

His Ser Gly Met Ser Arg Asn Ala Ile Ile Phe Leu Val Leu Gly Ile
            340                 345                 350

Leu Val Phe Leu Ile Leu Leu Gly Ile Gly Ile Tyr Phe Tyr Trp Ser
        355                 360                 365

Lys Cys Ser Arg Glu Val Leu Trp His Cys His Leu Cys Pro Ser Ser
370                 375                 380

Thr Glu His Ala Ser Ala Ser Ala Asn Gly His Val Ser Tyr Ser Ala
385                 390                 395                 400

Val Ser Arg Glu Asn Ser Ser Gln Asp Pro Gln Thr Glu Gly Thr
                405                 410                 415
Arg

<210> SEQ ID NO 51
<211> LENGTH: 372
<212> TYPE: PRT
<213> ORGANISM: Homo sapiens
<220> FEATURE:
<221> NAME/KEY: SIGNAL
<222> LOCATION: (1)..(27)

<400> SEQUENCE: 51

Met Ala Arg Ala Met Ala Ala Ala Trp Pro Leu Leu Leu Val Ala Leu
1               5                   10                  15

Leu Val Leu Ser Trp Pro Pro Gly Thr Gly Asp Val Val Gln
                20                  25                  30

Ala Pro Thr Gln Val Pro Gly Phe Leu Gly Asp Ser Val Thr Leu Pro
            35                  40                  45

Cys Tyr Leu Gln Val Pro Asn Met Glu Val Thr His Val Ser Gln Leu
        50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
            100                 105                 110

Leu Arg Val Glu Asp Glu Gly Asn Tyr Thr Cys Leu Phe Val Thr Phe
        115                 120                 125

Pro Gln Gly Ser Arg Ser Val Asp Ile Trp Leu Arg Val Leu Ala Lys
130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
                165                 170                 175
```

```
Ile Thr Trp His Ser Asp Leu Gly Gly Met Pro Asn Thr Ser Gln Val
            180                 185                 190

Pro Gly Phe Leu Ser Gly Thr Val Thr Val Thr Ser Leu Trp Ile Leu
        195                 200                 205

Val Pro Ser Ser Gln Val Asp Gly Lys Asn Val Thr Cys Lys Val Glu
    210                 215                 220

His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
            260                 265                 270

Glu Pro Thr Gly Tyr Asn Trp Ser Thr Thr Met Gly Pro Leu Pro Pro
        275                 280                 285

Phe Ala Val Ala Gln Gly Ala Gln Leu Leu Ile Arg Pro Val Asp Lys
    290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
                325                 330                 335

His Ser Gly Thr Glu His Ala Ser Ala Ser Ala Asn Gly His Val Ser
            340                 345                 350

Tyr Ser Ala Val Ser Arg Glu Asn Ser Ser Ser Gln Asp Pro Gln Thr
        355                 360                 365

Glu Gly Thr Arg
    370

<210> SEQ ID NO 52
<211> LENGTH: 364
<212> TYPE: PRT
<213> ORGANISM: Homo sapiens
<220> FEATURE:
<221> NAME/KEY: SIGNAL
<222> LOCATION: (1)..(27)

<400> SEQUENCE: 52

Met Ala Arg Ala Met Ala Ala Ala Trp Pro Leu Leu Leu Val Ala Leu
1               5                   10                  15

Leu Val Leu Ser Trp Pro Pro Gly Thr Gly Asp Val Val Gln
            20                  25                  30

Ala Pro Thr Gln Val Pro Gly Phe Leu Gly Asp Ser Val Thr Leu Pro
        35                  40                  45

Cys Tyr Leu Gln Val Pro Asn Met Glu Val Thr His Val Ser Gln Leu
    50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
            100                 105                 110

Leu Arg Val Glu Asp Glu Gly Asn Tyr Thr Cys Leu Phe Val Thr Phe
        115                 120                 125

Pro Gln Gly Ser Arg Ser Val Asp Ile Trp Leu Arg Val Leu Ala Lys
    130                 135                 140

Pro Gln Asn Thr Ala Glu Val Gln Lys Val Gln Leu Thr Gly Glu Pro
145                 150                 155                 160
```

-continued

```
Val Pro Met Ala Arg Cys Val Ser Thr Gly Gly Arg Pro Pro Ala Gln
                165                 170                 175

Ile Thr Trp His Ser Asp Leu Gly Gly Met Pro Asn Thr Ser Gln Val
            180                 185                 190

Pro Gly Phe Leu Ser Gly Thr Val Thr Val Thr Ser Leu Trp Ile Leu
        195                 200                 205

Val Pro Ser Ser Gln Val Asp Gly Lys Asn Val Thr Cys Lys Val Glu
    210                 215                 220

His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
            260                 265                 270

Glu Pro Thr Gly Tyr Asn Trp Ser Thr Thr Met Gly Pro Leu Pro Pro
        275                 280                 285

Phe Ala Val Ala Gln Gly Ala Gln Leu Leu Ile Arg Pro Val Asp Lys
    290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Gly Thr Glu His Ala Ser
                325                 330                 335

Ala Ser Ala Asn Gly His Val Ser Tyr Ser Ala Val Ser Arg Glu Asn
            340                 345                 350

Ser Ser Ser Gln Asp Pro Gln Thr Glu Gly Thr Arg
        355                 360

<210> SEQ ID NO 53
<211> LENGTH: 392
<212> TYPE: PRT
<213> ORGANISM: Homo sapiens
<220> FEATURE:
<221> NAME/KEY: SIGNAL
<222> LOCATION: (1)..(27)

<400> SEQUENCE: 53

Met Ala Arg Ala Met Ala Ala Trp Pro Leu Leu Leu Val Ala Leu
1               5                   10                  15

Leu Val Leu Ser Trp Pro Pro Gly Thr Gly Asp Val Val Gln
            20                  25                  30

Ala Pro Thr Gln Val Pro Gly Phe Leu Gly Asp Ser Val Thr Leu Pro
        35                  40                  45

Cys Tyr Leu Gln Val Pro Asn Met Glu Val Thr His Val Ser Gln Leu
    50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
            100                 105                 110

Leu Arg Val Glu Asp Glu Gly Asn Tyr Thr Cys Leu Phe Val Thr Phe
        115                 120                 125

Pro Gln Gly Ser Arg Ser Val Asp Ile Trp Leu Arg Val Leu Ala Lys
    130                 135                 140

Pro Gln Asn Thr Ala Glu Val Gln Lys Val Gln Leu Thr Gly Glu Pro
```

-continued

```
145                 150                 155                 160
Val Pro Met Ala Arg Cys Val Ser Thr Gly Gly Arg Pro Pro Ala Gln
                165                 170                 175

Ile Thr Trp His Ser Asp Leu Gly Gly Met Pro Asn Thr Ser Gln Val
                180                 185                 190

Pro Gly Phe Leu Ser Gly Thr Val Thr Val Thr Ser Leu Trp Ile Leu
            195                 200                 205

Val Pro Ser Ser Gln Val Asp Gly Lys Asn Val Thr Cys Lys Val Glu
        210                 215                 220

His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
                260                 265                 270

Glu Pro Thr Gly Tyr Asn Trp Ser Thr Thr Met Gly Pro Leu Pro Pro
            275                 280                 285

Phe Ala Val Ala Gln Gly Ala Gln Leu Leu Ile Arg Pro Val Asp Lys
        290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
                325                 330                 335

His Ser Gly Met Ser Arg Asn Ala Ile Ile Phe Leu Val Leu Gly Ile
                340                 345                 350

Leu Val Phe Leu Ile Leu Leu Gly Ile Gly Ile Tyr Phe Tyr Trp Ser
            355                 360                 365

Lys Cys Ser Arg Glu Val Leu Trp His Cys His Leu Cys Pro Ser Ser
        370                 375                 380

Glu His His Gln Ser Cys Arg Asn
385                 390
```